(12) United States Patent
Mettus et al.

(10) Patent No.: US 7,429,454 B2
(45) Date of Patent: Sep. 30, 2008

(54) DNA PROBES USEFUL IN DETECTING δ-ENDOTOXIN-ENCODING SEQUENCES AND USES THEREOF

(75) Inventors: Anne-Marie Light Mettus, Feasterville, PA (US); James A. Baum, Doylestown, PA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/332,654

(22) Filed: Jan. 13, 2006

(65) Prior Publication Data

US 2006/0123512 A1 Jun. 8, 2006

Related U.S. Application Data

(62) Division of application No. 10/120,255, filed on Apr. 10, 2002, now Pat. No. 7,022,897, which is a division of application No. 09/184,748, filed on Nov. 2, 1998, now Pat. No. 6,468,523.

(51) Int. Cl.
*C12Q 1/68* (2006.01)
*C12N 15/11* (2006.01)

(52) U.S. Cl. .................................. 435/6; 536/24.32

(58) Field of Classification Search .................. None
See application file for complete search history.

(56) References Cited

U.S. PATENT DOCUMENTS

| | | | | |
|---|---|---|---|---|
| 5,436,002 | A | 7/1995 | Payne et al. | 424/93.461 |
| 5,596,071 | A | 1/1997 | Payne et al. | 530/350 |
| 5,824,792 | A * | 10/1998 | Payne et al. | 536/23.71 |

FOREIGN PATENT DOCUMENTS

| | | |
|---|---|---|
| GB | 220238 | 9/1988 |
| WO | WO 90/13651 | 11/1990 |
| WO | WO 98/13497 | 11/1990 |
| WO | WO94/23036 | 10/1994 |
| WO | WO96/04284 | 2/1996 |
| WO | WO 96/10083 | 4/1996 |

OTHER PUBLICATIONS de Maagd et al, 1999, Appl. Environ. Microbiol. 65:4369-4374.*
Tounsi et al, 2003, J. Appl. Microbiol. 95:23-28.*
Angsuthanasombat et al, 2001, J. Biochem. Mol. Biol. 34:402-407.*
Aaronson et al, 2001, FEMS Microbiol. Lett. 195:1-8.*
de Maagd et al, 2001, Trends Genet. 17:193-199.*
Guo et al, 2004, Proc. Natl. Acad. Sci. USA 101: 9205-9210.*
Donovan, et al., "Characterization of Two Genes Encoding *Bacillus thuringiensis* Insecticidal Crystal Proteins Toxic to Coleoptera Species," Appl. Environ. Microbiol., 58(12):3921-3937, 1992.
Donovan, et al., "Isolation and Characterization of EG2158, a New Strain of *Bacillus thuringiensis* Toxic to Coleopteran Larvae, and Nucleotide Sequence of the Toxin Gene," Mol. Gen. Genet., 214(3):365-372, 1988.
English and Slatin, "Mode of Action of Delta-Endotoxins from *Bacillus thuringiensis*: A Comparison with other Bacterial Toxins," Insect Biochem. Mol. Biol., 22:1-7, 1992.
PCT International Search Report dated Apr. 7, 2000 for International Application No. PCT/US99/25492.
Gallo, et al., Insecticidal Effectiveness of *Mammea americana* (Guttiferae) Extracts on Larvae of *Diabrotica Virgifera virgifera* (Coleoptera:Chrysomelidae) and *Trichoplusia ni* (Lepidoptera:Noctuidae)—Economic Botany 50(2) pp. 236-242 (1996).
Claudio Avignone-Rossa et al., "Bacillus Thuringiensis Growth and Toxicity," *Molecular Biotechnology*, 4:55-71 (1995).

* cited by examiner

*Primary Examiner*—Anne R Kubelik
(74) *Attorney, Agent, or Firm*—Timothy K. Ball, Esq.; Howrey LLP

(57) ABSTRACT

Disclosed are novel DNA probes useful in detecting a nucleic acid sequence encoding a novel Lepidopteran- and Coleopteran-active δ-endotoxin polypeptide. Also disclosed are nucleic acid detection methods and kits involving the novel DNA probes.

4 Claims, 1 Drawing Sheet

Figure 1:
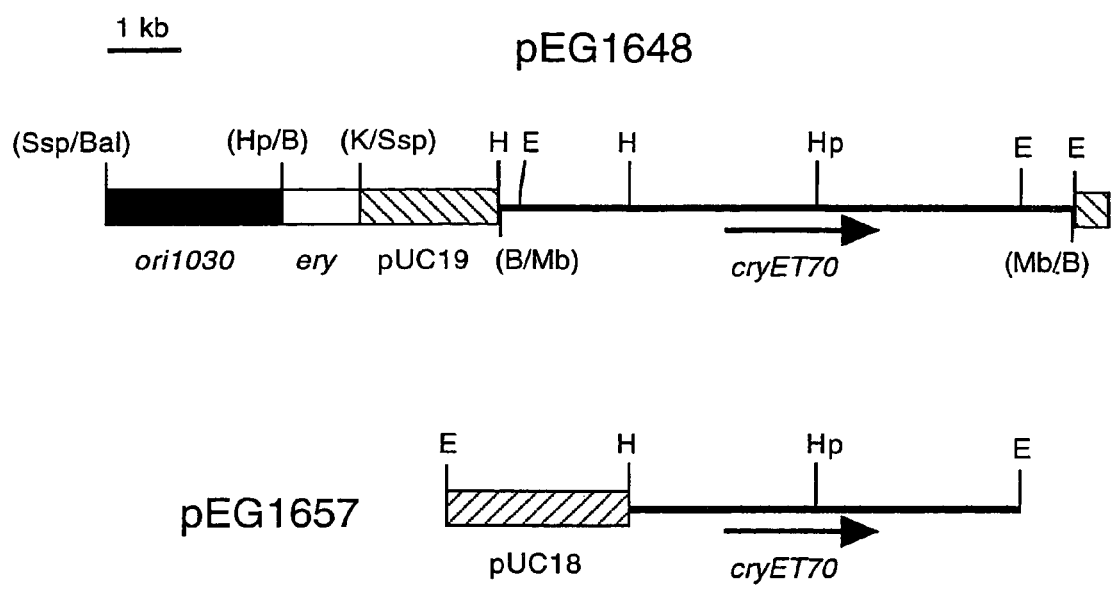

DNA PROBES USEFUL IN DETECTING δ-ENDOTOXIN-ENCODING SEQUENCES AND USES THEREOF

This application is a divisional of application Ser. No. 10/120,255, filed Apr. 10, 2002, now U.S. Pat. No. 7,022,897 which is a divisional of application Ser. No. 09/184,748 filed Nov. 2, 1998, now issued as U.S. Pat. No. 6,468,523, the entire content of each of which is hereby incorporated by reference.

1.0 BACKGROUND OF THE INVENTION

1.1 Field of the Invention

The present invention relates generally to the fields of molecular biology. Provided are methods and compositions comprising DNA segments, and polypeptides derived from bacterial species for use in insecticidal formulations and the development of transgenic insect-resistant plants. More particularly, it concerns novel nucleic acids obtained from *Bacillus thuringiensis* that encode coleopteran- and lepidopteran-toxic polypeptides. Various methods for making and using these nucleic acids, DNA segments encoding synthetically-modified CryET70 polypeptides, and native and synthetic polypeptide compositions are also disclosed. The use of DNA segments as diagnostic probes and templates for protein production, and the use of polypeptides, fusion proteins, antibodies, and peptide fragments in various immunological and diagnostic applications are also disclosed, as are methods of making and using nucleic acid segments in the development of transgenic plant cells comprising the polynucleotides disclosed herein.

1.2 Description of the Related Art

Because crops of commercial interest are often the target of insect attack, environmentally-sensitive methods for controlling or eradicating insect infestation are desirable in many instances. This is particularly true for farmers, nurserymen, growers, and commercial and residential areas which seek to control insect populations using eco-friendly compositions. The most widely used environmentally-sensitive insecticidal formulations developed in recent years have been composed of microbial pesticides derived from the bacterium *Bacillus thuringiensis*. *B. thuringiensis* is a Gram-positive bacterium that produces crystal proteins or inclusion bodies which are specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as environmentally-acceptable insecticides because they are quite toxic to the specific target insect, but are harmless to plants and other non-targeted organisms.

1.2.1 δ-Endotoxins

δ-endotoxins are used to control a wide range of leaf-eating caterpillars and beetles, as well as mosquitoes. These proteinaceous parasporal crystals, also referred to as insecticidal crystal proteins, crystal proteins, Bt inclusions, crystalline inclusions, inclusion bodies, and Bt toxins, are a large collection of insecticidal proteins produced by *B. thuringiensis* that are toxic upon ingestion by a susceptible insect host. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

One of the unique features of *B. thuringiensis* is its production of crystal proteins during sporulation which are specifically toxic to certain orders and species of insects. Many different strains of *B. thuringiensis* have been shown to produce insecticidal crystal proteins. Compositions including *B. thuringiensis* strains which produce proteins having insecticidal activity against lepidopteran and dipteran insects have been commercially available and used as environmentally-acceptable insecticides because they are quite toxic to the specific target insect, but are harmless to plants and other non-targeted organisms.

The mechanism of insecticidal activity of the *B. thuringiensis* crystal proteins has been studied extensively in the past decade. It has been shown that the crystal proteins are toxic to the insect only after ingestion of the protein by the insect. The alkaline pH and proteolytic enzymes in the insect mid-gut solubilize the proteins, thereby allowing the release of components which are toxic to the insect. These toxic components disrupt the mid-gut cells, cause the insect to cease feeding, and, eventually, bring about insect death. For this reason, *B. thuringiensis* has proven to be an effective and environmentally safe insecticide in dealing with various insect pests.

As noted by Höfte et al., (1989) the majority of insecticidal *B. thuringiensis* strains are active against insects of the order Lepidoptera, i.e., caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles (Krieg et al., 1983; Sick et al., 1990; Lambert et al., 1992a; 1992b).

1.2.2 Genes Encoding Crystal Proteins

Many of the δ-endotoxins are related to various degrees by similarities in their amino acid sequences. Historically, the proteins and the genes which encode them were classified based largely upon their spectrum of insecticidal activity. The review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins.

Based on the degree of sequence similarity, the proteins were further classified into subfamilies; more highly related proteins within each family were assigned divisional letters such as CryIA, CryIB, CryIC, etc. Even more closely related proteins within each division were given names such as CryIC1, CryIC2, etc.

Recently, a new nomenclature was developed which systematically classified the Cry proteins based upon amino acid sequence homology rather than upon insect target specificities. The classification scheme for many known toxins, not including allelic variations in individual proteins, is summarized in Table 2 of Section 4.3.

1.2.3 Identification of Crystal Proteins Toxic to WCRW Insects

The cloning and expression of the cry3Bb gene has been described (Donovan et al., 1992). This gene codes for a protein of 74 kDa with activity against Coleopteran insects, particularly the Colorado potato beetle (CPB) and the southern corn root worm (SCRW).

A *B. thuringiensis* strain, PS201T6, was reported to have activity against WCRW (*Diabrotica virgifera virgifera*) (U.S. Pat. No. 5,436,002, specifically incorporated herein by reference). This strain also had activity against *Musca domestica, Aedes aegypti*, and *Liriomyza trifoli*. The vip1A gene, which produces a vegetative, soluble, insecticidal protein, has been cloned and sequenced (Intl. Pat. Appl. Pub. No. WO 96/10083, 1996). This gene produces a protein of approximately 80 kDa with activity against WCRW and Northern Corn Root Worm (NCRW). Another toxin protein with activity against coleopteran insects, including WCRW, is Cry1Ia, an 81-kDa polypeptide, the gene encoding which has been cloned and sequenced (Intl. Pat. Appl. Pub. No. WO 90/13651, 1990).

The cryET29 gene described by Rupar et al. (Intl. Pat. Appl. Pub. No. WO 98/13497, 1998) encodes a polypeptide of approximately 26 kDa that has activity against WCRW, SCRW, as well as activity against the larvae of the Colorado potato beetle and the cat flea, *Ctenocephalides felis*.

2.0 SUMMARY OF THE INVENTION

In sharp contrast to the prior art, the polypeptide of the present invention and the novel DNA sequence that encodes it represent a new class of *B. thuringiensis* crystal proteins, and do not share sequence homology with any of the WCRW-active endotoxins described in the aforementioned literature. Likewise, the *B. thuringiensis* strains of the present invention comprise novel gene sequences that express a polypeptide having insecticidal activity against both coleopteran and leipdopteran insects, including WCRW.

Disclosed and claimed herein is an isolated *Bacillus thuringiensis* δ-endotoxin polypeptide comprising at least 10 contiguous amino acids from SEQ ID NO:2. More preferably the polypeptide comprises at least 12 to 14 contiguous amino acids from SEQ ID NO:2. Still more preferably, the polypeptide comprises at least 16 to 18 contiguous amino acids from SEQ ID NO:2, and more preferably comprises at least 20 to 30 contiguous amino acids from SEQ ID NO:2. In an exemplary embodiment, the inventors have identified an insecticidally-active polypeptide comprising the 721 amino acid long sequence of SEQ ID NO:2. Preferably such a polypeptide has insecticidal activity against both coleopteran and lepidopteran insects. For example, the inventors have shown that a δ-endotoxin polypeptide comprising the sequence of SEQ ID NO:2 has insecticidal activity against WCRW and Colorado potato beetle (CPB), as well as the lepidopteran insects *Plutella xylostella* and *Trichoplusia ni*.

Such polypeptides preferably are encoded by a nucleic acid segment comprising at least 23 contiguous nucleotides from SEQ ID NO:1, and more preferably are encoded by a nucleic acid segment comprising at least 35 contiguous nucleotides from SEQ ID NO:1. Exemplary polynucleotides encoding the insecticidal polypeptide comprise a nucleic acid segment comprising at least 45 contiguous nucleotides from SEQ ID NO:1, and in one embodiment comprise the coding region from nucleotide 92 to nucleotide 2254 of SEQ ID NO:1. The invention also discloses compositions and insecticidal formulations that comprise such a polypeptide. Such composition may be a cell extract, cell suspension, cell homogenate, cell lysate, cell supernatant, cell filtrate, or cell pellet of a bacteria cell that comprises a polynucleotide that encodes such a polypeptide. Exemplary bacterial cells that produce such a polypeptide include *Bacillus thuringiensis* EG4140, EG11839, NRRL B-21885 and NRRL B-21886 cells. The composition as described in detail hereinbelow may be formulated as a powder, dust, pellet, granule, spray, emulsion, colloid, solution, or such like, and may be preparable by such conventional means as desiccation, lyophilization, homogenization, extraction, filtration, centrifugation, sedimentation, or concentration of a culture of cells comprising the polypeptide. Preferably such compositions are obtainable from cultures of *Bacillus thuringiensis* EG4140, EG11839, NRRL B-21885 or NRRL B-21886 cells. In all such compositions that contain at least one such insecticidal polypeptide, the polypeptide may be present in a concentration of from about 1% to about 99% by weight.

An exemplary insecticidal polypeptide formulation may be prepared by a process comprising the steps of culturing *Bacillus thuringiensis* EG4140, EG11839, NRRL B-21885 or NRRL B-21886 cells under conditions effective to produce the insecticidal polypeptide; and obtaining the insecticidal polypeptide so produced.

For example, the invention discloses and claims a method of preparing a δ-endotoxin polypeptide having insecticidal activity against a coleopteran or lepidopteran insect. The method generally involves isolating from a culture of *Bacillus thuringiensis* EG4140, EG11839, NRRL B-21885 or NRRL B-21886 cells that have been grown under appropriate conditions, the δ-endotoxin polypeptide produced by the cells. Such polypeptides may be isolated from the cell culture or supernatant or from spore suspensions derived from the cell culture and used in the native form, or may be otherwise purified or concentrated as appropriate for the particular application.

A method of controlling a lepidopteran or coleopteran insect population is also provided by the invention. The method generally involves contacting the population with an insecticidally-effective amount of a polypeptide comprising the amino acid sequence of SEQ ID NO:2. Such methods may be used to kill or reduce the numbers of lepidopteran or coleopteran insects in a given area, or may be prophylactically applied to an environmental area to prevent infestation by a susceptible insect. Preferably the insect ingests, or is contacted with, an insecticidally-effective amount of the polypeptide.

Additionally, the invention provides a purified antibody that specifically binds to the insecticidal polypeptide. Also provided are methods of preparing such an antibody, and methods for using the antibody to isolate, identify, characterize, and/or purify polypeptides to which such an antibody specifically binds. Immunological kits and immunodetection methods useful in the identification of such polypeptides and peptide fragments and/or epitopes thereof are provided in detail herein, and also represent important aspects of the present invention.

Such antibodies may be used to detect the presence of such polypeptides in a sample, or may be used as described hereinbelow in a variety of immunological methods. An exemplary method for detecting a δ-endotoxin polypeptide in a biological sample generally involves obtaining a biological sample suspected of containing a δ-endotoxin polypeptide; contacting the sample with an antibody that specifically binds to the polypeptide, under conditions effective to allow the formation of complexes; and detecting the complexes so formed.

For such methods, the invention also provides an immunodetection kit. Such a kit generally contains, in suitable container means, an antibody that binds to the δ-endotoxin polypeptide, and at least a first immunodetection reagent.

Optionally, the kit may provide additional reagents or instructions for using the antibody in the detection of δ-endotoxin polypeptides in a sample.

Preparation of such antibodies may be achieved using the disclosed polypeptide as an antigen in an animal as described below. Antigenic epitopes, shorter peptides, peptide fusions, carrier-linked peptide fragments, and the like may also be generated from a whole or a portion of the polypeptide sequence disclosed in SEQ ID NO:2. Particularly preferred peptides are those that comprise at least 10 contiguous amino acids from the sequence disclosed in SEQ ID NO:2.

In another embodiment, the present invention also provides nucleic acid segments that comprise a selected nucleotide sequence region that comprises the polynuclotide sequence of SEQ ID NO:1. In preferred embodiments, this selected nucleotide sequence region comprises a gene that encodes a polypeptide comprising at least 10 contiguous amino acid residues from SEQ ID NO:2, and more preferably, comprises the amino acid sequence of SEQ ID NO:2. In one example, the gene encoding the polypeptide of SEQ ID NO:2 comprises a coding region that extends from nucleotide 92 to nucleotide 2254 of SEQ ID NO:1.

Another aspect of the invention relates to a biologically-pure culture of a wild-type *B. thuringiensis* bacterium, strain EG4140, deposited on Nov. 20, 1997 with the Agricultural Research Culture Collection, Northern Regional Research Laboratory (NRRL) having Accession No. B-21885. *B. thuringiensis* EG4140 is described infra in Section 5.0. *B. thuringiensis* EG4140 is a naturally-occurring strain that contains a sequence region that is highly homologous to, and preferably identical to, a polynucleotide sequence that encodes the 721 amino acid long polypeptide sequence in SEQ ID NO:2. In an exemplary embodiment, the strain comprises a nucleotide sequence comprising the cryET70 gene disclosed in SEQ ID NO:1. EG4140 produces an 87-kDa insecticidal polypeptide that is related to, or identical to, the polypeptide disclosed in SEQ ID NO:2.

A further embodiment of the invention relates to a vector comprising a sequence region that encodes a polypeptide comprising the amino acid sequence of SEQ ID NO:2, a recombinant host cell transformed with such a recombinant vector, and biologically-pure cultures of recombinant bacteria transformed with a polynucleotide sequence that encodes the polypeptide disclosed in SEQ ID NO:2. In an exemplary embodiment, the bacterium is *B. thuringiensis* EG11839 (deposited on Nov. 20, 1997 with the NRRL and having the accession number B-21886) described herein. Both B-21885 and B-21886 were deposited with the NRRL in the Patent Culture Collection under the terms of the Budapest Treaty, and viability statements pursuant to International Receipt Form BP/4 were obtained. Exemplary vectors, recombinant host cells, transgenic cell lines, pluripotent plant cells, and transgenic plants comprising at least a first sequence region that encodes a polypeptide comprising the sequence of SEQ ID NO:2 are described in detail hereinbelow.

In a further embodiment, the invention provides methods for preparing an insecticidal polypeptide composition. In exemplary embodiments, such polypeptides may be formulated for use as an insecticidal agent, and may be used to control insect populations in an environment, including agricultural environs and the like. The formulations may be used to kill an insect, either by topical application, or by ingestion of the polypeptide composition by the insect. In certain instances, it may be desirable to formulate the polypeptides of the present invention for application to the soil, on or near plants, trees, shrubs, and the like, near live plants, livestock, domiciles, farm equipment, buildings, and the like.

The present invention also provides transformed host cells, pluripotent plant cell populations, embryonic plant tissue, plant calli, plantlets, and transgenic plants that comprise a seleceted sequence region that encodes the insecticidal polypeptide. Such cells are preferably preferably prokaryotic or eukaryotic cells such as bacterial, fungal, or plant cells, with exemplary bacterial cells including *Bacillus thuringiensis, Bacillus subtilis, Bacillus megaterium, Bacillus cereus, Escherichia, Salmonella, Agrobacterium* or *Pseudomonas* cells (such as *Bacillus thuringiensis* EG4140, EG11839, NRRL B-21885 and NRRL B-21886 cells).

The plants and plant host cells are preferably monocotyledonous or dicotyledonous plant cells such as corn, wheat, soybean, oat, cotton, rice, rye, sorghum, sugarcane, tomato, tobacco, kapok, flax, potato, barley, turf grass, pasture grass, berry, fruit, legume, vegetable, ornamental plant, shrub, cactus, succulent, and tree cell.

Illustrative transgenic plants of the present invention preferably have incorporated into their genome a selected polynucleotide (or "transgene"), that comprises at least a first sequence region that encodes the insecticidal polypeptide of SEQ ID NO:2.

Likewise, a progeny (decendant, offspring, etc.) of any generation of such a transgenic plant also represents an important aspect of the invention. Preferably such progeny comprise the selected transgene, and inherit the phenotypic trait of insect resistance demonstrated by the parental plant. A seed of any generation of all such transgenic insect-resistant plants is also an important aspect of the invention. Preferably the seed will also comprise the selected transgene and will confer to the plants grown from the seed the phenotypic trait of insect resistance.

Insect resistant, crossed fertile transgenic plants comprising a transgene that encodes the polypeptide of SEQ ID NO:2 may be prepared by a method that generally involves obtaining a fertile transgenic plant that contains a chromosomally incorporated transgene encoding the insecticidal polypeptide of SEQ ID NO:2; operably linked to a promoter active in the plant; crossing the fertile transgenic plant with a second plant lacking the transgene to obtain a third plant comprising the transgene; and backcrossing the third plant to obtain a backcrossed fertile plant. In such cases, the transgene may be inherited through a male parent or through a female parent. The second plant may be an inbred, and the third plant may be a hybrid.

Likewise, an insect resistant hybrid, transgenic plant may be prepared by a method that generally involves crossing a first and a second inbred plant, wherein one or both of the first and second inbred plants comprises a chromosomally incorporated transgene that encodes the polypeptide of SEQ ID NO:2 operably linked to a plant expressible promoter that expresses the transgene. In illustrative embodiments, the first and second inbred plants may be monocot plants selected from the group consisting of: corn, wheat, rice, barley, oats, rye, sorghum, turfgrass and sugarcane.

In related embodiment, the invention also provides a method of preparing an insect resistant plant. The method generally involves contacting a recipient plant cell with a DNA composition comprising at least a first transgene that encodes the polypeptide of SEQ ID NO:2 under conditions permitting the uptake of the DNA composition; selecting a recipient cell comprising a chromosomally incorporated transgene that encodes the polypeptide; regenerating a plant from the selected cell; and identifying a fertile transgenic plant that has enhanced insect resistance relative to the corresponding non-transformed plant.

A method of producing transgenic seed generally involves obtaining a fertile transgenic plant comprising a chromosomally integrated transgene that encodes a polypeptide comprising the amino acid sequence of SEQ ID NO:2, operably linked to a promoter that expresses the transgene in a plant; and growing the plant under appropriate conditions to produce the transgenic seed.

A method of producing progeny of any generation of an insect resistance-enhanced fertile transgenic plant is also provided by the invention. The method generally involves collecting transgenic seed from a transgenic plant comprising a chromosomally integrated transgene that encodes the polypeptide of SEQ ID NO:2, operably linked to a promoter that expresses the transgene in the plant; planting the collected transgenic seed; and growing the progeny transgenic plants from the seed.

These methods for creating transgenic plants, progeny and seed may involve contacting the plant cell with the DNA composition using one of the processes well-known for plant cell transformation such as microprojectile bombardment, electroporation or *Agrobacterium*-mediated transformation.

These and other embodiments of the present invention will be apparent to those of skill in the art from the following examples and claims, having benefit of the teachings of the Specfication herein.

2.1 CryET70 Polynucleotide Segments

The present invention provides nucleic acid segments, that can be isolated from virtually any source, that are free from total genomic DNA and that encode the novel insecticidal polypeptides and peptide fragments thereof that are disclosed herein. The polynucleotides encoding these peptides and polypeptides may encode active insecticidal proteins, or peptide fragments, polypeptide subunits, functional domains, or the like of one or more CryET70 or CryET70-related crystal proteins, such as the polypeptide disclosed in SEQ ID NO:2. In addition the invention encompasses nucleic acid segments which may be synthesized entirely in vitro using methods that are well-known to those of skill in the art which encode the novel CryET70 polypeptide, peptides, peptide fragments, subunits, or functional domains disclosed herein.

As used herein, the term "nucleic acid segment" or "polynucleotide" refers to a nucleic acid molecule that has been isolated free of the total genomic DNAs of a particular species. Therefore, a nucleic acid segment or polynucleotide encoding an endotoxin polypeptide refers to a nucleic acid molecule that comprises at least a first crystal protein-encoding sequences yet is isolated away from, or purified free from, total genomic DNA of the species from which the nucleic acid segment is obtained, which in the instant case is the genome of the Gram-positive bacterial genus, *Bacillus*, and in particular, the species of *Bacillus* known as *B. thuringiensis*. Included within the term "nucleic acid segment", are polynucleotide segments and smaller fragments of such segments, and also recombinant vectors, including, for example, plasmids, cosmids, phagemids, phage, virions, baculoviruses, artificial chromosomes, viruses, and the like. Accordingly, polynucleotide sequences that have between about 70% and about 80%, or more preferably between about 81% and about 90%, or even more preferably between about 91% and about 99% nucleic acid sequence identity or functional equivalence to the polynucleotide sequence of SEQ ID NO:1 will be sequences that are "essentially as set forth in SEQ ID NO:1." Highly preferred sequences, are those which are preferably about 91%, about 92%, about 93%, about 94%, about 95%, about 96%, about 97%, about 98%, about 99%, or about 100% identical or functionally equivalent to the nucleotide sequence of SEQ ID NO:1. Other preferred sequences that encode CryET70- or CryET70-related sequences are those which are about 81%, 82%, 83%, 84%, 85%, 86%, 87%, 88%, 89%, or 90% identical or functionally equivalent to the polynucleotide sequence set forth in SEQ ID NO:1. Likewise, sequences that are about 71%, 72%, 73%, 74%, 75%, 76%, 77%, 78%, 79%, or 80% identical or functionally equivalent to the polynucleotide sequence set forth in SEQ ID NO:1 are also contemplated to be useful in the practice of the present invention.

Similarly, a polynucleotide comprising an isolated, purified, or selected gene or sequence region refers to a polynucleotide which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, or polypeptide-encoding unit. As will be understood by those in the art, this functional term includes both genomic sequences, operator sequences and smaller engineered gene segments that express, or may be adapted to express, proteins, polypeptides or peptides. In certain embodiments, a nucleic acid segment will comprise at least a first gene that encodes a polypeptide comprising the sequence of SEQ ID NO:2.

To permit expression of the gene, and translation of the mRNA into mature polypeptide, the nucleic acid segment preferably also comprises at least a first promoter operably linked to the gene to express the gene product in a host cell transformed with this nucleic acid segment. The promoter may be an endogenous promoter, or alternatively, a heterologous promoter selected for its ability to promote expression of the gene in one or more particular cell types. For example, in the creation of transgenic plants and pluripotent plant cells comprising a cryET70 gene, the heterologous promoter of choice is one that is plant-expressible, and in many instances, may preferably be a plant-expressible promoter that is tissue- or cell cycle-specific. The selection of plant-expressible promoters is well-known to those skilled in the art of plant transformation, and exemplary suitable promoters are described herein. In certain embodiments, the plant-expressible promoter may be selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated polynucleotides (such as DNAs, RNAs, antisense DNAs, antisense RNAs, ribozymes, and PNAs) and recombinant vectors comprising polynucleotide sequences that encode one or more polypeptides comprise all or at least 10 contiguous contiguous amino acids from SEQ ID NO:2.

The term "a sequence essentially as set forth in SEQ ID NO:2" means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acid sequence of SEQ ID NO:2 will be sequences that are "essentially as set forth in SEQ ID NO:2." Highly preferred sequences, are those which are preferably about 91%, about 92%, about 93%, about 94%, about 95%, about 96%, about 97%, about 98%, about 99%, or about 100% identical or functionally equivalent to the amino acid sequence of SEQ ID NO:2. Other preferred sequences are those which are about 81%, 82%, 83%, 84%, 85%, 86%, 87%, 88%, 89%, or 90% identical or functionally equivalent to the amino acid sequence of SEQ ID NO:2. Likewise, sequences that are about 71%, 72%, 73%, 74%, 75%, 76%, 77%, 78%, 79%, or 80% identical or functionally equivalent to the polypeptide sequence set forth in SEQ ID NO:2 are also contemplated to be useful in the practice of the present invention.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. For example, nucleic acid fragments may be prepared that include a short contiguous stretch encoding the peptide sequence disclosed in SEQ ID NO:2, or that are identical to or complementary to nucleic acid sequences which encode the peptides disclosed in SEQ ID NO:2, and particularly those nucleic acid segments disclosed in SEQ ID NO:1. For example, nucleic acid sequences such as about 23 nucleotides, and that are up to about 10,000, about 5,000, about 3,000, about 2,000, about 1,000, about 500, about 200, about 100, about 50, and about 23 or so base pairs in length (including all intermediate lengths) that comprise a contiguous nucleotide sequence from SEQ ID NO:1, or those that encode a contiguous amino acid sequence from SEQ ID NO:2 are contemplated to be particularly useful.

In one embodiment, the invention also provides an isolated nucleic acid segment characterized as: (i) a nucleic acid segment comprising a sequence region that consists of at least 23 contiguous nucleotides that have the same sequence as, or are complementary to, 23 contiguous nucleotides of SEQ ID NO:1; or (ii) a nucleic acid segment of from 23 to about 2344 nucleotides in length that hybridizes to the nucleic acid segment of SEQ ID NO:1; or the complement thereof, under standard high-stringency hybridization conditions.

It will be readily understood that "intermediate lengths", in the context of polynucleotide sequences, or nucleic acid segments, or primer or probes specific for the disclosed gene, means any length between the quoted ranges, such as from about 24, 25, 26, 27, 28, 29, etc.; 30, 31, 32, 33, 34, 35, 36, 37, 38, 39, etc.; 40, 41, 42, 43, 44, 45, 46, 47, 48, 49, 50, 51, 52, 53, 54, 55, 56, 57, 58, 59, 60, 65, 70, 75, 80, 85, 90, 95, etc.; 100, 101, 102, 103, 104, etc.; 110, 120, 125, 130, 135, 140, 145, 150, 155, 160, 165, 170, 180, 190, etc.; including all integers in the ranges of from about 200-500; 500-1,000; 1,000-2,000; 2,000-3,000; 3,000-5,000; and up to and including sequences of about 10,000 or so nucleotides and the like.

Likewise, it will be readily understood that "intermediate lengths", in the context of polypeptides or peptides, means any length between the quoted ranges of contiguous amino acids. For example, when considering CryET70-derived peptides, all lengths between about 10 and about 100 contiguous amino acid sequences are contemplated to be useful in particular embodiments disclosed herein. For example, peptides comprising contiguous amino acid sequences having about 10, about 11, about 12, about 13, about 14, about 15, about 16, about 17, about 18, about 19, about 20, about 21, about 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, etc., 70, 75, etc., 80, 85, etc., 90, 95, etc., and even those peptides comprising at least about 96, 97, 98, 99, 100, 101, 102, 103, and 104, or more contigous amino acids from SEQ ID NO:2 are explicitly considered to fall within the scope of the present invention.

Furthermore, it will also be readily understood by one of skill in the art, that "intermediate lengths", in the context of larger CryET70 and CryET70-related polypeptides, means any length between the quoted ranges of contiguous amino acids that comprise such a polypeptide. For example, when considering the polypeptides of the present invention, all lengths between about 100 and about 730 contiguous amino acid sequences are contemplated to be useful in particular embodiments disclosed herein. For example, polypeptides comprising a contiguous amino acid sequence having at least about 100, about 101, about 102, 103, 104, 105, 106, 107, 108, 109, 110, 115, 120, 125, 130, 135, 140, 145, 150, 155, 160, 165, 170, 175, 180, 185, 190, 195, etc., 200, 201, 202, 203, 204, 205, 206, 207, 208, 209, 210, 220, 230, 240, 250, 260, 270, 280, 290, etc., 300, 310, 320, 330, 340, 350, 360, 370, 380, 390, 400, etc., 410, 430, 450, 470, 490, etc., 500, 525, 550, 575, 600, 650, 674, etc., 700, etc., and even those polypeptides that comprise at least about 721 or more amino acids are explicitly considered to fall within the scope of the present invention. Particularly in the case of fusion proteins comprising a whole or a portion of the amino acid sequence of SEQ ID NO:2, longer polypeptide sequences may be preferred, including sequences that comprise about 703, 740, 750, 760, 770, 780, 790, or even about 800 or greater amino acids in length.

It will also be understood that this invention is not limited to the particular nucleic acid sequences which encode peptides of the present invention, or which encode the amino acid sequence of SEQ ID NO:2, including the DNA sequence which is particularly disclosed in SEQ ID NO:1. Recombinant vectors and isolated DNA segments may therefore variously include the polypeptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level. Alternatively, native, as yet-unknown or as yet unidentified polynucleotides and/or polypeptides structurally and/or functionally-related to the sequences disclosed herein may also be identified that fall within the scope of the present invention. Such polynucleotides are those polynucleotides that encode a polypeptide structurally and/or functionally similar or identical to, the polypeptide characterized herein as a "CryET70" polynucleotide. Since the designation "CryET170" is an arbitrary name chosen to readily identify polypeptides comprising the amino acid sequence of SEQ ID NO:2, it is likely that many other polypeptides may be identified that are highly homologous to (or even identical to) this sequence, but which may have been isolated from different organisms or sources, or alternatively, may even have been synthesized entirely, or partially de novo. As such, all polypeptide sequences, whether naturally-occurring, or artificially-created, that are structurally homologous to the primary amino acid sequence of SEQ ID NO:2 and that have similar insecticidal activity against the target insects disclosed herein are considered to fall within the scope of this disclosure. Likewise, all polynucleotide sequences, whether naturally-occurring, or artificially-created, that are structurally homologous to the nucleotide sequence of SEQ ID NO:1, or that encodes a polypeptide that is homologous, and biologically-functionally equivalent to the amino acid sequence disclosed in SEQ ID NO:2 are also considered to fall within the scope of this disclosure.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length insecticidal protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein. In many cases, the promoter may be the native CryET70 promoter, or alternatively, a heterologous promoter, such as those of bacterial origin (including promoters from other crystal proteins), fungal origin, viral, phage or phagemid origin (including promoters such as CaMV35, and its derivatives, T3, T7, λ, and φ promoters and the like), or plant origin (including constitutive, inducible, and/or tissue-specific promoters and the like).

2.2 Nucleic Acid Segments as Hybridization Probes and Primers

In addition to their use in directing the expression of crystal proteins or peptides of the present invention, the nucleic acid sequences described herein also have a variety of other uses. For example, they have utility as probes or primers in nucleic acid hybridization embodiments. The invention provides a method for detecting a nucleic acid sequence encoding a δ-endotoxin polypeptide. The method generally involves obtaining sample nucleic acids suspected of encoding a δ-endotoxin polypeptide; contacting the sample nucleic acids with an isolated nucleic acid segment comprising at least 23 contiguous nucleotides from SEQ ID NO:1, under conditions effective to allow hybridization of substantially complementary nucleic acids; and detecting the hybridized complementary nucleic acids thus formed.

In the practice of such a method, it is contemplated that nucleic acid segments that comprise a sequence region that consists of at least about a 23 nucleotide long contiguous sequence that has the same sequence as, or is complementary to, an about 23 nucleotide long contiguous nucleic acid segment of SEQ ID NO:1 will find particular utility. Longer contiguous identical or complementary sequences, e.g., those of about 24, 25, 26, 27, 28, 29, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, bp, etc. (including all intermediate lengths and up to and including the full-length sequence of about 2344 base pairs encoding the CryET70 polypeptide will also be of use in certain embodiments.

Also provided is a nucleic acid detection kit comprising, in suitable container means, at least a first nucleic acid segment comprising at least 23 contiguous nucleotides from SEQ ID NO:1, and at least a first detection reagent. The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 23 to about 50, or even up to and including sequences of about 100-200 nucleotides or so, identical or complementary to the DNA sequence of SEQ ID NO:1, or to the DNA sequence of from between about nucleotide 92 and about nucleotide 2254 of SEQ ID NO:1, are particularly contemplated as hybridization probes for use in, e.g., Southern and Northern blotting. Intermediate-sized fragments will also generally find use in hybridization embodiments, wherein the length of the contiguous complementary region may be varied, such as between about 25-30, or between about 30 and about 40 or so nucleotides, but larger contiguous complementarity stretches may be used, such as those from about 200 to about 300, or from about 300 to about 400 or 500 or so nucleotides in length, according to the length complementary sequences one wishes to detect. It is even possible that longer contiguous sequence regions may be utilized including those sequences comprising at least about 600, 700, 800, 900, 1000, 1100, 1200, 1300, 1400, 1500, or more contiguous nucleotides from SEQ ID NO: 1.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids. "High stringency" hybridization conditions, e.g., typically employ relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1990; Maloy 1994; Segal, 1976; Prokop, 1991; and Kuby, 1994, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ "low stringency" or "reduced stringency" hybridization conditions such as those employing from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results. Regardless of what particular combination of salts (such as NaCl or NaCitrate and the like), organic buffers (including e.g., formamide and the like), and incubation or washing temperatures are employed, the skilled artisan will readily be able to employ hybridization conditions that are "high," "medium," or "low" stringency, and will be able to interpret the results from hybridization analyses using such conditions to determine the relative homology of a target nucleic acid sequence to that of the particular novel polynucleotide probe sequence employed from SEQ ID NO:1.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Vectors and Methods for Recombinant Expression of Cry70 and Cry70-Related Polypeptides In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise a contiguous amino acid sequence from SEQ ID NO:2.

2.4 Transgenic Plants Expressing CryET70 Polypeptides

In yet another aspect, the present invention provides methods for producing a transgenic plant that expresses a selected nucleic acid segment comprising a sequence region that encodes the novel endotoxin polypeptides of the present invention. The process of producing transgenic plants is well-known in the art. In general, the method comprises transforming a suitable plant host cell with a DNA segment that contains a promoter operatively linked to a coding region that encodes one or more CryET70 polypeptides. Such a coding region is generally operatively linked to at least a first transcription-terminating region, whereby the promoter is capable of driving the transcription of the coding region in the cell, and hence providing the cell the ability to produce the polypeptide in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises transgenic plants which express a gene, gene segment, or sequence region that encodes at least one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more transgenes, either native, synthetically modified, or mutated, that encodes an insecticidal polypeptide that is identical to, or highly homologous to the polypeptide disclosed in SEQ ID NO:2. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant. Alternatively, a second transgene may be introduced into the plant cell to confer additional phenotypic traits to the plant. Such transgenes may confer resistance to one or more insects, bacteria, fungi, viruses, nematodes, or other pathogens.

A preferred gene which may be introduced includes, for example, a crystal protein-encoding DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of pluripotent plant cells, and regeneration of a transgenic cell line from a transformed cell, cell culture, embryo, or callus tissue are well-known in the art, and are discussed herein. Vectors, (including plasmids, cosmids, phage, phagemids, baculovirus, viruses, virions, BACs [bacterial artificial chromosomes], YACs [yeast artificial chromosomes]) comprising at least a first nucleic acid segment encoding an insecticidal polypeptide for use in transforming such cells will, of course, generally comprise either the operons, genes, or gene-derived sequences of the present invention, either native, or synthetically-derived, and particularly those encoding the disclosed crystal proteins. These nucleic acid constructs can further include structures such as promoters, enhancers, polylinkers, introns, terminators, or even gene sequences which have positively- or negatively-regulating activity upon the cloned δ-endotoxin gene as desired. The DNA segment or gene may encode either a native or modified crystal protein, which will be expressed in the resultant recombinant cells, and/or which will confer to a transgenic plant comprising such a segment, an improved phenotype (in this case, increased resistance to insect attack, infestation, or colonization).

The preparation of a transgenic plant that comprises at least one polynucleotide sequence encoding a CryET70 or CryET70-derived polypeptide for the purpose of increasing or enhancing the resistance of such a plant to attack by a target insect represents an important aspect of the invention. In particular, the inventors describe herein the preparation of insect-resistant monocotyledonous or dicotyledonous plants, by incorporating into such a plant, a transgenic DNA segment encoding one or more CryET70 polypeptides which are toxic to a coleopteran or lepidopteran insect.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more CryET70 crystal proteins or polypeptides are aspects of this invention. As well-known to those of skill in the art, a progeny of a plant is understood to mean any offspring or any descendant from such a plant.

2.5 Crystal Protein Screening and Detection Kits

The present invention contemplates methods and kits for screening samples suspected of containing crystal protein polypeptides or crystal protein-related polypeptides, or cells producing such polypeptides. A kit may contain one or more antibodies specific for the CryET70 amino acid sequence shown in SEQ ID NO:2, or one or more antibodies specific for a peptide derived from the sequence shown in SEQ ID NO:2, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virally any sample suspected of comprising either a crystal protein or peptide or a crystal protein-related peptide or antibody sought to be detected, as the case may be, may be employed. It is contemplated that such embodiments may have application in the tittering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.6 Insecticidal Compositions and Methods of Use

The inventors contemplate that the polypeptide compositions disclosed herein will find particular utility as insecticides for topical and/or systemic application to field crops, grasses, fruits and vegetables, lawns, trees, and/or ornamental plants. Alternatively, the polypeptides disclosed herein may be formulated as a spray, dust, powder, or other aqueous, atomized or aerosol for killing an insect, or controlling an insect population. The polypeptide compositions disclosed herein may be used prophylactically, or alternatively, may be administered to an environment once target insects, such as WCRW, have been identified in the particular environment to be treated.

Regardless of the method of application, the amount of the active polypeptide component(s) is applied at an insecticidally-effective amount, which will vary depending on such factors as, for example, the specific target insects to be controlled, the specific environment, location, plant, crop, or agricultural site to be treated, the environmental conditions, and the method, rate, concentration, stability, and quantity of application of the insecticidally-active polypeptide composition. The formulations may also vary with respect to climatic conditions, environmental considerations, and/or frequency of application and/or severity of insect infestation.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

2.6.1 Oil Flowable Suspensions

In a preferred embodiment, the bioinsecticide composition comprises an oil flowable suspension of bacterial cells which expresses the novel crystal protein disclosed herein. Preferably the cells are *B. thuringiensis* NRRL B-21885 or NRRL B-21886 cells, however, any such bacterial host cell expressing the novel nucleic acid segments disclosed herein and producing a polypeptide comprising the amino acid sequence of SEQ ID NO:2 is contemplated to be useful. Exemplary bacterial species include those such as *B. thuringiensis, B. megaterium, B. subtilis, B. cereus, E. coli, Salmonella* spp., *Agrobacterium* spp., or *Pseudomonas* spp.

2.6.2 Water-Dispersible Granules

In another important embodiment, the bioinsecticide composition comprises a water dispersible granule. This granule comprises bacterial cells which expresses a novel crystal protein disclosed herein. Preferred bacterial cells are *B. thuringiensis* NRRL B-21885 or NRRL B-21886 cells, however, bacteria such as *B. megaterium, B. subtilis, B. cereus, E. coli, Salmonella* spp., *Agrobacterium* spp., or *Pseudomonas* spp. cells transformed with a DNA segment disclosed herein and expressing the crystal protein are also contemplated to be useful.

2.6.3 Powders, Dusts, and Spore Formulations

In a third important embodiment, the bioinsecticide composition comprises a wettable powder, dust, spore crystal formulation, cell pellet, or colloidal concentrate. This powder comprises bacterial cells which expresses a novel crystal protein disclosed herein. Preferred bacterial cells are *B. thuringiensis* NRRL B-21885 or NRRL B-21886 cells, however, bacterial cells such as those of other strains of *B. thuringien-*

*sis*, or cells of strains of bacteria such as *B. megaterium, B. subtilis, B. cereus, E. coli, Salmonella* spp., *Agrobacterium* spp., or *Pseudomonas* spp. and the like, may also be transformed with one or more nucleic acid segments as disclosed herein. Such transformed or recombinant bacterial cells will preferably express at least one polypeptide comprising an at least 10 contiguous amino acid sequence from SEQ ID NO:2, and will produce a polypeptide that has insectical activity against a target insect. Such dry forms of the insecticidal compositions may be formulated to dissolve immediately upon wetting, or alternatively, dissolve in a controlled-release, sustained-release, or other time-dependent manner. Such compositions may be applied to, or ingested by, the target insect, and as such, may be used to control the numbers of insects, or the spread of such insects in a given environment.

2.6.4 Aqueous Suspensions and Bacterial Cell Filtrates or Lysates

In a fourth important embodiment, the bioinsecticide composition comprises an aqueous suspension of bacterial cells or an aqueous suspension of parasporal crystals, or an aqueous suspension of bacterial cell lysates or filtrates, etc., such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel insecticidal polypeptides may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or colloidal preparations of such crystals and/or spores as the active bioinsecticidal composition.

2.6.5 Multifunctional Formulations

In certain embodiments, when the control of multiple insect species is desired, the insecticidal formulations described herein may also further comprise one or more chemical pesticides, (such as chemical pesticides, nematocides, fungicides, virucides, microbicides, amoebicides, insecticides, etc.), and/or one or more δ-endotoxin polypeptides having the same, or different insecticidal activities or insecticidal specificities, as the insecticidal polypeptide identified in SEQ ID NO:2. The insecticidal polypeptides may also be used in conjunction with other treatments such as fertilizers, weed killers, cryoprotectants, surfactants, detergents, insecticidal soaps, dormant oils, polymers, and/or time-release or biodegradable carrier formulations that permit long-term dosing of a target area following a single application of the formulation. Likewise the formulations may be prepared into edible "baits" or fashioned into insect "traps" to permit feeding or ingestion by a target insect of the insecticidal formulation.

The insecticidal compositions of the invention may also be used in consecutive or simultaneous application to an environmental site singly or in combination with one or more additional insecticides, pesticides, chemicals, fertilizers, or other compounds.

2.6.6 Application Methods and Effective Rates

The insecticidal compositions of the invention are applied to the environment of the target insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, including dusting, sprinkling, soil soaking, soil injection, seed coating, seedling coating, foliar spraying, aerating, misting, atomizing, fumigating, aerosolizing, and the like, are also feasible and may be required under certain circumstances such as e.g., insects that cause root or stalk infestation, or for application to delicate vegetation or ornamental plants. These application procedures are also well-known to those of skill in the art.

The insecticidal compositions of the present invention may also be formulated for preventative or prophylactic application to an area, and may in certain circumstances be applied to pets, livestock, animal bedding, or in and around farm equipment, barns, domiciles, or agricultural or industrial facilities, and the like.

The concentration of insecticidal composition which is used for environmental, systemic, topical, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the polypeptide compositions may be from about 1% to about 99% or more by weight of the protein composition, while liquid formulations may generally comprise from about 1% to about 99% or more of the active ingredient by weight. As such, a variety of formulations are preparable, including those formulations that comprise from about 5% to about 95% or more by weight of the insecticidal polypeptide, including those formulations that comprise from about 10% to about 90% or more by weight of the insecticidal polypeptide. Naturally, compositions comprising from about 15% to about 85% or more by weight of the insecticidal polypeptide, and formulations comprising from about 20% to about 80% or more by weight of the insecticidal polypeptide are also considered to fall within the scope of the present disclosure.

In the case of compositions in which intact bacterial cells that contain the insecticidal polypeptide are included, preparations will generally contain from about $10^4$ to about $10^8$ cells/mg, although in certain embodiments it may be desirable to utilize formulations comprising from about $10^2$ to about $10^4$ cells/mg, or when more concentrated formulations are desired, compositions comprising from about $10^8$ to about $10^{10}$ or $10^{11}$ cells/mg may also be formulated. Alternatively, cell pastes, spore concentrates, or crystal protein suspension concentrates may be prepared that contain the equivalent of from about $10^{12}$ to $10^{13}$ cells/mg of the active polypeptide, and such concentrates may be diluted prior to application.

The insecticidal formulation described above may be administered to a particular plant or target area in one or more applications as needed, with a typical field application rate per hectare ranging on the order of from about 50 g/hectare to about 500 g/hectare of active ingredient, or alternatively, from about 500 g/hectare to about 1000 g/hectare may be utilized. In certain instances, it may even be desirable to apply the insecticidal formulation to a target area at an application rate of from about 1000 g/hectare to about 5000 g/hectare or more of active ingredient. In fact, all application rates in the range of from about 50 g of active polypeptide per hectare to about 10,000 g/hectare are contemplated to be useful in the management, control, and killing, of target insect pests using such insecticidal formulations. As such, rates of about 100 g/hectare, about 200 g/hectare, about 300 g/hectare, about 400 g/hectare, about 500 g/hectare, about 600 g/hectare, about 700 g/hectare, about 800 g/hectare, about 900 g/hectare, about 1 kg/hectare, about 1.1 kg/hectare, about 1.2 kg/hectare, about 1.3 kg/hectare, about 1.4 kg/hectare, about 1.5 kg/hectare, about 1.6 kg/hectare, about 1.7 kg/hectare, about 1.8 kg/hectare, about 1.9 kg/hectare, about 2.0 kg/hectare, about 2.5 kg/hectare, about 3.0 kg/hectare, about 3.5 kg/hectare, about 4.0 kg/hectare, about 4.5 kg/hectare, about 6.0 kg/hectare, about 7.0 kg/hectare, about 8.0 kg/hectare, about 8.5 kg/hectare, about 9.0 kg/hectare, and even up to and including about 10.0 kg/hectare or greater of active polypeptide may be utilized in certain agricultural, industrial, and domestic applications of the pesticidal formulations described hereinabove.

2.7 Epitopic Core Sequences

The present invention is also directed to protein or peptide compositions, free from total cells and other peptides, which comprise a purified peptide which incorporates an epitope that is immunologically cross-reactive with one or more antibodies that are specific for the disclosed polypeptide sequences. In particular, the invention concerns epitopic core sequences derived from CryET70 and CryET70-related polypeptides.

As used herein, the term "incorporating an epitope(s) that is immunologically cross-reactive with one or more antibodies that are specific for the disclosed polypeptide sequence" is intended to refer to a peptide or protein antigen which includes a primary, secondary or tertiary structure similar to an epitope located within the disclosed polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic crystal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to crystal proteins, and in particular CryET70 and related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the crystal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.8 Definitions

The following words and phrases have the meanings set forth below.

A, an: In keeping with long-standing patent tradition, "a" or "an" used throughout this disclosure is intended to mean "one or more."

Comprising, comprises: In keeping with long-standing patent tradition, "comprising" and "comprises" used throughout this disclosure is intended to mean "including, but not limited to."

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived from or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or a progeny of any generation of the plant that was derived from a transformed plant cell or protoplast, wherein the plant nucleic acids contains an exogenous selected nucleic acid sequence region not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast or from transformed pluripotent plant cells as being a transgenic plant. Preferably, transgenic plants of the present invention include those plants that comprise at least a first selected polynucleotide that encodes an insecticidal polypeptide. This selected polynucleotide is preferably a δ-endotoxin coding region (or gene) operably linked to at least a first promoter that expresses the coding region to produce the insecticidal polypeptide in the transgenic plant. Preferably, the transgenic plants of the present invention that produce the encoded polypeptide demonstrate a phenotype of improved resistance to target insect pests. Such transgenic plants, their progeny, descendants, and seed from any such generation are preferably insect resistant plants.

Vector: A nucleic acid molecule capable of replication in a host cell and/or to which another nucleic acid segment can be operatively linked so as to bring about replication of the attached segment. Plasmids, phage, phagemids, and cosmids are all exemplary vectors. In many embodiments, vectors are used as a vehicle to introduce one or more selected polynucleotides into a host cell, thereby generating a "transformed" or "recombinant" host cell.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Structural maps of the cryET70 plasmids pEG1648 and pEG1657. An approximately 8.5 kb DNA fragment, obtained from a partial MboI digest of EG4140 DNA, was cloned into the unique BamHI site of shuttle vector pHT315 to generate the cryET70 plasmid pEG1648. A 5.8 kb HindIII-EcoRI fragment containing the cryET70 gene was isolated from plasmid pEG1648 and inserted into pUC18 to yield plasmid pEG1657. Designations: ori1030 (solid box)=*B. thuringiensis* plasmid replication origin; ery (open box)=erythromycin resistance gene; pUC18 and pUC19 (shaded boxes) =*E. coli* cloning vector fragments; solid line=cryET70 DNA insert. Restriction site abbreviations: B=BamHI, Bal=BalI, E=EcoRI, H=HindIII, Hp=HpaI, K=KpnI, Mb=MboI.

4.0 DESCRIPTION OF ILLUSTRATIVE EMBODIMENTS 4.1 Some Advantages of the Invention The present invention provides a novel δ-endotoxin, designated CryET70, which is highly toxic to WCRW. This protein has an amino acid sequence which is unrelated to other δ-endotoxins that are toxic to coleopteran insects. CryET70 represents a new class of coleopteran active insecticidal crystal proteins. Unlike other WCRW toxic insecticidal crystal proteins from *B. thuringiensis*, CryET70 does not have significant toxicity to SCRW or CPB. The only known protein that is related to CryET70 is Cry22, an insecticidal crystal protein that is reported to be toxic only to hymenopteran insects (GenBank Accession No. I34547).

4.2 Insect Pests

Almost all field crops, plants, and commercial farming areas are susceptible to attack by one or more insect pests. Particularly problematic are the lepidopteran and coleopteran pests identified in Table 1. For example, vegetable and cole crops such as artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, Chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm.

Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, fall webworm, filbert leafroller, filbert webworm, fruit tree leafroller, grape berry moth, grape leaffolder, grapeleaf skeletonizer, green fruitworm, gummosos-batrachedra commosae, gypsy moth, hickory shuckworm, hornworms, loopers, navel orangeworm, obliquebanded leafroller, omnivorous leafroller. omnivorous looper, orange tortrix, orangedog, oriental fruit moth, pandemis leafroller, peach twig borer, pecan nut casebearer, redbanded leafroller, redhumped caterpillar, roughskinned cutworm, saltmarsh caterpillar, spanworm, tent caterpillar, thecla-thecla basillides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, european corn borer, green cloverworm, headmoth, headworm, imported cabbageworm, loopers (including *Anacamptodes* spp.), obliquebanded leafroller, omnivorous leaftier, podworm, podworm, saltmarsh caterpillar, southwestern corn borer, soybean looper, spotted cutworm, sunflower moth, tobacco budworm, tobacco hornworm, velvetbean caterpillar.

Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, California oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, turf grasses are often attacked by pests such as armyworm, sod webworm, and tropical sod webworm.

TABLE 1

TAXONOMY OF COLEOPTERAN PESTS IN THE SUBORDERS ARCHOSTEMATA AND POLYPHAGA

| Infraorder | Superfamily | Family | Subfamily | Tribe | Genus | Species |
|---|---|---|---|---|---|---|
| | | Cupedidae (reticulated beetles) | | | *Priacma* | *P. serrata* |
| Bostrichiformia | | Dermestidae (skin and larder beetles) | | | *Attagenus* | *A. pellio* |
| Chrysomeliformia | | Cerambycidae (long-horned beetles) | | | *Agapanthia* | *Agapanthia* sp. |
| | | | Lepturinae | | *Leptura* | *Leptura* sp. (flower long-horned beetle) |
| | | | | | *Rhagium* | *Rhagium* sp. |
| | | | | | *Megacyllene* | *M. robiniae* |
| | | | Prioninae | | *Derobrachus* | *D. geminatus* |
| | | | | | *Tetraopes* | *T. tetropthalmus* |

TABLE 1-continued

TAXONOMY OF COLEOPTERAN PESTS IN THE SUBORDERS ARCHOSTEMATA AND POLYPHAGA

| Infraorder | Super-family | Family | Subfamily | Tribe | Genus | Species |
|---|---|---|---|---|---|---|
| | | Chrysomelidae (leaf beetles) | Chlamisinae | | Exema | E. neglecta |
| | | | Chrysomelinae | Chrysomelini | Chrysomela | C. tremula, Chrysomela sp. |
| | | | | | Oreina | O. cacaliae |
| | | | | Doryphorini | Chrysoline | Chrysolina sp. |
| | | | | | Leptinotarsa | L. decemlineata (Colorado potato beetle) |
| | | | | Gonioctenini | Gonioctena | G. fornicata, G. holdausi, G. intermedia, G. interposita, G. kamikawai, G. linnaeana, G. nigroplagiata, G. occidentalis, G. olivacea, G. pallida, G. quinquepunctata, G. rubripennis, G. rufipes, G. tredecim-maculata, G. variabilis, G. viminalis |
| | | | | Timarchini | Timarcha | Timarcha sp. |
| | | | Criocerinae | | Oulema | Oulema sp. |
| | | | Galerucinae | Galerucini | Monoxia | M. inornata, Monoxia sp. |
| | | | | | Ophraella | O. arctica, O. artemisiae, O. bilineata, O. communa, O. conferta, O. cribrata, O. notata, O. notulata, O. nuda, O. pilosa, O. sexvittata, O. slobodkini |
| | | | | Luperini | Cerotoma | C. trifurcata |
| | | | | | Diabrotica | D. barberi (northern corn rootworm), D. undecimpunctata, (southern corn rootworm), D. virgifera (western corn rootworm) |
| | | | unclassified Chrysomelidae | | Lachnaia | Lachnaia sp. |
| | | | | | Epitrix | E. cucumeris (Harris) (potato flea beetle), E. fuscala (eggplant flea beetle) |
| | | Curculionidae (weevils) | Curculioninae | | Anthonomus | A. grandis (boll weevil) |
| | | | Entiminae | Naupactini | Aramigus | A. conirostris, A. globoculus, A. intermedius, A. planioculus, A. tesselatus |
| | | | | | Otiorhynchus | Otiorhynchus sp. |
| | | | | Phyllobiini | Diaprepes | D. abbreviata |
| | | | | | Phyllobius | Phyllobius sp. |
| | | | | | Galapaganus | G. galapagoensis |
| | | | Hyperinae | | Hypera | H. brunneipennis (Egyptian alfalfa weevil), H. postica (alfalfa weevil), H. punctata (clover leaf weevil) |
| | | | Molytinae | | Pissodes | P. affinis, P. nemorensis, P. schwarzi, P. strobi, P. terminalis |
| | | | Rhynchophorinae | Sitophilini | Sitophilus | S. granarius (granary weevil), S. zeamais (maize weevil) |
| | | Nemonychidae | | | Lebanorhinus | L. succinus |
| | | Scolytidae | | | Ips | I. acuminatus, I. amitinus, I. cembrae, I. duplicatus, I. mannsfeldi, I. sexdentatus, I. typographus |
| | | | | | Orthotomicus | O. erosus |
| | | | | | Tomicus | T. minor |
| Cucujiformia | | Coccinellidae (ladybird beetles) | | | Epilachna | E. borealis (squash ladybird beetle), E. varivstis (Mexican bean beetle) |
| | | Cucujidae (flat bark beetles) | | | Cryptolestes | C. ferrugineus |
| | | | | | Oryzaephilus (grain beetles) | O. surinamensis (saw-toothed grain beetle) |
| | | Lagriidae (long-joined beetles) | | | Lagria | Lagria sp. |
| | | Meloidae (blister beetles) | | | Epicauta | E. funebris |
| | | | | | Meloe | M. proscarabaeus |
| | | Rhipiphoridae | | | Rhipiphorus | R. fasciatus |
| | | Tenebrionidae (darkling ground beetles) | | | Alphitobius | A. diaperinus (lesser mealworm) |

TABLE 1-continued

TAXONOMY OF COLEOPTERAN PESTS IN THE SUBORDERS ARCHOSTEMATA AND POLYPHAGA

| Infraorder | Super-family | Family | Subfamily | Tribe | Genus | Species |
|---|---|---|---|---|---|---|
| | | | | | Hegeter | H. amaroides, H. brevicollis, H. costipennis, H. fernandezi, H. glaber, H. gomerensis, H. gran-canariensis, H. impressus, H. intercedens, H. lateralis, H. plicifrons, H. politus, H. subrotundatus, H. tenui-punctatus, H. transversus, H. webbianus |
| | | | | | Misolampus | M. goudoti |
| | | | | | Palorus | P. ficicola, P. ratzeburgi (small-eyed flour beetle), P. subdepressus (depressed flour beetle) |
| | | | | | Pimelia | P. baetica, P. canariensis, P. criba, P. elevata, P. estevezi, P. fernan-dezlopezi, P. grandis, P. granulicollis, P. integra, P. interjecta, P. laevigata, P. lutaria, P. radula, P. sparsa, P. variolosa |
| | | | | | Tenebrio | T. molitor (yellow mealworm), T. obscurus (dark mealworm) |
| | | | | | Tentyria | T. schaumi |
| | | | | | Tribolium | T. brevicornis, T. castaneum (red flour beetle), T. confusum (confused flour beetle), T. freemani, T. madens |
| | | | | | Zophobas | Z. atratus Z. rugipes |
| Elateriformia | Elateroidea | | | | Octinodes | Octinodes sp. |
| | | | | | Pyrophorus | P. plagio-phthalamus |
| Scarabaeiformia | | Lucanidae (Stag beetles) | | | Dorcus | D. parallelo-pipedus |
| | | | | | Lucanus | L. cervus |
| | | Scarabaeidae (lamellicorn beetles) | | | Allomyrina | A. dichotoma |
| | | | Cetoniinae (flower beetle) | | Pachnoda | P. marginata |
| | | | Dynastinae | | Xyloryctes | X. faunus |
| | | | Geotrupinae (earth-boring dung beetles) | | Geotrupes | G. stercorosus |
| | | | Melonlonthinae (chafers) | | Costelytra | C. zealandica |
| | | | | | Holotrichia | H. diomphalia |
| | | | | | Melolontha | M. melolontha (cockchafer) |
| | | | | | Odontria | O. striata O. variegata |
| | | | | | Prodontria | P. bicolorata, P. capito, P. lewisi, P. tarsis, P. modesta, P. pinguis, P. praelatella, P. truncata, Prodontria sp. |
| | | | | | Scythrodes | S. squalidus |
| | | | Rutelinae (shining leaf chafers) | | Popillia | P. japonica (Japanese beetle) |
| | | | Scarabaeinae | | Copris | C. lunaris (black dung beetle) |
| | | | | | Scarabaeus | Scarabaeus sp. (scarab) |
| Staphyliniformia | | Hydrophilidae | | | Cercyon | Cercyon sp. |
| | | Silphidae | | | Nicrophorus | N. americanus, N. marginatus, N. orbicollis, N. tomentosus |
| | | Staphylinidae (rove beetles) | | | Carpelimus | Carpelimus sp. |
| | | | | | Quedius | Q. mesomelinus |
| | | | | | Tachyporus | Tachyporus sp. |
| | | | | | Xantholinus | Xantholinus sp. |

4.3 Nomenclature of *B. thuringiensis* δ-Endotoxins

Table 2 contains a list of the traditional, and currently recognized nomenclature for the known δ-endotoxins. Also shown are GenBank accession numbers for the sequenced polypeptides and polynucleotides.

TABLE 2

NOMENCLATURE OF KNOWN *B. THURINGIENSIS* δ-ENDOTOXINS[A]

| New | Old | GenBank Accession # |
|---|---|---|
| Cry1Aa1 | CryIA(a) | M11250 |
| Cry1Aa2 | CryIA(a) | M10917 |
| Cry1Aa3 | CryIA(a) | D00348 |
| Cry1Aa4 | CryIA(a) | X13535 |
| Cry1Aa5 | CryIA(a) | D175182 |
| Cry1Aa6 | CryIA(a) | U43605 |
| Cry1Ab1 | CryIA(b) | M13898 |
| Cry1Ab2 | CryIA(b) | M12661 |
| Cry1Ab3 | CryIA(b) | M15271 |
| Cry1Ab4 | CryIA(b) | D00117 |
| Cry1Ab5 | CryIA(b) | X04698 |
| Cry1Ab6 | CryIA(b) | M37263 |
| Cry1Ab7 | CryIA(b) | X13233 |
| Cry1Ab8 | CryIA(b) | M16463 |
| Cry1Ab9 | CryIA(b) | X54939 |
| Cry1Ab10 | CryIA(b) | A29125 |
| Cry1Ac1 | CryIA(c) | M11068 |
| Cry1Ac2 | CryIA(c) | M35524 |
| Cry1Ac3 | CryIA(c) | X54159 |
| Cry1Ac4 | CryIA(c) | M73249 |
| Cry1Ac5 | CryIA(c) | M73248 |
| Cry1Ac6 | CryIA(c) | U43606 |
| Cry1Ac7 | CryIA(c) | U87793 |
| Cry1Ac8 | CryIA(c) | U87397 |
| Cry1Ac9 | CryIA(c) | U89872 |
| Cry1Ac10 | CryIA(c) | AJ002514 |
| Cry1Ad1 | CryIA(d) | M73250 |
| Cry1Ae1 | CryIA(e) | M65252 |
| Cry1Ba1 | CryIB | X06711 |
| Cry1Ba2 |  | X95704 |
| Cry1Bb1 | ET5 | L32020 |
| Cry1Bc1 | CryIb(c) | Z46442 |
| Cry1Bd1 | CryE1 | U70726 |
| Cry1Ca1 | CryIC | X07518 |
| Cry1Ca2 | CryIC | X13620 |
| Cry1Ca3 | CryIC | M73251 |
| Cry1Ca4 | CryIC | A27642 |
| Cry1Ca5 | CryIC | X96682 |
| Cry1Ca6 | CryIC | X96683 |
| Cry1Ca7 | CryIC | X96684 |
| Cry1Cb1 | CryIC(b) | M97880 |
| Cry1Da1 | CryID | X54160 |
| Cry1Db1 | PrtB | Z22511 |
| Cry1Ea1 | CryIE | X53985 |
| Cry1Ea2 | CryIE | X56144 |
| Cry1Ea3 | CryIE | M73252 |
| Cry1Ea4 |  | U94323 |
| Cry1Eb1 | CryIE(b) | M73253 |
| Cry1Fa1 | CryIF | M63897 |
| Cry1Fa2 | CryIF | M63897 |
| Cry1Fb1 | PrtD | Z22512 |
| Cry1Ga1 | PrtA | Z22510 |
| Cry1Ga2 | CryIM | Y09326 |
| Cry1Gb1 | CryH2 | U70725 |
| Cry1Ha1 | PrtC | Z22513 |
| Cry1Hb1 |  | U35780 |
| Cry1Ia1 | CryV | X62821 |
| Cry1Ia2 | CryV | M98544 |
| Cry1Ia3 | CryV | L36338 |
| Cry1Ia4 | CryV | L49391 |
| Cry1Ia5 | CryV | Y08920 |
| Cry1Ib1 | CryV | U07642 |
| Cry1Ja1 | ET4 | L32019 |
| Cry1Jb1 | ET1 | U31527 |
| Cry1Ka1 |  | U28801 |
| Cry2Aa1 | CryIIA | M31738 |
| Cry2Aa2 | CryIIA | M23723 |
| Cry2Aa3 |  | D86084 |
| Cry2Ab1 | CryIIB | M23724 |
| Cry2Ab2 | CryIIB | X55416 |
| Cry2Ac1 | CryIIC | X57252 |
| Cry3Aa1 | CryIIIA | M22472 |
| Cry3Aa2 | CryIIIA | J02978 |
| Cry3Aa3 | CryIIIA | Y00420 |
| Cry3Aa4 | CryIIIA | M30503 |
| Cry3Aa5 | CryIIIA | M37207 |
| Cry3Aa6 | CryIIIA | U10985 |
| Cry3Ba1 | CryIIIB | X17123 |
| Cry3Ba2 | CryIIIB | A07234 |
| Cry3Bb1 | CryIIIB2 | M89794 |
| Cry3Bb2 | CryIIIC(b) | U31633 |
| Cry3Ca1 | CryIIID | X59797 |
| Cry4Aa1 | CryIVA | Y00423 |
| Cry4Aa2 | CryIVA | D00248 |
| Cry4Ba1 | CryIVB | X07423 |
| Cry4Ba2 | CryIVB | X07082 |
| Cry4Ba3 | CryIVB | M20242 |
| Cry4Ba4 | CryIVB | D00247 |
| Cry5Aa1 | CryVA(a) | L07025 |
| Cry5Ab1 | CryVA(b) | L07026 |
| Cry5Ba1 | PS86Q3 | U19725 |
| Cry6Aa1 | CryVIA | L07022 |
| Cry6Ba1 | CryVIB | L07024 |
| Cry7Aa1 | CryIIIC | M64478 |
| Cry7Ab1 | CryIIICb | U04367 |
| Cry8Aa1 | CryIIIE | U04364 |
| Cry8Ba1 | CryIIIG | U04365 |
| Cry8Ca1 | CryIIIF | U04366 |
| Cry9Aa1 | CryIG | X58120 |
| Cry9Aa2 | CryIG | X58534 |
| Cry9Ba1 | CryIX | X75019 |
| Cry9Ca1 | CryIH | Z37527 |
| Cry9Da1 | N141 | D85560 |
| Cry10Aa1 | CryIVC | M12662 |
| Cry11Aa1 | CryIVD | M31737 |
| Cry11Aa2 | CryIVD | M22860 |
| Cry11Ba1 | Jeg80 | X86902 |
| Cry12Aa1 | CryVB | L07027 |
| Cry13Aa1 | CryVC | L07023 |
| Cry14Aa1 | CryVD | U13955 |
| Cry15Aa1 | 34 kDa | M76442 |
| Cry16Aa1 | cbm71 | X94146 |
| Cry17Aa1 | cbm71 | X99478 |
| Cry18Aa1 | CryBP1 | X99049 |
| Cry19Aa1 | Jeg65 | Y08920 |
| Cry20Aa1 |  | U82518 |
| Cry21Aa1 |  | I32932 |
| Cry22Aa1 |  | I34547 |
| Cyt1Aa1 | CytA | X03182 |
| Cyt1Aa2 | CytA | X04338 |
| Cyt1Aa3 | CytA | Y00135 |
| Cyt1Aa4 | CytA | M35968 |
| Cyt1Ab1 | CytM | X98793 |
| Cyt1Ba1 |  | U37196 |
| Cyt2Aa1 | CytB | Z14147 |
| Cyt2Ba1 | "CytB" | U52043 |
| Cyt2Ba2 | "CytB" | AF020789 |
| Cyt2Ba3 | "CytB" | AF022884 |
| Cyt2Ba4 | "CytB" | AF022885 |
| Cyt2Ba5 | "CytB" | AF022886 |
| Cyt2Bb1 |  | U82519 |

[A]Adapted from: Crickmore, N. et al. Microbiol. and Mol. Biol. Rev. (1998) Vol. 62:8-7-813.

In a preferred embodiment, the invention discloses and claims an isolated and purified CryET70 polypeptide. The CryET70 polypeptide isolated from EG4140 comprises a 721-amino acid siquence, and has a calculated molecular mass of approximately 4.4 Probes And Primers In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein-encoding gene sequence, e.g., a sequence such as that shown in SEQ ID NO:1. The ability of such DNAs and nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

To provide certain of the advantages in accordance with the present invention, a preferred nucleic acid sequence employed for hybridization studies or assays includes sequences that are complementary to at least an about 23 to about 40 or so long nucleotide stretch of a crystal protein-encoding sequence, such as that shown in SEQ ID NO:1. A size of at least about 14 or 15 or so nucleotides in length helps to ensure that the fragment will be of sufficient length to form a duplex molecule that is both stable and selective. Molecules having complementary sequences over stretches greater than about 23 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, specifically incorporated herein by reference, or by excising selected DNA fragments from recombinant plasmids containing appropriate inserts and suitable restriction sites.

4.5 Expression Vectors

The present invention contemplates a polynucleotide of the present invention comprised within one or more expression vectors. Thus, in one embodiment an expression vector comprises a nucleic acid segment containing a cryET70 gene operably linked to a promoter which expresses the gene. Additionally, the coding region may also be operably linked to a transcription-terminating region, whereby the promoter drives the transcription of the coding region, and the transcription-terminating region halts transcription at some point 3' of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus*-derived crystal proteins include any of the known crystal protein gene promoters, including the cryET70 gene promoter itself. Alternatively, mutagenized or recombinant promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, constitutive, temporally-regulated, spatially-regulated, and spatio-temporally regulated, including those that are native, semi-synthetic, and synthetic (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Lel) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991a). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (van Tunen et al., 1988), bean glycine rich protein 1 (Keller et al., 1989), CaMV 35S transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are specifically incorporated herein by reference in their entirety. Those vectors can be modified to include a coding sequence in accordance with the present invention.

A variety of methods has been developed to operatively insert a DNA segment into a vector via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a CryET70 *B. thuringiensis* crystal protein-encoding gene. In preferred embodiments, such a polypeptide has the amino acid residue sequence of SEQ ID NO:2, or a functional equivalent thereof. In accordance with such embodiments, a coding region comprising the DNA sequence of SEQ ID NO:1 is also preferred 4.6 Characteristic of the CryET70 Polypeptide Isolated from EG4140

The present invention provides a novel polypeptide that defines a whole or a portion of a *B. thuringiensis* CryET70 crystal protein.

In a preferred embodiment, the invention discloses and claims an isolated and purified CryET70 polypeptide. The CryET70 polypeptide isolated from EG4140 comprises a 721-amino acid sequence, and has a calculated molecular mass of approximately 87,000 Da. CryET70 has a calculated isoelectric constant (pI) equal to.

The amino acid composition of the CryET70 polypeptide is given in Table 3.

TABLE 3

| AMINO ACID COMPOSITION OF CRYET70 | | |
|---|---|---|
| Amino Acid | # Residues | % Total |
| Ala | | |
| Arg | | |
| Asn | | |
| Asp | | |
| Cys | | |
| Gln | | |
| Glu | | |
| Gly | | |
| His | | |
| Ile | | |
| Leu | | |
| Lys | | |
| Met | | |
| Phe | | |
| Pro | | |
| Ser | | |
| Thr | | |
| Tro | | |
| Tyr | | |
| Val | | |

Acidic (Asp + Glu)
Basic (Arg + Lys)
Aromatic (Phe + Trp + Tyr)
Hydrophobic (Aromatic + Ile + Leu + Met + Val)

4.7 Nomenclature of the Novel Proteins

The inventors have arbitrarily assigned the designation CryET70 to the novel protein of the invention. Likewise, the arbitrary designation of cryET70 has been assigned to the novel nucleic acid sequence which encodes this polypeptide. Formal assignment of gene and protein designations based on the revised nomenclature of crystal protein endotoxins will be assigned by a committee on the nomenclature of *B. thuringiensis*, formed to systematically classify *B. thuringiensis* crystal proteins. The inventors contemplate that the arbitrarily assigned designations of the present invention will be superseded by the official nomenclature assigned to these sequences.

4.8 Transformed Host Cells and Transgenic Plants

Methods and compositions for transforming a bacterium, a yeast cell, a plant cell, or an entire plant with one or more expression vectors comprising a crystal protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988; Eglitis et al., 1988); and (4) receptor-mediated mechanisms (Curiel et al., 1991; 1992; Wagner et al., 1992).

4.8.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.8.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hr post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.8.3 Agrobacterium-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors. Therefore, commercially important cereal grains such as rice, corn, and wheat must usually be transformed using alternative methods. However, as mentioned above, the transformation of asparagus using *Agrobacterium* can also be achieved (see, for example, Bytebier et al., 1987).

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

4.8.4 Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.8.5 Gene Expression in Plants

Although great progress has been made in recent years with respect to preparation of transgenic plants which express bacterial proteins such as *B. thuringiensis* crystal proteins, the results of expressing native bacterial genes in plants are often disappointing. Unlike microbial genetics, little was known by early plant geneticists about the factors which affected heterologous expression of foreign genes in plants. In recent years, however, several potential factors have been implicated as responsible in varying degrees for the level of protein expression from a particular coding sequence. For example, scientists now know that maintaining a significant level of a particular mRNA in the cell is indeed a critical factor. Unfortunately, the causes for low steady state levels of mRNA encoding foreign proteins are many. First, full length RNA synthesis may not occur at a high frequency. This could, for example, be caused by the premature termination of RNA during transcription or due to unexpected mRNA processing during transcription. Second, full length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half lives (which are determined by their primary or secondary sequence) insufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure It is likely that structure per se or particular structural features also have a role in determining RNA stability.

To overcome these limitations in foreign gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since B. thuringiensis has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabiling elements or whether any of these effects are likely to be seen in plants.

Some studies on mRNA degradation in animal cells also indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). A final example is the instability of a mutant β-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability. These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Studies in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene-specific so far.

It has been shown that in natural mRNAs proper polyadenylation is important in mRNA accumulation, and that disruption of this process can effect mRNA levels significantly. However, insufficient knowledge exists to predict the effect of changes in a normal gene. In a heterologous gene, it is even harder to predict the consequences. However, it is possible that the putative sites identified are dysfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites in Table 4 called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as those encoding the crystal proteins of the present invention.

TABLE 4

POLYADENYLATION SITES IN PLANT GENES

| PA | AATAAA | Major consensus site |
|---|---|---|
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45-55% A+T.

Due to the degeneracy of the genetic code and the limited number of codon choices for any amino acid, most of the "excess" A+T of the structural coding sequences of some *Bacillus* species are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*.

Typically, to obtain high-level expression of the δ-endotoxin genes in plants, existing structural coding sequence ("structural gene") which codes for the δ-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

4.8.6 Synthetic Oligonucleotides for Mutagenesis

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 5 below) so as to avoid codons which are rarely found in plant genomes, and efforts should be made to select codons to preferably adjust the G+C content to about 50%.

TABLE 5

PREFERRED CODON USAGE IN PLANTS

| Amino Acid | Codon | Percent Usage in Plants |
|---|---|---|
| ARG | CGA | 7 |
|  | CGC | 11 |
|  | CGG | 5 |
|  | CGU | 25 |
|  | AGA | 29 |
|  | AGG | 23 |
| LEU | CUA | 8 |
|  | CUC | 20 |
|  | CUG | 10 |
|  | CUU | 28 |
|  | UUA | 5 |
|  | UUG | 30 |
| SER | UCA | 14 |
|  | UCC | 26 |
|  | UCG | 3 |
|  | UCU | 21 |
|  | AGC | 21 |
|  | AGU | 15 |
| THR | ACA | 21 |
|  | ACC | 41 |
|  | ACG | 7 |
|  | ACU | 31 |
| PRO | CCA | 45 |
|  | CCC | 19 |
|  | CCG | 9 |
|  | CCU | 26 |
| ALA | GCA | 23 |
|  | GCC | 32 |
|  | GCG | 3 |
|  | GCU | 41 |
| GLY | GGA | 32 |
|  | GGC | 20 |
|  | GGG | 11 |
|  | GGU | 37 |
| ILE | AUA | 12 |
|  | AUC | 45 |
|  | AUU | 43 |
| VAL | GUA | 9 |
|  | GUC | 20 |
|  | GUG | 28 |
|  | GUU | 43 |
| LYS | AAA | 36 |
|  | AAG | 64 |
| ASN | AAC | 72 |
|  | AAU | 28 |
| GLN | CAA | 64 |
|  | CAG | 36 |
| HIS | CAC | 65 |
|  | CAU | 35 |
| GLU | GAA | 48 |
|  | GAG | 52 |
| ASP | GAC | 48 |
|  | GAU | 52 |
| TYR | UAC | 68 |
|  | UAU | 32 |
| CYS | UGC | 78 |
|  | UGU | 22 |
| PHE | UUC | 56 |
|  | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided. Codons are selected avoiding the TA and CG doublets in codons whenever possible. Codon usage can be normalized against a plant preferred codon usage table (such as Table 5) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

4.9 Methods for Producing Insect-Resistant Transgenic Plants

By transforming a suitable host cell, such as a plant cell, with a recombinant cryET70 gene-containing segment, the expression of the encoded crystal protein (i.e. a bacterial crystal protein or polypeptide having insecticidal activity against Coleopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant, or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a gene) that encodes a polypeptide in accordance with SEQ ID NO:2. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions. The inventors contemplate that the present invention will find particular utility in the creation of transgenic plants of commercial interest including various turf and pasture grasses, rye, wheat, corn, kapok, flax, rice, barley, oats, sugarcane, cotton, tomato, potato, soybeans and other legumes, tobacco, sorghum, as well as a variety of ornamental plants including cacti and succulents, fruits, berries, vegetables, and also a number of nut- and fruit-bearing trees and plants.

Transgenic plants comprising one or more trangenes that encode a polypeptide in accordance with SEQ ID NO:2 will preferably exhibit a phenotype of improved or enhanced insect resistance to the target coleopteran and lepidopteran insects as described herein. These plants will preferably provide transgenic seeds, which will be used to create lineages of transgenic plants (i.e. progeny or advanced generations of the original transgenic plant) that may be used to produce seed, or used as animal or human foodstuffs, or to produce fibers, oil, fruit, grains, or other commercially-important plant products or plant-derived components. In such instances, the progeny and seed obtained from any generation of the transformed plants will contain the selected chromosomally-integrated transgene that encodes the δ-endotoxin of the present invention. The transgenic plants of the present invention may be crossed to produce hybrid or inbred lines with one or more plants that have desirable properties. In certain circumstances, it may also be desirable to create transgenic plants, seed, and progeny that contain one or more additional transgenes incorporated into their genome in addition to the transgene encoding the polypeptide of the invention. For example, the transgenic plants may contain a second gene encoding the same, or a different insect-resistance polypeptide, or alternatively, the plants may comprise one or more additional transgenes such as those conferring herbicide resistance, fungal resistance, bacterial resistance, stress, salt, or drought tolerance, improved stalk or root lodging, increased starch, grain, oil, carbohydrate, amino acid, protein production, and the like.

4.10 Isolating Homologous Gene and Gene Fragments

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from *Bacillus* strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxin, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

4.11 Ribozymes

Ribozymes are enzymatic RNA molecules which cleave particular mRNA species. In certain embodiments, the inventors contemplate the selection and utilization of ribozymes capable of cleaving the RNA segments of the present invention, and their use to reduce activity of target mRNAs in particular cell types or tissues.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or *Neurospora* VS RNA motif. Examples of hammerhead motifs are described by Rossi et al. (1992); examples of hairpin motifs are described by Hampel et al. (Eur. Pat. EP 0360257), Hampel and Tritz (1989), Hampel et al. (1990) and Cech et al. (U.S. Pat. No. 5,631,359; an example of the hepatitis δ virus motif is described by Perrotta and Been (1992); an example of the RNaseP motif is described by Guerrier-Takada et al. (1983); *Neurospora* VS RNA ribozyme motif is described by Collins (Saville and Collins, 1990; Saville and Collins, 1991; Collins and Olive, 1993); and an example of the Group I intron is described by Cech et al. (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

The invention provides a method for producing a class of enzymatic cleaving agents which exhibit a high degree of specificity for the RNA of a desired target. The enzymatic nucleic acid molecule is preferably targeted to a highly conserved sequence region of a target mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569), and (Int. Pat. Appl. Publ. No. WO 94/02595), both hereby incorporated in their totality by reference herein; Ohkawa et al., 1992; Taira et al., 1991; Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in (Int. Pat. Appl. Publ. No. WO 93/23569), or (Int. Pat. Appl. Publ. No. WO 94/02595) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1992) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perreault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Int. Pat. Appl. Publ. No. WO 94/02595 describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in (Int. Pat. Appl. Publ. No. WO 94/02595) and (Int. Pat. Appl. Publ. No. WO 93/23569) which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within cell lines or cell types. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in particular cells or cell types.

4.12 Recombinant Host Cells

The nucleotide sequences of the subject invention may be introduced into a wide variety of microbial and eukaryotic hosts. As hosts for recombinant expression of CryET70 polypeptides, of particular interest will be the prokaryotes and the lower eukaryotes, such as fungi. Illustrative prokaryotes, both Gram-negative and Gram-positive, include *Enterobacteriaceae*, such as *Escherichia, Erwinia, Shigella, Salmonella,* and *Proteus; Bacillaceae; Rhizobiceae*, such as *Rhizobium; Spirillaceae,* such as *photobacterium, Zymomonas, Serratia, Aeromonas, Vibrio, Desulfovibrio, Spirillum; Lactobacillaceae; Pseudomonadaceae,* such as *Pseudomonas* and *Acetobacter; Azotobacteraceae, Actinomycetales,* and *Nitrobacteraceae.* Among eukaryotes are fungi, such as *Phycomycetes* and *Ascomycetes,* which includes yeast, such as *Saccharomyces* and *Schizosaccharomyces*; and *Basidiomycetes* yeast, such as *Rhodotorula, Aureobasidium, Sporobolomyces,* and the like.

Characteristics of particular interest in selecting a host cell for purposes of production include ease of introducing the genetic constructs of the present invention into the host cell, availability of expression systems, efficiency of expression, stability of the gene of interest in the host, and the presence of auxiliary genetic capabilities.

A large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed genetic constructs. These microorganisms include bacteria, algae, and fungi. Of particular interest are microorganisms, such as bacteria, e.g., genera *Bacillus* (including the species and subspecies *B. thuringiensis kurstaki* HD-1, *B. thuringiensis kurstaki* HD-73, *B. thuringiensis sotto, B. thuringiensis berliner, B. thuringiensis thuringiensis, B. thuringiensis tolworthi, B. thuringiensis dendrolimus, B. thuringiensis alesti, B. thuringiensis galleriae, B. thuringiensis aizawai, B. thuringiensis subtoxicus, B. thuringiensis entomocidus, B. thuringiensis tenebrionis* and *B. thuringiensis san diego*); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*.

Characteristics of particular interest in selecting a host cell for purposes of production include ease of introducing a selected genetic construct into the host, availability of expression systems, efficiency of expression, stability of the polynucleotide in the host, and the presence of auxiliary genetic capabilities. Other considerations include ease of formulation and handling, economics, storage stability, and the like.

4.13 Polynucleotide Sequences

DNA compositions encoding the insecticidally-active polypeptides of the present invention are particularly preferred for delivery to recipient plant cells, in the generation of pluripotent plant cells, and ultimately in the production of insect-resistant transgenic plants. For example, DNA segments in the form of vectors and plasmids, or linear DNA fragments, in some instances containing only the DNA element to be expressed in the plant cell, and the like, may be employed.

Vectors, plasmids, phagemids, cosmids, viral vectors, shuttle vectors, baculovirus vectors, BACs (bacterial artificial chromosomes), YACs (yeast artificial chromosomes) and DNA segments for use in transforming cells with a δ-endotoxin-encoding polynucleotide, will, of course, generally comprise at least a first gene that encodes the polypeptide in accordance with SEQ ID NO:2, or a gene that encodes a polypeptide that has at least about 80% or 85% or 90% or 95% sequence identity to the amino acid sequence disclosed in SEQ ID NO:2. These nucleic acid constructs may comprise one or more genes which one desires to introduce into recipient cells. These DNA constructs can include structures such as promoters, enhancers, polylinkers, or regulatory genes as desired. The DNA segment or gene chosen for cellular introduction will often encode a polypeptide which will be expressed in the resultant recombinant cells, such as will result in a screenable or selectable trait and/or which will impart an improved phenotype to the transformed host cell. Alternatively, the nucleic acid constructs may contain antisense constructs, or ribozyme-encoding regions when delivery or introduction of such nucleic acid constructs are desirable.

4.14 Methods for Preparing Mutagenized Polynucleotides

In certain circumstances, it may be desirable to modify or alter one or more nucleotides in one or more of the polynucleotide sequences disclosed herein for the purpose of altering or changing the insecticidal activity or insecticidal specificity of the encoded polypeptide. In general, the means and methods for mutagenizing a DNA segment are well-known to those of skill in the art. Modifications to such segments may be made by random, or site-specific mutagenesis procedures. The polynucleotides may be modified by the addition, deletion, or substitution of one or more nucleotides from the sequence encoding the insecticidally-active polypeptide.

Mutagenesis may be performed in accordance with any of the techniques known in the art such as and not limited to synthesizing an oligonucleotide having one or more mutations within the sequence of a particular region. In particular, site-specific mutagenesis is a technique useful in the preparation of mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al., (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al., (1990) and Upender et al., (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected δ-endotoxin-encoding DNA segments using site-directed mutagenesis is provided as a means of producing potentially useful species and is not meant to be limiting as there are other ways in which sequence variants of DNA sequences may be obtained. For example, recombinant vectors encoding the desired sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Still other amplification methods described in Great Britain Pat. Appl. No. 2 202 328, and in Intl. Pat. Appl. Publ. No. PCT/US89/01025, each of which is incorporated herein by reference in its entirety, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H(RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR™" (Ohara, et al. 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of polynucleotide sequences of the present invention.

4.15 Post-Transcriptional Events Affecting Expression of Transgenes in Plants

In many instances, the level of transcription of a particular transgene in a given host cell is not always indicative of the amount of protein being produced in the transformed host cell. This is often due to post-transcriptional processes, such as splicing, polyadenylation, appropriate translation initiation, and RNA stability, that affect the ability of a transcript to produce protein. Such factors may also affect the stability and amount of mRNA produced from the given transgene. As such, it is often desirable to alter the post-translational events through particular molecular biology techniques. The inventors contemplate that in certain instances it may be desirable to alter the transcription and/or expression of the polypeptide-encoding nucleic acid constructs of the present invention to increase, decrease, or otherwise regulate or control these constructs in particular host cells and/or transgenic plants.

4.15.1 Efficient Initiation of Protein Translation

The 5'-untranslated leader (5'-UTL) sequence of eukaryotic mRNA plays a major role in translational efficiency. Many early chimeric transgenes using a viral promoter used an arbitrary length of viral sequence after the transcription initiation site and fused this to the AUG of the coding region. More recently studies have shown that the 5'-UTL sequence and the sequences directly surrounding the AUG can have a large effect in translational efficiency in host cells and particularly certain plant species and that this effect can be different depending on the particular cells or tissues in which the message is expressed.

In most eukaryotic mRNAs, the point of translational initiation occurs at the AUG codon closest to the 5' cap of the transcript. Comparison of plant mRNA sequences and site directed mutagenesis experiments have demonstrated the existence of a consensus sequence surrounding the initiation codon in plants, 5'-UAAACAAUGGCU-3' (SEQ ID NO:4) (Joshi, 1987; Lutcke et al., 1987). However, consensus sequences will be apparent amongst individual plant species. For example, a compilation of sequences surrounding the initiation codon from 85 maize genes yields a consensus of 5'-(C/G)AUGGCG-3' (Luehrsen et al., 1994). In tobacco protoplasts, transgenes encoding β-glucuronidase (GUS) and bacterial chitinase showed a 4-fold and an 8-fold increase in expression, respectively, when the native sequences of these genes were changed to encode 5'-ACCAUGG-3' (Gallie et al., 1987b; Jones et al., 1988).

When producing chimeric transgenes (i.e. transgenes comprising DNA segments from different sources operably linked together), often the 5'-UTL of plant viruses are used. The alfalfa mosaic virus (AMV) coat protein and brome mosaic virus (BMV) coat protein 5'-UTLs have been shown to enhance mRNA translation 8-fold in electroporated tobacco protoplasts (Gallie et al., 1987a; 1987b). A 67-nucleotide derivative (Ω) of the 5'-UTL of tobacco mosaic virus RNA (TMV) fused to the chloramphenicol acetyltransferase (CAT) gene and GUS gene has been shown to enhance translation of reporter genes in vitro (Gallie et at, 1987a; 1987b; Sleat et at, 1987; Sleat et at, 1988). Electroporation of tobacco mesophyll protoplasts with transcripts containing the TMV leader fused to reporter genes CAT, GUS, and LUC produced a 33-, 21-, and 36-fold level of enhancement, respectively (Gallie et at, 1987a; 1987b; Gallie et at, 1991). Also in tobacco, an 83-nt 5'-UTL of potato virus X RNA was shown to enhance expression of the neomycin phosphotranserese II (NptII) 4-fold (Poogin and Skryabin, 1992).

The effect of a 5'-UTL may be different depending on the plant, particularly between dicots and monocots. The TMV 5'-UTL has been shown to be more effective in tobacco protoplasts (Gallie et al., 1989) than in maize protoplasts (Gallie and Young, 1994). Also, the 5'-UTLs from TMV-Ω (Gallie et al., 1988), AMV-coat (Gehrke et at, 1983; Jobling and Gehrke, 1987), TMV-coat (Goelet et al., 1982), and BMV-coat (French et at, 1986) worked poorly in maize and inhibited expression of a luciferase gene in maize relative to its native leader (Koziel et at, 1996). However, the 5'-UTLs from the cauliflower mosaic virus (CaMV) 35-transcript and the maize genes glutelin (Boronat et al., 1986), PEP-carboxylase (Hudspeth and Grula, 1989) and ribulose biphosphate carboxylase showed a considerable increase in expression of the luciferase gene in maize relative to its native leader (Koziel et at, 1996).

These 5'-UTLs had different effects in tobacco. In contrast to maize, the TMV Ω 5'-UTL and the AMV coat protein 5'-UTL enhanced expression in tobacco, whereas the glutelin, maize PEP-carboxylase and maize ribulose-1,5-bisphosphate carboxylase 5'-UTLs did not show enhancement relative to the native luciferase 5'-UTL (Koziel et al., 1996). Only the CaMV 35S 5'-UTL enhanced luciferase expression in both maize and tobacco (Koziel et al., 1996). Furthermore, the TMV and BMV coat protein 5'-UTLs were inhibitory in both maize and tobacco protoplasts (Koziel et al., 1996).

4.15.2 Use of Introns to Increase Expression

Including one or more introns in the transcribed portion of a gene has been found to increase heterologous gene expression in a variety of plant systems (Callis et al., 1987; Maas et al., 1991; Mascerenhas et al., 1990; McElroy et al., 1990; Vasil et al., 1989), although not all introns produce a stimulatory effect and the degree of stimulation varies. The enhancing effect of introns appears to be more apparent in monocots than in dicots. Tanaka et al., (1990) has shown that use of the catalase intron 1 isolated from castor beans increases gene expression in rice. Likewise, the first intron of the alcohol dehydrogenase 1 (Adh1) has been shown to increase expression of a genomic clone of Adh1 comprising the endogenous promoter in transformed maize cells (Callis et al., 1987; Dennis et al., 1984). Other introns that are also able to increase expression of transgenes which contain them include the introns 2 and 6 of Adh1 (Luehrsen and Walbot, 1991), the catalase intron (Tanaka et al., 1990), intron 1 of the maize bronze 1 gene (Callis et al., 1987), the maize sucrose synthase intron 1 (Vasil et al., 1989), intron 3 of the rice actin gene (Luehrsen and Walbot, 1991), rice actin intron 1 (McElroy et al., 1990), and the maize ubiquitin exon 1 (Christensen et al., 1992).

Generally, to achieve optimal expression, the selected intron(s) should be present in the 5' transcriptional unit in the correct orientation with respect to the splice junction sequences (Callis et al., 1987; Maas et al., 1991; Mascerenhas et al., 1990; Oard et al., 1989; Tanaka et al., 1990; Vasil et al., 1989). Intron 9 of Adh1 has been shown to increase expression of a heterologous gene when placed 3' (or downstream of) the gene of interest (Callis et al., 1987).

4.15.3 Use of Synthetic Genes to Increase Expression of Heterologous Genes in Plants When introducing a prokaryotic gene into a eukaryotic host, or when expressing a eukaryotic gene in a non-native host, the sequence of the gene must often be altered or modified to allow efficient translation of the transcript(s) derived form the gene. Significant experience in using synthetic genes to increase expression of a desired protein has been achieved in the expression of *Bacillus thuringiensis* in plants. Native *B. thuringiensis* genes are often expressed only at low levels in dicots and sometimes not at all in many species of monocots (Koziel et al., 1996). Codon usage in the native genes is considerably different from that found in typical plant genes, which have a higher G+C content. Strategies to increase expression of these genes in plants generally alter the overall G+C content of the genes. For example, synthetic *B. thuringiensis* crystal-protein encoding genes have resulted in significant improvements in expression of these endotoxins in various crops including cotton (Perlak et al., 1990; Wilson et al., 1992), tomato (Perlak et al., 1991), potato (Perlak et al., 1993), rice (Cheng et al., 1998), and maize (Koziel et al., 1993).

In a similar fashion the inventors contemplate that the genetic constructs of the present invention, because they contain one or more genes of bacterial origin, may in certain circumstances be altered to increase the expression of these prokaryotic-derived genes in particular eukaryotic host cells and/or transgenic plants which comprise such constructs. Using molecular biology techniques which are well-known to those of skill in the art, one may alter the coding or non coding sequences of the particular CryET70-encoding gene sequences to optimize or facilitate its expression in transformed plant cells at levels suitable for preventing or reducing insect infestation or attack in such transgenic plants.

4.15.4 Chloroplast Sequestering and Targeting

Another approach for increasing expression of A+T rich genes in plants has been demonstrated in tobacco chloroplast transformation. High levels of expression of an unmodified *Bacillus thuringiensis* crystal protein-encoding genes in tobacco has been reported by McBride et al., (1995).

Additionally, methods of targeting proteins to the chloroplast have been developed. This technique, utilizing the pea chloroplast transit peptide, has been used to target the enzymes of the polyhydroxybutyrate synthesis pathway to the chloroplast (Nawrath et al., 1994). Also, this technique negated the necessity of modification of the coding region other than to add an appropriate targeting sequence.

U.S. Pat. No. 5,576,198 (specifically incorporated herein by reference) discloses compositions and methods useful for genetic engineering of plant cells to provide a method of controlling the timing or tissue pattern of expression of foreign DNA sequences inserted into the plant plastid genome. Constructs include those for nuclear transformation which provide for expression of a viral single subunit RNA polymerase in plant tissues, and targeting of the expressed polymerase protein into plant cell plastids. Also included are plastid expression constructs comprising a viral gene promoter region which is specific to the RNA polymerase expressed from the nuclear expression constructs described above and a heterologous gene of interest to be expressed in the transformed plastid cells.

4.15.5 Effects of 3' Regions on Transgene Expression

The 3'-end regions of transgenes have been found to have a large effect on transgene expression in plants (Ingelbrecht et al., 1989). In this study, different 3' ends were operably linked to the neomycin phosphotransferase II (NptII) reporter gene and expressed in transgenic tobacco. The different 3' ends used were obtained from the octopine synthase gene, the 2S seed protein from *Arabidopsis*, the small subunit of rbcS from *Arabidopsis*, extension form carrot, and chalcone synthase from *Antirrhinum*. In stable tobacco transformants, there was about a 60-fold difference between the best-expressing construct (small subunit rbcS 3' end) and the lowest expressing construct (shalcone synthase 3' end).

TABLE 6

PLANT PROMOTERS

| Promoter | Reference[a] |
|---|---|
| Viral | |
| Figwort Mosaic Virus (FMV) | U.S. Pat. No. 5,378,619 |
| Cauliflower Mosaic Virus (CaMV) | U.S. Pat. No. 5,530,196 |
| | U.S. Pat. No. 5,097,025 |
| | U.S. Pat. No. 5,110,732 |
| Plant | |
| Elongation Factor | U.S. Pat. No. 5,177,011 |
| Tomato Polygalacturonase | U.S. Pat. No. 5,442,052 |
| Arabidopsis Histone H4 | U.S. Pat. No. 5,491,288 |
| Phaseolin | U.S. Pat. No. 5,504,200 |
| Group 2 | U.S. Pat. No. 5,608,144 |
| Ubiquitin | U.S. Pat. No. 5,614,399 |
| P119 | U.S. Pat. No. 5,633,440 |
| α-amylase | U.S. Pat. No. 5,712,112 |
| Viral enhancer/Plant promoter | |
| CaMV 35Senhancer/mannopine synthase promoter | U.S. Pat. No. 5,106,739 |

[a]Each reference is specifically incorporated herein by reference in its entirety.

TABLE 7

TISSUE SPECIFIC PLANT PROMOTERS

| Tissue Specific Promoter | Tissue(s) | Reference[a] |
|---|---|---|
| Blec | epidermis | U.S. Pat. No. 5,646,333 |
| malate synthase | seeds; seedlings | U.S. Pat. No. 5,689,040 |
| isocitrate lyase | seeds; seedlings | U.S. Pat. No. 5,689,040 |
| patatin | tuber | U.S. Pat. No. 5,436,393 |
| ZRP2 | root | U.S. Pat. No. 5,633,363 |
| ZRP2(2.0) | root | U.S. Pat. No. 5,633,363 |
| ZRP2(1.0) | root | U.S. Pat. No. 5,633,363 |
| RB7 | root | U.S. Pat. No. 5,459,252 |
|  | root | U.S. Pat. No. 5,401,836 |
|  | fruit | U.S. Pat. No. 4,943,674 |
|  | meristem | U.S. Pat. No. 5,589,583 |
|  | guard cell | U.S. Pat. No. 5,538,879 |
|  | stamen | U.S. Pat. No. 5,589,610 |
| SodA1 | pollen; middle layer; stomium of anthers | Van Camp et al., 1996 |
| SodA2 | vasular bundles; stomata; axillary buds; pericycle; stomium; pollen | Van Camp et al., 1996 |
| CHS15 | flowers; root tips | Faktor et al., 1996 |
| Psam-1 | phloem tissue; cortex; root tips | Vander et al., 1996 |
| ACT11 | elongating tissues and organs; pollen; ovules | Huang et al., 1997 |
| zmGBS | pollen; endosperm | Russell and Fromm, 1997 |
| zmZ27 | endosperm | Russell and Fromm, 1997 |
| osAGP | endosperm | Russell and Fromm, 1997 |
| osGT1 | endosperm | Russell and Fromm, 1997 |
| RolC | phloem tissue; bundle sheath; vascular parenchyma | Graham et al., 1997 |
| Sh | phloem tissue | Graham et al., 1997 |
| CMd | endosperm | Grosset et al., 1997 |
| Bnm1 | pollen | Treacy et al., 1997 |
| rice tungro bacilliform virus | phloem | Yin et al., 1997a; 1997b |
| S2-RNase | pollen | Ficker et al., 1998 |
| LeB4 | seeds | Baumlein et al., 1991 |
| gf-2.8 | seeds; seedlings | Berna and Bernier, 1997 |

[a]Each reference is specifically incorporated herein by reference in its entirety.

The ability to express genes in a tissue specific manner in plants has led to the production of male and female sterile plants. Generally, the production of male sterile plants involves the use of anther-specific promoters operably linked to heterologous genes that disrupt pollen formation (U.S. Pat. Nos. 5,689,051; 5,689,049; 5,659,124, each specifically incorporated herein by reference). U.S. Pat. No. 5,633,441 (specifically incorporated herein by reference) discloses a method of producing plants with female genetic sterility. The method comprises the use of style-cell, stigma-cell, or style- and stigma-cell specific promoters that express polypeptides that, when produced in the cells of the plant, kills or significantly disturbs the metabolism, functioning or development of the cells.

TABLE 8

INDUCIBLE PLANT PROMOTERS

| Promoter | Reference[a] |
|---|---|
| heat shock promoter | U.S. Pat. No. 5,447,858 |
| Em | U.S. Pat. No. 5,139,954 |
| Adh1 | Kyozoka et al., 1991 |
| HMG2 | U.S. Pat. No. 5,689,056 |
| cinnamyl alcohol dehydrogenase | U.S. Pat. No. 5,633,439 |
| asparagine synthase | U.S. Pat. No. 5,595,896 |
| GST-II-27 | U.S. Pat. No. 5,589,614 |

[a]Each reference is specifically incorporated herein by reference in its entirety.

4.16 Peptide Nucleic Acid Compositions

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNAs are able to be utilized in a number of methods that traditionally have used RNAs or DNAs. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference.

4.16.1 Methods of Making PNAs

According to Corey, PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Further discussed by Corey are desired modifications of PNAs for given applications. Modifications can be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Rusckowski et al., 1997). U.S. Pat. No. 5,700,922 discusses PNA-DNA-PNA chimeric molecules and their uses in diagnostics, modulating protein in organisms, and treatment of conditions susceptible to therapeutics.

4.16.2 Physical Properties of PNAs

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al., (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al., have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11-13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

4.16.3 Applications of PNAs

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al., (1993b), Hanvey et al., (1992), and Good and Nielsen (1997). Koppelhus et al., (1997) have used PNAs to inhibit HIV-1 inverse transcription, showing that PNAs may be used for antiviral therapies.

Methods of characterizing the antisense binding properties of PNAs are discussed in Rose (1993) and Jensen et al., (1997). Rose uses capillary gel electrophoresis to determine binding of PNAs to their complementary oligonucleotide, measuring the relative binding kinetics and stoichiometry. Similar types of measurements were made by Jensen et al., using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

4.17 Antibody Compositions and Methods of Making

In particular embodiments, the inventors contemplate the use of antibodies, either monoclonal or polyclonal which bind to one or more of the polypeptides disclosed herein. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and tittering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, (Gefter et al., 1977). The use of electrically induced fusion methods is also appropriate (Goding, 1986, pp. 71-74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.18 ELISAs and Immunoprecipitation

ELISAs may be used in conjunction with the invention. In an ELISA assay, proteins or peptides incorporating crystal protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hr at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-crystal protein antibodies of the present invention are particularly useful for the isolation of other crystal protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

4.19 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.20 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 9.

TABLE 9

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation of B. thuringiensis EG4140

Crop dust samples were obtained from various sources throughout the U.S. and abroad, typically grain storage facilities. The crop dust samples were treated and spread on agar plates to isolate individual Bacillus-type colonies as described (Donovan et al., 1992). EG4140 is a wild-type B thuringiensis strain isolated from a crop dust sample from Pennsylvania. Phase contrast microscopy was used to visually examine the morphology of parasporal crystals produced by the bacterial colonies from this crop dust. The colony designated EG4140 contained endospores and crystalline inclusions of a unique morphology resembling spindles. The complement of native plasmids contained within isolated B. thuringiensis EG4140 was determined by modified Eckhardt agarose gel electrophoresis as described by Gonzalez et al. (1982). The pattern of native plasmids did not correspond to patterns of typical known serovars (Gonzalez and Carlton, 1984). The plasmid sizes are approximately 110 MDa, 80 MDa and 33 MDa.

5.2 Example 2

Bioassay Evaluation of B. thuringiensis Strains for Toxicity Towards Coleopteran Insects A three-tiered bioassay scheme was adopted to identify B. thuringiensis strains with toxicity towards larvae of the coleopteran insect Diabrotica virgifera virgifera (Western corn rootworm, WCRW). Because WCRW larvae are delicate, bioassays with this insect are time-consuming and frequently result in high control mortalities. To limit the number of WCRW bioassays that needed to be performed, coleopteran-toxic B. thuringiensis strains were first identified by performing bioassay screens against larvae of the Colorado potato beetle (Leptinotarsa decemlineata, CPB), an insect that shows greater sensitivity than WCRW to coleopteran-toxic B. thuringiensis Cry proteins. Strains with CPB-toxicity were further prioritized by performing bioassay screens against larvae of the coleopteran insect Diabrotica undecempunctat howardii (Southern corn rootworm, SCRW), a closely related species of rootworm that is hardier and easier to bioassay than the WCRW. B. thuringiensis strains exhibiting toxicity towards SCRW and/or CPB larvae were evaluated in bioassays against the WCRW. In this manner, several hundred B. thuringiensis strains were screened in bioassay and strains exhibiting WCRW-toxicity were identified. Strain EG4096, a wild-type B. thuringiensis strain that produces a coleopteran-toxic protein, CryET29, was used as a positive-control in these bioassays.

B. thuringiensis strains were grown in C2 medium (Donovan et al., 1988) at 25° C. for four days at which time sporulation and lysis had occurred. The sporulated cultures were used directly in screens against CPB. For SCRW and WCRW bioassays, the cultures were harvested by centrifugation, washed in approximately 2.5 times the original volume with water, and resuspended in 0.005% Triton X-100® at one-tenth the original culture volume. The spore-crystal suspensions were used directly in bioassay.

Insecticidal activity against CPB and SCRW larvae was determined via a surface contamination assay on an artificial diet in a plastic feeding cup (175 mm$^2$ surface) as described by Rupar et al. (1991). All bioassays were performed using 128-well trays containing approximately 1 ml of diet per well with perforated mylar sheet covers (C-D International Inc., Pitman, N.J.). A first instar larva was placed in each cup and scored for mortality after 3-5 days (CPB) or 7 days (SCRW). Thirty-two larvae were tested per bioassay screen at 50 ul of a spore-crystal suspension per well of diet.

Bioassay screens against WCRW larvae were performed via a surface contamination assay using an artificial diet (20 g agar, 50 g wheat germ, 39 g sucrose, 32 g casein, 14 g fiber, 9 g Wesson salts mix, 1 g methyl paraben, 0.5 g sorbic acid, 0.06 g cholesterol, 9 g Vaderzant's vitamin mix, 0.5 ml linseed oil, 2.5 ml phosphoric/propionic acid per liter). A first instar larva was placed in each diet cup and scored for mortality after 7 days.

A sporulated and lysed culture of strain EG4140 exhibited toxicity towards CPB larvae in a bioassay screen. Subsequently, the strain was screened in bioassay against SCRW larvae and exhibited little, if any, toxicity. Nevertheless, the strain was screened in bioassay against WCRW larvae and was found to exhibit significant insecticidal activity (Table 10). EG4140 also showed toxicity towards larvae of the lepidopteran pest, *Plutella xylostella*.

TABLE 10

INSECTICIDAL ACTIVITY OF STRAIN EG4140 TO WCRW LARVAE

| Sample | % Mortality |
| --- | --- |
| EG4140 | 100% |
| EG4096 | 100% |
| Control | 31% |

Dose: EG4096 - 31 µg/well
EG4140 - 38 µg/well

5.3 Example 3

Characterization of the CryET70 Polypeptide

EG4140 was grown in C2 (Donovan et al., 1988) medium for four days at 25° C. during which time the culture grew to stationary phase, sporulated and lysed, thus releasing the protein inclusions into the medium. Two hundred microliters of the culture were added to one milliliter of 1M NaCl, 1 mM EDTA, pH 8 and centrifuged to pellet the spores and crystals. The pellet was resuspended in water at one-half the original volume.

Crystal protein was solubilized by incubating the spore-crystal suspension in a SDS solubilization buffer at 100° C. for 5 min and size fractionated by SDS-polyacrylamide gel electrophoresis (SDS-PAGE) (Laemmli, 1970). After size fractionation, the proteins were visualized by Coomassie Brilliant Blue R-250 staining. This analysis showed that the major crystal protein present in the sporulated culture of EG4140 is approximately 86 kDa in size. This novel protein was designated CryET70. Additional proteins of 39 kDa, 34 kDa, and 32 kDa are also produced by this strain.

To further characterize CryET70, the $NH_2$-terminal amino acid sequence of the protein was determined. A sporulated culture of EG4140 was washed in water and resuspended at the original volume in water. The proteins were size fractionated by SDS-PAGE following the protocol described by Brussock and Currier (1990). The procedure was modified to eliminate the neutralization step with 3M HEPES. After electrophoresis the proteins were transferred to a Immobilon-P membrane (Millipore, Bedford, Mass.) following standard Western blotting procedures (Towbin et al., 1979). After transfer, the membrane was rinsed four times in $dH_2O$ and washed in 0.025% Coomassie Blue R-250, 40% methanol. The filter was destained in 50% methanol and rinsed 4× in $dH_2O$. The portion of the filter containing the approximately 86-kDa protein band was excised with a razor blade.

The determination of the $NH_2$-terminal amino acid sequence of the purified CryET70 polypeptide immobilized on the membrane was performed in the Department of Physiology at the Tufts Medical School, Boston, Mass. using standard automated Edman degradation procedures. The $NH_2$-terminal sequence was determined to be:

```
 1   2   3   4   5   6   7
Ala Ser Asp Tyr Ile Asp Ile      (SEQ ID NO:3)
 8   9  10  11  12  13
Arg Ser Ile Phe Gln Thr
```

The FASTA algorithm (Lipman and Pearson, 1985) in the PCGene program (Intelligenetics, Mountain View, Calif.) was used to compare the N-terminal sequence of the CryET70 polypeptide with amino acid sequences of all *B. thuringiensis* crystal proteins of which the inventors were aware of at the time, including the sequences of all *B. thuringiensis* crystal proteins which had been published in the scientific literature, international patent applications or issued patents. The N-terminal sequence of the CryET70 polypeptide was not found to be similar to sequences of the known *B. thuringiensis* crystal proteins.

5.4 Example 4

Cloning of the cryET70 Gene

Total DNA was extracted from EG4140 by the following procedure. Vegetative cells were resuspended in a lysis buffer containing 50 mM glucose, 25 mM Tris-HCl (pH8.0), 10 mM EDTA, and 4 mg/ml lysozyme. The suspension was incubated at 37° C. for one hr. Following incubation, SDS was added to 1%. The suspension was then extracted with an equal volume of phenol:chloroform:isoamyl alcohol (50:48:2). DNA was precipitated from the aqueous phase by the addition of one-tenth volume 3 M sodium acetate, and two volumes of 100% ethanol. The precipitated DNA was collected with a glass rod, washed with 70% ethanol, and resuspended in $dH_2O$.

The DNA was partially digested with the restriction endonuclease MboI and size fractionated on a 0.6% agarose gel in 1X TAE overnight at 2 V/cm. The gel was stained with ethidium bromide so that the digested DNA could be visualized when exposed to long-wave UV light. Gel slices containing DNA fragments between about 9 and about 12 kb in size were excised from the gel with a razor blade. The DNA was extracted from the gel using the GENECLEAN II® kit (BIO 101 Inc., La Jolla, Calif.) and eluted in $H_2O$.

To create a library in *E. coli*, the 9- to 12-kb MboI restriction fragments of DNA from EG4140 were ligated into the *E. coli/B. thuringiensis* shuttle vector pHT315 (Arantes and Lereclus, 1991). The vector pHT315 can replicate in *E. coli* and carries the gene for resistance to the antibiotic ampicillin, which may be used as a selectable marker. The vector pHT315 can also replicate at a high copy number in *B. thuringiensis*, and carries the gene for resistance to the antibiotic erythromycin, which may be used as a selectable marker in this organism. The fragments from EG4140 were ligated with pHT315 which had been digested with BamHI and treated with calf intestine alkaline phosphatase (Boehringer Mannheim, Indianapolis, Ind.) to remove the terminal 5' phosphates from the digested plasmid, thereby preventing re-ligation of the vector to itself. T4 ligase and a ligation buffer (Promega Corporation, Madison, Wis.) were added to the reaction containing the digested pHT315 and the MboI fragments. These were incubated at room temperature for several hours to allow the insertion and ligation of the MboI fragments into the pHT315 vector DNA.

The ligation mixture described above was used to transform electroporation-competent SURE™ cells (Stratagene, La Jolla, Calif.) to ampicillin resistance following procedures described by the manufacturer. Aliquots of the transformed cells were frozen at −70° C. in LB (Maniatis et al., 1982) containing 15% glycerol. The transformed *E. coli* cells were later thawed and plated on LB agar plates containing 50 μg/ml ampicillin and incubated overnight at 37° C. The growth of ampicillin-resistant colonies indicated the presence of a recombinant plasmid in the cells of each colony.

To isolate the colonies harboring the cloned fragments that contain the cryET70 gene sequences, the transformed *E. coli* colonies were first transferred to nitrocellulose filters. This was accomplished by placing a circular filter (Millipore HATF 085 25, Millipore Corp., Bedford, Mass.) directly on top of the LB-ampicillin agar plates containing the transformed colonies. When the filter is slowly peeled off of the plate the colonies stick to the filter giving an exact replica of the pattern of colonies from the original plate. Enough cells from each colony are left on the plate that five to six hr of growth at 37° C. will restore the colonies. The plates are then stored at 4° C. until needed. The nitrocellulose filters with the transferred colonies were then placed, colony-side up, on fresh LB-ampicillin agar plates and allowed to grow at 37° C. until they reached a size of approximately 1 mm in diameter.

To release the DNA from the recombinant *E. coli* cells onto the nitrocellulose filter, the filters were placed, colony-side up, on Whatman 3 MM Chromatography paper (Whatman International LTD., Maidstone, England) soaked with 0.5 N NaOH, 1.5 M NaCl for 15 min. The filters were then neutralized by placing the filters, colony-side up, on Whatman paper soaked with 1 M $NH_4$-acetate, 0.02 M NaOH for 10 min. The filters were then rinsed in 3×SSC, 0.1% SDS, air dried, and baked for one hr at 80° C. in a vacuum oven to prepare them for hybridization.

In order to identify the gene encoding the CryET70 polypeptide, an oligonucleotide probe specific for the $NH_2$-terminal amino acid sequence of the protein was designed using codons typically found in *B. thuringiensis* toxin genes. The following oligonucleotide, designated AM24, was synthesized by Integrated DNA Technologies, Inc. (Coralville, Iowa):

```
                                       (SEQ ID NO:4)
5'-GCITCIGATTATATTGATATTAGATCAATTTTTCAAAC-3'
```

The $NH_2$-terminal oligonucleotide specific for the cryET70 gene, AM24, was labeled at the 5' end with γ-$^{32}$P and used as a hybridization probe. To radioactively label the probe, 40 pmoles AM24 were added to a reaction (20 μl total volume) containing [γ-$^{32}$P]ATP (3 μl of 3,000 Ci/mmole at 10 mCi/ml), 2 μl of a 10× reaction buffer (700 mM Tris-HCl, pH7.8, 100 mM $MgCl_2$, 50 mM DTT), and 10 units T4 polynucleotide kinase (Promega Corporation, Madison, Wis.). The reaction was incubated for 20 min at 37° C. to allow the transfer of the radioactive phosphate to the 5' end of the oligonucleotide, thus making it useful as a hybridization probe.

The labeled probe was added to the filters in 3×SSC, 0.1% SDS, 10× Denhardt's reagent (0.2% bovine serum albumin (BSA), 0.2% polyvinylpyrrolidone, 0.2% Ficoll®), 0.2 mg/ml heparin and incubated overnight at 37° C. These conditions were chosen to allow hybridization of the labeled oligonucleotide to related sequences present on the nitrocellulose blots of the transformed *E. coli* colonies. Following the incubation, the filters were washed in three changes of 3×SSC, 0.1% SDS at 40° C. The filters were blotted dry and exposed to Kodak X-OMAT AR X-ray film (Eastman Kodak Company, Rochester, N.Y.) overnight at −70° C. with an intensifying screen (Fisher Biotech, Pittsburgh, Pa.).

Several colonies hybridized to AM24. These colonies were identified by lining up the signals on the autoradiogram with the colonies on the original transformation plates. The isolated colonies were then grown in LB-ampicillin liquid medium from which the cells could be harvested and recombinant plasmid prepared by the standard alkaline-lysis miniprep procedure (described in Maniatis et al., 1982). The isolated plasmids were digested with the restriction endonuclease EcoRI. The DNA from these plasmid digests were resolved by agarose gel electrophoresis and transferred to an Immobilon-NC nitrocellulose filter (Millipore Corp., Bedford, Mass.) according to the method of Southern (1975). DNA was fixed to the filter by baking at 80° C. in a vacuum oven.

Subsequently, the blot was hybridized with the oligonucleotide, AM24, that had been radioactively labeled at the 5' end with γ-$^{32}$P using T4 polynucleotide kinase. EcoRI fragments from five of the 16 plasmids hybridized to the probe, confirming the presence of a cryET70 gene in those clones. One of the plasmids containing a cryET70 gene was designated pEG1648 (FIG. 1). The *E. coli* strain containing pEG1648 was designated EG11841.

5.5 Example 5

Sequencing of the cryET70 Gene and Determination of the Encoded Amino Acid Sequence A partial DNA sequence of the gene cloned on pEG1648 was determined following established dideoxy chain-termination DNA sequencing procedures (Sanger et al., 1977). Preparation of the double stranded plasmid template DNA was accomplished using a Wizard® SV Miniprep Kit (Promega, Madison, Wis.) following the manufacturer's procedures or a Qiagen Plasmid Kit (Qiagen Inc., Chatsworth, Calif.) following the manufacturer's procedures, followed by a phenol: chloroform: isoamyl alcohol (50:48:2) extraction and then a chlorform:isoamyl alcohol (24:1) extraction. The sequencing reactions were performed using the Sequenase™ Version 2.0 DNA Sequencing Kit (United States Biochemical/Amersham Life Science Inc., Cleveland, Ohio) following the manufacturer's procedures and using $^{35}$S-DATP as the labeling isotope (obtained from DuPont NEN® Research Products, Boston, Mass.). Denaturing gel electrophoresis of the reactions was performed on a 6% (wt./vol.) acrylamide, 42% (wt./vol.) urea sequencing gel or on a CastAway™ Precast 6% acrylamide sequencing gel (Stratagene, La Jolla, Calif.). The dried gel was exposed to Kodak X-OMAT AR X-ray film (Eastman Kodak Company, Rochester, N.Y.) overnight at room temperature.

The $NH_2$-terminal specific oligonucleotide AM24 was used as the initial sequencing primer. A partial DNA sequence for the cryET70 gene on pEG1648 was obtained by using the procedures described above. Successive oligonucleotides to be used for priming sequencing reactions were designed from the sequencing data of the previous set of reactions. An approximately 5.8 kb EcoRI-HindIII fragment containing the entire cryET70 gene was subcloned from pEG1648 into pUC18. This plasmid, designated pEG1657 (FIG. 1) was used to complete the cryET70 sequence using automated sequencing. Five hundred nanograms of purified plasmid was added to 100 ng of primer in a total volume of 20 µl. All the primers were designed using the OLIGO primer analysis software (National Biosciences, Inc., Minnesota). DNA samples were sequenced using the ABI PRISM DyeDeoxy sequencing chemistry kit (Applied Biosystems, CA) according to the manufacturer's suggested protocol. The completed reactions were run on as ABI377 automated DNA sequencer. Overlapping DNA sequence fragments were analyzed and assembled using Sequencher v2.1 DNA analysis software (Gene Codes Corporation, Michigan). The DNA sequence of cryET170 is shown in Section 5.5.1 (SEQ ID NO:1). The protein coding region begins at nucleotide 92. The deduced amino acid sequence of the CryET70 polypeptide is shown in Section 5.5.1 (SEQ ID NO:2).

5.5.1 DNA SEQUENCE OF THE CRYET70 GENE (SEQ ID NO:1)

```
GTAATAGTAGTTATTTAGCAGGAATAAAAGGGAGGGTATCGAATACTTTCAAATGAAGAC
TGAAAATTTACAAATAGAAGGAGAGAAAAGTATGAAAGATTCAATTTCAAAGGGATATGA
TGAAATAACAGTGCAGGCAAGTGATTATATTGATATTCGCTCAATTTTTCAAACGAATGG
ATCTGCAACATTTAATTCAACCACTAATATTACAACTTTAACGCAAGCTACAAATAGTCA
AGCGGGAGCAATTGCAGGGAAGACAGCTTTAGATATGAGACATGATTTTACTTTTAGAGC
TGATATTTTTCTTGGAACTAAAAGTAATGGAGCAGATGGTATTGCGATAGCATTTCATAG
AGGATCAATTGGTTTTGTTGGGGAGAAGGGTGGAGGACTTGGGATTTTAGGCGCCCTAAA
AGGTATAGGATTTGAATTAGACACATATGCGAATGCTCCTCAAGATGAACAAGGAGATTC
TTTTGGACATGGAGCAATGAGAGGCCTATTCCCTGGTTTCCCAAATGGATATCCACATGC
TGGTTTTGTAAGTACGGATAAAAATAGAGGTTGGTTATCTGCCTTAGCTCAGATGCAGCG
AATAGCTGCTCCAAATGGGCGTTGGAGACGTCTGGCGATTCATTGGGATGCTCGCAATAA
AAAATTAACTGCAAACCTTGAGGATTTAACTTTTAATGATTCAACGGTATTAGTGAAACC
ACGTACTCCAAGATATGCAAGATGGGAGTTATCAAATCCTGCATTTGAACTTGATCAAAA
GTATACTTTTGTTATTGGTTCAGCGACGGGTGCATCTAATAACCTACATCAGATTGGTAT
TATAGAATTTGATGCATACTTTACTAAACCGACAATAGAGGCGAATAATGTAAGTGTTCC
GGTGGGAGCAACATTTAATCCGAAAACATATCCAGGAATAAATTTAAGAGCAACTGATGA
AATAGATGGTGATTTGACATCTGAAATTATTGTGACAGATAATAATGTTAATACGTCGAA
ATCTGGTGTGTATAATGTGACGTATTATGTAAAGAATAGCTATGGGAAAGTGATGAAAA
AACAATCGAAGTAACTGTGTTTTCAAACCCTACAATTATTGCAAGTGATGTTGAAATTGA
AAAAGGTGAATCGTTTAATCCATTAACAGACTCAAGAGTGAGGCTGTCTGCACAAGATTC
ATTGGGTAATGATATTACTTCAAAAGTAAAGGTGAAATCAAGTAATGTGGATACTTCGAA
ACCAGGTGAATATGATGTTGTGTTTGAAGTGACCGATAATTTTGGTGGGAAAGCAGAAAA
AGAAATCAAGGTTACAGTTTTAGGGCAGCCAAGTATTGAAGCGAATGATGTTGAATTAGA
AATAGGTGATTTATTTAATCCGTTAACAGATTCACAAGTAGGCCTTCGTGCAAAAGACTC
ATTAGGCAAAGATATTACGAATGATGTGAAAGTAAAGTCAAGTAATGTGGATACTTCAAA
ACCAGGAGAATATGAAGTTGTATTTGAAGTGACCGATCGTTTTGGAAAAAAAGCAGAAAA
AAGTATCAAAGTCCTTGTTCTAGGAGAACCAAGCATTGAAGCAAATAATGTTGAGATTGA
AAAAGACGAAAGGTTCGATCCATTAACAGATTCAAGAGTAGGTCTCCGTGCAAAAGACTC
ATTAGGCAAAGATATTACGAATGATGTGAAAGTAAAATCAAGTAATGTGGATACTTCAAA
ACCAGGAGAATATGAAGTTGTATTTGAAGTGACTGATCGTTTTGGTAAATATGTAAAGAA
ATTGATTGTAGTTATAGTACCAGTAATTGATGATGAATGGGAAGATGGAAATGTGAATGG
ATGGAAATTCTATGCGGGGCAAGACATCACACTGTTGAAAGATCCTGAAAAAGCATATAA
AGGAGAATATGTATTCTATGATTCTAGGCATGCTGCTATTTCTAAAACAATCCCAGTAAC
AGATTTACAAGTGGGAGGGAATTATGAAATTACAGTATATGTTAAAGCAGAAAGCGGTGA
```

```
-continued
TCATCACCTAAAAGTGACGTACAAGAAAGACCCGAAAGGTCCGGAGGAACCACCAGTTTT

CAATAGACTTATTAGTACAGGGAAATTGGTGGAAAAAGACTATAGAGAATTAAAAGGAAC

ATTCCGTGTAACGGAATTAAACCAAGCACCATTGATAATCGTAGAGAATTTTGGTGCTGG

ATATATAGGTGGAATTAGAATTGTGAAAATATCGTAATAAAAACAGATAAAATAGAGAGA

GGAACGCTGGATAGCGTTCCTCTTTTCAGTTTAGTGTACCATCTCCAGGTCCAGTTCATT

TTTT 5.5.2 AMINO ACID SEQUENCE OF THE CRYET70 POLYPEPTIDE
MKDSISKGYDEITVQASDYIDIRSIFQTNGSATFNSTTNITTLTQATNSQ

AGAIAGKTALDMRHDFTFRADIFLGTKSNGADGIAIAFHRGSIGFVGEKG

GGLGILGALKGIGFELDTYANAPQDEQGDSFGHGAMRGLFPGFPNGYPHA

GFVSTDKNRGWLSALAQMQRIAAPNGRWRRLAIHWDARNKKLTANLEDLT

FNDSTVLVKPRTPRYARWELSNPAFELDQKYTFVIGSATGASNNLHQIGI

IEFDAYFTKPTIEANNVSVPVGATFNPKTYPGINLRATDEIDGDLTSEII

VTDNNVNTSKSGVYNVTYYVKNSYGESDEKTIEVTVFSNPTIIASDVEIE

KGESFNPLTDSRVRLSAQDSLGNDITSKVKVKSSNVDTSKPGEYDVVFEV

TDNFGGKAEKEIKVTVLGQPSIEANDVELEIGDLFNPLTDSQVGLBAKDS

LGKDITNDVKVKSSNVDTSKPGEYEVVFEVTDRFGKKAEKSIKVLVLGEP

SIEANNVEIEKDERFDPLTDSRVGLRAKDSLGKDITNDVKVKSSNVDTSK

PGEYEVVFEVTDRFGKYVKKLIVVIVPVIDDEWEDGNVNGWKFYAGQDIT

LLKDPEKAYKGEYVFYDSRHAAISKTIPVTDLQVGGNYEITVYVKAESGD

HHLKVTYKKDPKGPEEPPVFNRLISTGKLVEKDYRELKGTFRVTELNQAP

LIIVENFGAGYIGGIRIVKIS
```

5.6 Example 6

Analysis of Sequence Homologies to cryET70/cryET70 Sequences

Database searches were conducted to determine if the amino acid sequence of the CryET70 polypeptide shares identity with the sequences of other characterized proteins, especially other insecticidal proteins. Database searches using on-line servers were performed using the amino acid sequence of CryET70 with the BLASTP program (Altschul et al., 1990) provided by the National Center for Biotechnology Information (Bethesda, Md.). The BLASTP searches were run with the BLOSUM62 matrix. The searched database consisted of non-redundant GenBank CDS translations plus the PDB, SwissProt, SPupdate, and PIR databases.

Only one protein in these databases was identified with any significant similarity to CryET70. Cry22, a hymenopteran toxic protein from B. thuringiensis PS211B2 identified as SEQ ID NO:51 of U.S. Pat. No. 5,596,071 (specifically incorporated herein by reference), showed 88.9% sequence identity to CryET70.

A B. thuringiensis toxins database (which includes all toxin genes and proteins published to date) was searched for proteins with homology to CryET70 using the FASTA algorithm (Lipman and Pearson, 1985) in the PCGene program (Intelligenetics, Mountain View, Calif.). Again, only Cry22 showed significant sequence identity to CryET70.

5.7 Example 7

Expression of Recombinant CryET70 Polypeptide

To characterize the properties of the CryET70 polypeptide, it was necessary to express the cloned cryET70 gene in a B. thuringiensis stain that does not produce other crystal proteins (i.e. a Cry⁻ strain). The plasmid containing the cloned cryET70 gene, pEG1648, contains a B. thuringiensis origin of replication as well as an origin that directs replication in E. coli, as described above. The plasmid, pEG1648, was used to transform the Cry⁻ B. thuringiensis strain EG10650 to erythromycin resistance ($Em^R$) by electroporation (Macaluso and Mettus, 1991). Cells transformed to $Em^R$ were selected by incubation overnight on LB agar plates containing 25 μg/ml erythromycin. One $Em^R$ colony from each transformation was selected for further analysis. One isolate was designated EG11839.

EG11839 was grown in C2 medium containing 25 μg/ml erythromycin for four days at 25° C., at which point sporulation and cell lysis had occurred. Microscopic examination of the sporulated cultures demonstrated that the recombinant strain was producing large, dark, spindle-shaped crystalline inclusions. These crystals resemble the crystals produced by the wild-type strain EG4140, indicating that the cryET70 gene in the recombinant strain EG11839 is a functional gene capable of directing the expression of the CryET70 polypeptide.

The sporulated culture of EG11839 was harvested by centrifugation, washed, and resuspended at one-tenth the original volume in $H_2O$. The crystal protein in the suspension was characterized by SDS-PAGE analysis which revealed the production of an approximately 86-kDa protein.

5.8 Example 8

Toxicity of CryET70 to Insects

The toxicity of CryET70 polypeptide towards WCRW larvae (*Diabrotica virgifera virgifera*) was determined.

EG11839 was grown in C2 medium at 25° C. for four days until sporulation and cell lysis had occurred. The culture was harvested by centrifugation, washed in approximately 2.5 times the original volume with $H_2O$, and resuspended in 0.005% Triton X-100® at one-tenth the original volume. For comparison with EG11839, a recombinant *B. thuringiensis* strain, EG11204, producing the coleopteran-toxic protein Cry3Bb (Donovan et al., 1992) was grown and harvested in the same manner. Toxin proteins from the samples were quantified by SDS-PAGE as described by Brussock and Currier (1990). The procedure was modified to eliminate the neutralization step with 3M HEPES.

WCRW larvae were bioassayed via surface contamination of an artificial diet (20 g agar, 50 g wheatgerm, 39 g sucrose, 32 g casein, 14 g fiber, 9 g Wesson salts mix, 1 g methyl paraben, 0.5 g sorbic acid, 0.06 g cholesterol, 9 g Vanderzant's vitanin mix, 0.5 ml linseed oil, 2.5 ml phosphoric/propionic acid per 1 liter). Each bioassay of EG11839 (CryET70) and EG11204 (Cry3Bb) consisted of eight serial aqueous dilutions with aliquots applied to the surface of the diet. After the diluent (an aqueous 0.005% Triton X-100® solution) had dried, first instar larvae were placed on the diet and incubated at 28° C. Thirty-two larvae were tested per dose. Mortality was scored after seven days. Data from replicated bioassays were pooled for probit analysis (Daum, 1970) with mortality being corrected for control death, the control being diluent only (Abbott, 1925). Results are reported as the amount of crystal protein per well (175 $mm^2$ of diet surface) resulting in an $LC_{50}$, the concentration killing 50% of the test insects. 95% confidence intervals are also reported for the $LC_{50}$ values (Table 11).

TABLE 11

INSECTICIDAL ACTIVITY
OF THE CRYET70 PROTEIN TO WCRW LARVAE

| Sample | Crystal Protein | $LC_{50}$ (μg protein/well) | 95% C.I. | $LC_{95}$ (μg protein/well) |
|---|---|---|---|---|
| EG11839 | CryET70 | 8.4 | 6-11 | 69 |
| EG11204 | Cry3Bb | 11.4 | 3-23 | 437 |

Control mortality 12.5%

The results shown in Table 11 demonstrate that the CryET70 polypeptide has significant activity on larvae of the western corn rootworm. CryET70 is at least as active as Cry3Bb.

A spore-crystal suspension of EG11839, prepared as described in Example 2, was screened for activity against lepidopteran insects. EG2001, the Cry1-containing strain HD1, was assayed as a control. EG2001 was grown in C2 medium as described in Example 2, washed and resuspended in an original volume of 0.005% Triton X-100®. EG11839 exhibited no significant activity against *Agrotis ipsilon*, *Heliothis virescens*, *Helicoverpa zea*, *Ostrinia nubilalis*, *Spodoptera exigua*, *Spodoptera frugiperda*, *Diabroica umdecimpunctata howardi*, and *Leptinotarsa decemlineata*. EG11839 exhibited some activity against *Plutella xylostella* and *Trichoplusia ni* (Table 12).

TABLE 12

INSECTICIDAL ACTIVITY OF EG11839
AGAINST *P. XYLOSTELLA* AND *T. NI*

| Sample | *P. xylostella* (% mortality) | *T. ni* (% mortality) |
|---|---|---|
| EG11839* | 31 | 40 |
| EG2001** | 25 | 81 |

*Dose - 10,000 nl/well
**Dose - 10 nl/well

Thus, CryET70 exhibits toxicity towards larvae of both coleopteran and lepidopteran species.

CryET70 is 88.9% homologous to Cry22. The *Eschericia coli* strain NRRL B-21150, containing the plasmid pMYC2371 that carries the cry22 gene, was obtained from the USDA-ARS, Patent Culture Collection (Peoria, Ill.). The plasmid was isolated using the Wizard® SV Miniprep Kit (Promega, Madison, Wis.), and the plasmid DNA was used to transform BT EG10650 to $Em^R$. The resulting strain is EG11860. EG11860 and EG11839 were grown as described in Example 2, and screened against WCRW as described above. The results are shown in Table 13.

TABLE 13

INSECTICIDAL ACTIVITY OF CRYET70
AND CRY22 AGAINST WCRW

| | % Mortality | |
|---|---|---|
| Sample | 20 μg/well | 200 μg/well |
| EG11839 (CryET70) | 81.5 | 100 |
| EG11860 (Cry22) | 0 | 18.5 |

CryET70 exhibits significant toxicity towards the WCRW, while Cry22 does not. The differences in sequence between CryET70 and Cry22 impart WCRW activity on CryET70.

An alignment of the CryET70 and Cry22Aa amino acid sequences revealed that the amino acid sequence differences are not localized to a particular region, but are scattered throughout the length of the two proteins. Nevertheless, several regions of dissimilarity are notable. For instance, the amino terminal sequences of the two proteins from positions 3-8 are completely different. In addition, Cry22Aa contains an extra alanine residue at position 17. The CryET70 sequence from residues 506-516 shows only 45% sequence identity with the homologous sequence 507-517 in Cry22Aa Using the ANTIGEN program [based on the method of Hopp and Woods (1981)] in the PC/GENE sequence analysis package, the CryET70 sequence from 508-514 was determined to be significantly more hydrophilic than the homologous Cry22A sequence. Since hydrophilic regions tend to be localized at the surface of globular proteins and, consequently, may be involved in interactions with other molecules, this hydrophilic region may be important in determining the differences in insecticidal activity noted between CryET70 and Cry22Aa. Using the SOAP program [based on the method of Kyle and Doolittle (1982)], in the PC/GENE sequence analysis package, the hydropathy indices for CryET70 and Cry22Aa could be compared. The two proteins showed apparent differences in hydrophobicity at the amino terminus, near residue Q124 in CryET70, near residues 506-516 in ET70, near residues 569-573 in CryET70, and near residue K662 in CryET70. These regions represent targets for future investigations. For instance, each unique CryET70 region could be systematically introduced into the cry22Aa gene by in vitro mutagenesis to identify those regions that can confer WCRW toxicity on Cry22Aa.

5.9 Example 9

Additional Strains with Sequences Related to cryET70

To date, 26 wild-type strains have been identified with sequences related to cryET70. These strains were identified by colony blot hybridization experiments using a cryET70-specific hybridization probe. Wild-type strains were patched onto LB plates and incubated at 30° C. for four hr. A Nytran® Maximum-Strength Plus (Schleicher and Schuell, Keene, N.H.) circular (82 mm) membrane filter was then placed on the plates and the plates and filters were incubated at 25° C. overnight. The filters, which contained an exact replica of the patches, were then placed on fresh LB plates, and the filters and the original plates were incubated at 30° C. for 4 hr to allow for growth of the colonies. After four hr, filters were denatured, neutralized, washed, and baked as described in Example 4.

Primers were designed based on the cryET70 sequence.

```
AM34:
5'-GACATGATTTTACTTTTAGAGC-3'    (SEQ ID NO:5)

AM43:
5'-CATCACTTTCCCCATAGC-3'        (SEQ ID NO:6)
```

A PCR™ with primers AM 34 and AM 43 was used to amplify a cryET70 fragment from pEG1648 DNA. This PCR™ product was labeled with [$\alpha$-$^{32}$P]dATP using the Prime-a-Gene® kit (Promega Corporation, Madison, Wis.) to generate a cryET70-specific probe. Hybridizations were performed as described in Example 4 with the exception that the hybridization temperature was 63° C. Filters were washed in 1×SSC, 0.1% SDS at 63° C. Hybridizing colonies were detected by autoradiography using Kodak X-OMAT AR X-ray film. The strains identified by colony blot hybridization are listed in Table 14.

5.10 Example 10

Production of Antibody to CryET70

CryET70 polypeptide was prepared for antibody production so that CryET70 antibodies could be used to identify CryET70-related proteins. EG11839 was grown in C2 medium for four days at 25° C. The culture was washed in 2.5× volume H$_2$O and resuspended at 1/20 the original volume in 0.005% Triton X-100®. The spore-crystal suspension was then loaded on a sucrose step gradient consisting of 79%, 72% and 55% sucrose. The gradient was spun overnight in a Beckman SW28 at 18,000 rpm. CryET70 crystals banded between the 79% and the 72% sucrose layers. The CryET70 crystals were washed several times in H$_2$O and resuspended in 0.005% Triton X-100®. The purified crystals were then solubilized in 50 mM sodium carbonate (pH 10), 5 mM DTT, and any contaminating vegetative cells or spores were removed by centrifugation. The supernatant was neutralized with boric acid to pH8.4, and the solubilized crystals were sent to Rockland Laboratories (Gilbertsville, Pa.) for antibody production in rabbits according to standard procedures. The rabbits received two intradermal injections on days zero and seven with 50% CryET70 polypeptide in sterile phosphate buffered saline, 50% complete Freund's adjuvant. Two additional boosts were given subcutaneously on days 14 and 28 before a test bleed on day 38. Two hundred fifty µg of CryET70 were used per rabbit for the initial injection, and 125 µg of CryET70 were used per rabbit for the subsequent boosts. On day 56 the rabbits were boosted again, as before, prior to a production bleed on day 71. The final boost was with 160 µg CryET70 on day 80, followed by a termination bleed on day 90.

5.11 Example 11

Analysis of Strains Containing cryET70-Related Sequences

Strains identified in Example 9 as containing sequences related to cryET70 were screened in bioassay against WCRW as described in Example 2. In addition, the strains were examined further by Southern and Western blot analyses.

Total DNA was prepared from the strains as described in Example 4. Total DNA was digested with EcoRI and separated on a 0.8% agarose gel in TAE buffer (40 mM Tris-acetate, 2 mM Na$_2$EDTA, pH 8). The DNA was blotted onto an Immobilon-NC nitrocellulose filter (Millipore Corp., Bedford, Mass.) according to the method of Southern (1975). DNA was fixed to the filter by baking at 80° C. in a vacuum oven.

The blot was then hybridized with the cryET70-specific probe described in Example 9. Hybridizations were performed as in Example 4 with the exception that the hybridization and wash temperature was 60° C. Strains containing hybridizing DNA fragments are listed in Table 14.

For the Western blot analysis, proteins from 10-fold concentrated cultures of the strains were run on a 10% SDS-polyacrylamide gel (Owl Separation Systems, Woburn, Mass.). Twenty µl of culture was added to 10 µl of 3× Laemmli buffer and heated at 100° C. for five minutes. Fifteen µl were loaded per lane. Following electrophoresis, the gel was blotted to nitrocellulose following standard Western blotting procedures (Towbin et al., 1979). The filter was blocked with TBSN (10 mM Tris, pH 7.8, 0.9% NaCl, 0.1% globulin-free BSA, 0.03% NaN$_3$)+2% BSA. The filter was then washed with TBSN twice and then incubated with a 1/1,000 dilution of anti-CryET70 in TBSN. The filter was washed in TBSN after incubation with antibody and then incubated with the sheep anti-rabbit IgG conjugated with alkaline phosphatase (1/1,000 dilution in TBSN). After washing in TBSN, the proteins antigenically related to CryET70 were detected with ImmunoPure® NBT/BCIP Substrate Kit (Pierce, Rockford, Ill.). The results of the Southern blot, Western blot, and bioassay analyses are shown in Table 14.

TABLE 14

STRAINS CONTAINING CRYET70-RELATED GENES

| Strains | Southern blot | Western blot | % Control WCRW |
|---|---|---|---|
| EG2929 | + | + | 26 |
| EG3218 | + | − | 30 |
| EG3221 | + | − | 63 |
| EG3303 | + | − | 15 |
| EG3304 | + | − | 0 |
| EG3707 | + | − | 45 |

TABLE 14-continued

STRAINS CONTAINING CRYET70-RELATED GENES

| Strains | Southern blot | Western blot | % Control WCRW |
|---|---|---|---|
| EG3803 | – | | 0 |
| EG3953 | + | | 100 |
| EG3966 | + | – | 7 |
| EG4113 | – | – | 40 |
| EG4135 | + | + | 45 |
| EG4150 | – | – | 64 |
| EG4268 | – | + | 46 |
| EG4375 | | – | 100 |
| EG4447 | + | | 0 |
| EG4448 | + | – | 100 |
| EG4503 | + | – | 56 |
| EG4541 | + | – | 72 |
| EG4580 | + | + | 33 |
| EG4640 | – | – | 95 |
| EG4737 | – | – | 72 |
| EG4741 | + | – | 73 |
| EG5233 | – | – | 52 |
| EG5366 | + | – | 69 |
| EG5370 | – | – | 16 |
| EG5422 | | – | 8 |

The above data indicate that there is a family of cryET70-related genes, some of which encode CryET70-related proteins that have activity against WCRW. Related proteins may be found with increased activity against WCRW or with an expanded spectrum of insecticidal activity.

5.12 Example 12

Isolation of Transgenic Plants

5.12.1 Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., U.S. Pat. No. 5,463,175, specifically incorporated herein by reference).

The particular promoter selected should be capable of causing sufficient expression of the enzyme coding sequence to result in the production of an effective amount of protein. One set of preferred promoters are constitutive promoters such as the CaMV35S or FMV35S promoters that yield high levels of expression in most plant organs (U.S. Pat. No. 5,378,619, specifically incorporated herein by reference). Another set of preferred promoters are root enhanced or specific promoters such as the CaMV derived 4 as-1 promoter or the wheat POX1 promoter (U.S. Pat. No. 5,023,179, specifically incorporated herein by reference; Hertig et al., 1991). The root enhanced or specific promoters would be particularly preferred for the control of corn rootworm (*Diabroticus* spp.) in transgenic corn plants.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eucaryotic genes, or from a synthetic gene sequence. The present invention is not limited to constructs wherein the non-translated region is derived from the 5' non-translated sequence that accompanies the promoter sequence.

For optimized expression in monocotyledenous plants such as maize, an intron should also be included in the DNA expression construct. This intron would typically be placed near the 5' end of the mRNA in untranslated sequence. This intron could be obtained from, but not limited to, a set of introns consisting of the maize hsp70 intron (U.S. Pat. No. 5,424,412; specifically incorporated herein by reference) or the rice Act1 intron (McElroy et al., 1990). As shown below, the maize hsp70 intron is useful in the present invention.

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of *Agrobacterium* tumor-inducing (Ti) plasmid genes, such as the nopaline synthase (NOS) gene and (2) plant genes such as the pea ssRUBISCO E9 gene (Fischhoff et al., 1987).

5.12.2 Plant Transformation and Expression

A transgene containing a structural coding sequence of the present invention can be inserted into the genome of a plant by any suitable method such as those detailed herein. Suitable plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. Publ. No. EP0120516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990).

5.12.3 Construction of Plant Expression Vectors for cryET70 Transgenes

For efficient expression of the polynucleotides disclosed herein in transgenic plants, the selected sequence region encoding the insecticidal polypeptide must have a suitable sequence composition (Diehn et al., 1996).

To place a cry gene in a vector suitable for expression in monocotyledonous plants (i.e. under control of the enhanced Cauliflower Mosaic Virus 35S promoter and link to the hsp70 intron followed by a nopaline synthase polyadenylation site as in U.S. Pat. No. 5,424,412, specifically incorporated herein by reference), the vector is digested with appropriate enzymes such as NcoI and EcoRI. The larger vector band of approximately 4.6 kb is then electrophoresed, purified, and ligated with T4 DNA ligase to the appropriate restriction fragment containing the plantized cry gene. The ligation mix is then transformed into E. coli, carbenicillin resistant colonies recovered and plasmid DNA recovered by DNA miniprep procedures. The DNA may then be subjected to restriction endonuclease analysis with enzymes such as NcoI and EcoRI (together), NotI, and PstI to identify clones containing the cry gene coding sequence fused to the hsp70 intron under control of the enhanced CaMV35S promoter).

To place the gene in a vector suitable for recovery of stably transformed and insect resistant plants, the restriction fragment from pMON33708 containing the lysine oxidase coding sequence fused to the hsp70 intron under control of the enhanced CaMV35S promoter may be isolated by gel electrophoresis and purification. This fragment can then be ligated with a vector such as pMON30460 treated with NotI and calf intestinal alkaline phosphatase (pMON30460 contains the neomycin phosphotransferase coding sequence under control of the CaMV35S promoter). Kanamycin resistant colonies may then be obtained by transformation of this ligation mix into E. coli and colonies containing the resulting plasmid can be identified by restriction endonuclease digestion of plasmid miniprep DNAs. Restriction enzymes such as NotI, EcoRV, HindIII, NcoI, EcoRI, and BglII can be used to identify the appropriate clones containing the restriction fragment properly inserted in the corresponding site of pMON30460, in the orientation such that both genes are in tandem (i.e. the 3' end of the cry gene expression cassette is linked to the 5' end of the nptII expression cassette). Expression of the CryET70 polypeptide by the resulting vector is then confirmed in plant protoplasts by electroporation of the vector into protoplasts followed by protein blot and ELISA analysis. This vector can be introduced into the genomic DNA of plant embryos such as maize by particle gun bombardment followed by paromomycin selection to obtain corn plants expressing the cry gene essentially as described in U.S. Pat. No. 5,424,412, specifically incorporated herein by reference. In this example, the vector was introduced via cobombardment with a hygromycin resistance conferring plasmid into immature embryo scutella (IES) of maize, followed by hygromycin selection, and regeneration. Transgenic corn lines expressing the CryET70 polypeptide are then identified by ELISA analysis. Progeny seed from these events are then subsequently tested for protection from susceptible insect feeding.

5.13 Example 13

Modification OF cryET70 Genes for Expression in Plants

Many wild-type genes encoding bacterial crystal proteins are known to be expressed poorly in plants as a full-length gene or as a truncated gene. Typically, the G+C content of a cry gene is low (37%) and often contains many A+T rich regions, potential polyadenylation sites and numerous ATTTA sequences. Table 15 shows a list of potential polyadenylation sequences which should be avoided when preparing the "plantized" gene construct.

TABLE 15

LIST OF SEQUENCES OF POTENTIAL POLYADENYLATION SIGNALS

| | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.
All others are potential minor plant polyadenylation sites.

The regions for mutagenesis may be selected in the following manner. All regions of the DNA sequence of the cry gene are identified which contained five or more consecutive base pairs which were A or T. These were ranked in terms of length and highest percentage of A+T in the surrounding sequence over a 20-30 base pair region. The DNA is analysed for regions which might contain polyadenylation sites or ATTTA sequences. Oligonucleotides are then designed which maximize the elimination of A+T consecutive regions which contained one or more polyadenylation sites or ATTTA sequences. Two potential plant polyadenylation sites have been shown to be more critical based on published reports. Codons are selected which increase G+C content, but do not generate restriction sites for enzymes useful for cloning and assembly of the modified gene (e.g., BamHI, BglII, SacI, NcoI, EcoRV, etc.). Likewise condons are avoided which contain the doublets TA or GC which have been reported to be infrequently-found codons in plants.

Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it is often advantageous to increase the expression of crystal proteins in these tissues over that obtained with the CaMV35S promoter.

The 35S promoter of Figwort Mosaic Virus (FMV) is analogous to the CaMV35S promoter. This promoter has been isolated and engineered into a plant transformation vector. Relative to the CaMV promoter, the FMV 35S promoter is highly expressed in the floral tissue, while still providing similar high levels of gene expression in other tissues such as leaf. A plant transformation vector, may be constructed in which the full length synthetic cry gene is driven by the FMV 35S promoter. Tobacco plants may be transformed with the vector and compared for expression of the crystal protein by Western blot or ELISA immunoassay in leaf and floral tissue. The FMV promoter has been used to produce relatively high levels of crystal protein in floral tissue compared to the CaMV promoter.

5.14 Example 14

Expression of Synthetic Cry Genes with ssRUBISCO Promoters and Chloroplast Transit Peptides The genes in plants encoding the small subunit of RUBISCO(SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of heterologous genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of crystal proteins to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express the protein of the present invention in only a subset of plant tissues, if for example expression of such a protein in certain cells was found to be deleterious to those cells. For example, for control of Colorado potato beetle in potato, it may be advantageous to use SSU promoters to direct crystal protein expression to the leaves but not to the edible tubers.

Utilizing SSU CTP sequences to localize crystal proteins to the chloroplast might also be advantageous. Localization of the *B. thuringiensis* crystal proteins to the chloroplast could protect these from proteases found in the cytoplasm. This could stabilize the proteins and lead to higher levels of accumulation of active toxin. cry genes containing the CTP may be used in combination with the SSU promoter or with other promoters such as CaMV35S.

5.15 Example 15

Targeting of CryET70 Polypeptides to the Extracellular Space or Vacuole Using Signal Peptides The *B. thuringiensis* polypeptides described here are primarily localized to the cytoplasm of the plant cell, and this cytoplasmic localization results in plants that are insecticidally effective. However, in certain embodiments, it may be advantageous to direct the *B. thuringiensis* polypeptide to other compartments of the plant cell. Localizing *B. thuringiensis* proteins in compartments other than the cytoplasm may result in less exposure of the *B. thuringiensis* proteins to cytoplasmic proteases leading to greater accumulation of the protein yielding enhanced insecticidal activity. Extracellular localization could lead to more efficient exposure of certain insects to the *B. thuringiensis* proteins leading to greater efficacy. If a *B. thuringiensis* protein were found to be deleterious to plant cell function, then localization to a noncytoplasmic compartment could protect these cells from the protein.

In plants as well as other eukaryotes, proteins that are destined to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes through the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct *B. thuringiensis* proteins out of the cytoplasm is to fuse the genes for synthetic *B. thuringiensis* genes to DNA sequences encoding known plant signal peptides. These fusion genes will give rise to *B. thuringiensis* proteins that enter the secretory pathway, and lead to extracellular secretion or targeting to the vacuole or other compartments.

Signal sequences for several plant genes have been described. One such sequence is for the tobacco pathogenesis related protein PR1b has been previously described (Cornelissen et al., 1986). The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the β-subunit of the 7S storage protein of common bean (*Phaseolus vulgaris*), PvuB has been described (Doyle et al., 1986). Based on the published these published sequences, genes may be synthesized chemically using oligonucleotides that encode the signal peptides for PR1b and PvuB. In some cases to achieve secretion or compartmentalization of heterologous proteins, it may be necessary to include some amino acid sequence beyond the normal cleavage site of the signal peptide. This may be necessary to insure proper cleavage of the signal peptide.

6.0 REFERENCES

The following references, to the extent that they provide exemplary procedural or other details supplementary to those set forth herein, are specifically incorporated herein by reference:

U.S. Pat. No. 4,196,265, issued Apr. 1, 1980.
U.S. Pat. No. 4,237,224, issued Dec. 2, 1980.

U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,769,061, issued Sep. 6, 1988.
U.S. Pat. No. 4,800,159, issued Jan. 24, 1989.
U.S. Pat. No. 4,883,750, issued Nov. 28, 1989.
U.S. Pat. No. 4,940,835, issued Feb. 23, 1990.
U.S. Pat. No. 4,943,674, issued Jul. 24, 1990.
U.S. Pat. No. 4,965,188, issued Oct. 23, 1990.
U.S. Pat. No. 4,971,908, issued Nov. 20, 1990.
U.S. Pat. No. 4,987,071, issued Jan. 22, 1991.
U.S. Pat. No. 5,097,025, issued Mar. 17, 1992.
U.S. Pat. No. 5,106,739, issued Apr. 21, 1992.
U.S. Pat. No. 5,110,732, issued May 5, 1992.
U.S. Pat. No. 5,139,954, issued Aug. 19, 1992.
U.S. Pat. No. 5,176,995, issued Oct. 15, 1991.
U.S. Pat. No. 5,177,011, issued Jan. 5, 1993.
U.S. Pat. No. 5,334,711, issued Aug. 2, 1994.
U.S. Pat. No. 5,378,619, issued Jan. 3, 1995.
U.S. Pat. No. 5,384,253, issued Jan. 24, 1995.
U.S. Pat. No. 5,401,836, issued May 28, 1995.
U.S. Pat. No. 5,436,393, issued Jul. 25, 1995.
U.S. Pat. No. 5,442,052, issued Aug. 15, 1995.
U.S. Pat. No. 5,447,858, issued Sep. 5, 1995.
U.S. Pat. No. 5,459,252, issued Oct. 17, 1995.
U.S. Pat. No. 5,491,288, issued Feb. 13, 1996.
U.S. Pat. No. 5,504,200, issued Apr. 2, 1996.
U.S. Pat. No. 5,530,196, issued Jun. 25, 1996.
U.S. Pat. No. 5,538,879, issued Jul. 23, 1996.
U.S. Pat. No. 5,576,198, issued Nov. 19, 1996.
U.S. Pat. No. 5,589,583, issued Dec. 31, 1996.
U.S. Pat. No. 5,589,610, issued Dec. 31, 1996.
U.S. Pat. No. 5,595,896, issued Jan. 21, 1997.
U.S. Pat. No. 5,596,071, issued Jan. 21, 1997.
U.S. Pat. No. 5,608,144, issued Mar. 4, 1997.
U.S. Pat. No. 5,614,399, issued Mar. 25, 1997.
U.S. Pat. No. 5,631,359, issued May 20, 1997.
U.S. Pat. No. 5,633,363, issued May 27, 1997.
U.S. Pat. No. 5,633,439, issued May 27, 1997.
U.S. Pat. No. 5,633,440, issued May 27, 1997.
U.S. Pat. No. 5,633,441, issued May 27, 1997.
U.S. Pat. No. 5,646,333, issued Jul. 8, 1997.
U.S. Pat. No. 5,659,124, issued Aug. 19, 1997.
U.S. Pat. No. 5,689,040, issued Nov. 18, 1997.
U.S. Pat. No. 5,689,049, issued Nov. 18, 1997.
U.S. Pat. No. 5,689,051, issued Nov. 18, 1997.
U.S. Pat. No. 5,689,056, issued Nov. 18, 1997.
U.S. Pat. No. 5,700,922, issued Dec. 23, 1997.
U.S. Pat. No. 5,712,112, issued Jan. 27, 1998.
Int. Pat. Appl. Publ. No. PCT/US87/00880.
Int. Pat. Appl. Publ. No. PCT/US89/01025.
Int. Pat. Appl. Publ. No. WO 84/02913.
Int. Pat. Appl. Publ. No. WO 88/10315.
Int. Pat. Appl. Publ. No. WO 89/06700.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Int. Pat. Appl. Publ. No. WO 98/13497.
Eur. Pat. Appl. Publ. No. EP0360257.
Eur. Pat. Appl. Publ. No. EP 320,308.
Eur. Pat. Appl. Publ. No. EP 329,822.
Eur. Pat. Appl. Publ. No. 92110298.4
Great Britain Pat. Appl. Publ. No. GB 2,202,328.

Abdullah et al., *Biotechnology*, 4:1087, 1986.

Abbott, "A method for computing the effectiveness of an insecticide," *J. Econ. Entomol.*, 18:265-267, 1925.

Adelman, Hayflick, Vasser, Seeburg, "In vitro deletion mutagenesis for bacterial production of the 20,000-dalton form of human pituitary growth hormone," *DNA*, 2(3):183-193, 1983.

Allen and Choun, "Large unilamellar liposomes with low uptake into the reticuloendothelial system," *FEBS Lett.*, 223:42-46, 1987.

Altschul, Gish, Miller, Myers, Lipman, "Basic local alignment search tool," *J. Mol. Biol.*, 215(3):403-410, 1990.

Armitage, Ly, Koch, Frydenlund, Orum, Batz, Schuster, "Peptide nucleic acid-DNA duplexes: long range hole migration from an internally linked antrhaquinone," *Proc. Natl. Acad. Sci. USA*, 94(23):12320-12325, 1997.

Arvidson, Dunn, Strnad, Aronson, "Specificity of *Bacillus thuringiensis* for lepidopteran larvae: factors involved in vivo and in the structure of a purified protoxin," *Mol. Microbiol.*, 3(11):1533-1534, 1989.

Baum, Coyle, Gilbert, Jany, Gawron-Burke, "Novel cloning vectors for *Bacillus thuringiensis*," *Appl. Environ. Microbiol.*, 56(11):3420-3428, 1990.

Baumlein, Boerjan, Nagy, Panitz, Inze, Wobus, "Upstream sequences regulating legumin gene expression in heterologous transgenic plants," *Mol. Gen. Genet.*, 225(1):121-128, 1991.

Benbrook et al., In: *Proceedings Bio Expo* 1986, Butterworth, Stoneham, Mass., pp. 27-54, 1986.

Berhnard, *FEMS Microbiol. Lett.*, 33:261-265, 1986.

Berna and Bernier, "Regulated expression of a wheat germin gene in tobacco: oxalate oxidase activity and apoplastic localization of the heterologous protein," *Plant Mol. Biol.*, 33(3):417-429, 1997.

Boffa, Carpaneto, Allfrey, "Isolation of active genes containing CAG repeats by DNA strand invasion by a peptide nucleic acid," *Proc. Natl. Acad. Sci. USA*, 92(6):1901-1905, 1995.

Boffa, Morris, Carpaneto, Louissaint, Allfrey, "Invasion of the CAG triplet repeats by a complementary peptide nucleic acid inhibits transcription of the androgen receptor and TATA-binding protein genes and correlates with refolding of an active ncleosome containing a unique AR gene sequence," *J. Biol. Chem.*, 271(22):13228-13233, 1996.

Bolivar, Rodriguez, Greene, Betlach, Heyneker, Boyer, "Construction and characterization of new cloning vehicles. II. A multipurpose cloning system," *Gene*, 2(2): 95-113, 1977.

Boronat, Martinez, Reina, Puigdomenech, Palau, "Isolation and sequencing of a 28 kd gluteline-2 gene from maize: Common elements in the 5' flanking regions among zein and glutelin genes," *Plant Sci.*, 47:95-102, 1986.

Brown and Whiteley, "Molecular characterization of two novel crystal protein genes from *Bacillus thuringiensis* susp. thompsoni," *J. Bacteriol.*, 174(2):549-557, 1992.

Brussock and Currier, "Use of sodium dodecyl sulfate-polacryamide gel electrophoresis to quantify *Bacillus thuringiensis* δ-endotoxins," In: *Analytical Chemistry of Bacillus thuringiensis*, L. A. Hickle and W. L. Fitch, (Eds), American Chemical Society, Washington D.C., pp. 78-87, 1990.

Callis, Fromm, Walbot, "Introns increase gene expression in cultured maize cells," *Genes Devel.*, 1:1183-1200, 1987.

Campbell, *In: Monoclonal Antibody Technology, Laboratory Techniques in Biochemistry and Molecular Biology*, Vol. 13, Burden and Von Knippenberg, (Eds.) Elsevier, Amsterdam, pp 75-83, 1984.

Capecchi, "High efficiency transformation by direct microinjection of DNA into cultured mammalian cells," *Cell*, 22(2):479-488, 1980.

Carlsson, Jonsson, Norden, Bulay, Zare, Noolandi, Nielsen, Tsui, Zielenski, "Screening for genetic mutations," *Nature*, 380(6571):207, 1996.

Cashmore et al., *In: Gen. Eng. of Plants*, Plenum Press, New York, pp 29-38, 1983.

Cech, Zaug, Grabowski, "In vitro splicing of the ribosomal RNA precursor of Tetrahymena: involvement of a guanosine nucleotide in the excision of the intervening sequence," *Cell*, 27(3 Pt 2):487-496, 1981.

Chambers, Jelen, Gilbert, Jany, Johnson, Gawron-Burke, *J. Bacteriol.*, 173(13):3966-3976, 1991.

Chau, Tobias, Bachmair, Marriott, Ecker, Gonda, Varshavsky, "A multiubiquitin chain is confined to specific lysine in a targeted short-lived protein," *Science*, 243(4898):1576-1583, 1989.

Chen, Banerjea, Harmison, Haglund, Schubert, "Multitarget-ribozyme directed to cleave at up to nine highly conserved HIV-1 env RNA regions inhibits HIV-1 replication—potential effectiveness against most presently sequenced HIV-1 isolates," *Nucl. Acids Res.*, 20(17):4581-4589, 1992.

Cheng, Sardana, Kaplan, Altosaar, "*Agrobacterium*-transformed rice plants expressing synthetic cryIA(b) and cryIA(c) genes are highly toxic to striped stem borer and yellow stem borer," *Proc. Natl. Acad. Sci. USA*, 95(6):2767-2772, 1998.

Chowrira and Burke, "Extensive phosphorothioate substitution yields highly active and nuclease-resistant hairpin ribozymes," *Nucl. Acids Res.*, 20(11):2835-2840, 1992.

Christensen, Fitzpatrick, Gildea, Petersen, Hansen, Koch, Egholm, Buchardt, Nielsen, Coull et al., *J. Pept. Sci.*, 1(3):175-183, 1995.

Christensen, Sharrock, Quail, "Maize polyubiquitin genes: Structure, thermal perturbation of expression and transcript splicing, and promoter activity following transfer to protoplasts by electroporation," *Plant Mol. Biol.*, 18:675-689, 1992.

Clapp, "Somatic gene therapy into hematopoietic cells. Current status and future implications," *Clin. Perinatol.*, 20(1):155-168, 1993.

Collins and Olive, "Reaction conditions and kinetics of self-cleavage of a ribozyme derived from *Neurospora* VS RNA," *Biochemistry*, 32(11):2795-2799, 1993.

Conway and Wickens, *In: RNA Processing*, Cold Spring Harbor Laboratory, Cold Spring Harbor, N.Y., p 40, 1988.

Corey, "Peptide nucleic acids: expanding the scope of nucleic acid recognition," *Trends Biotechnol.*, 15(6):224-229, 1997.

Couvreur et al., "Nanocapsules, a new lysosomotropic carrier," *FEBS Lett.*, 84:323-326, 1977.

Couvreur, "Polyalkyleyanoacrylates as colloidal drug carriers," *Crit. Rev. Ther. Drug Carrier Syst.*, 5:1-20, 1988.

Crickmore et al., *Abstr. 28th Annu. Meet. Soc. Invert. Pathol.*, Cornell University, Ithaca, N.Y., 1995.

Cristou et al., *Plant Physiol.*, 87:671-674, 1988.

Curiel, Agarwal, Wagner, Cotten, "Adenovirus enhancement of transferrin-polylysine-mediated gene delivery," *Proc. Natl. Acad. Sci. USA*, 88(19):8850-8854, 1991.

Curiel, Wagner, Cotten, Birnstiel, Agarwal, Li, Loechel, and Hu, "High-efficiency gene transfer mediated by adenovirus coupled to DNA-polylysine complexes," *Hum. Gen. Ther.*, 3(2):147-154, 1992.

Daum, "Revision of two computer programs for probit analysis," *Bull. Entomol. Soc. Amer.*, 16:10-15, 1970.

de Barjac, *In: Microbial Control of Pests and Plant Diseases*, H. D. Burges (Ed.), Academic Press, London, pp 36-43, 1981.

Dean, Tamaki, Dunsmuir, Favreau, Katayama, Dooner, Bedbrook, "mRNA transcripts of several plant genes are polyadenylated multiple sites in vivo," *Nucl. Acids Res.*, 14(5):2229-2240, 1986.

Dennis, Gerlach, Pryor, Bennetzen, Inglis, Llewellyn, Sachs, Ferl, Peackocock, "Molecular analysis of the alcohol dehydrogenase (Adh1) gene of maize," *Nucl. Acids Res.*, 12:3983-4000, 1984.

Dhir, Dhir, Hepburn, Widholm, "Factors affecting transient gene expression in electroporated Glycine-max protoplasts," *Plant Cell Rep.*, 10(2):106-110, 1991a.

Dhir, Dhir, Sturtevant, Widholm, "Regeneration of transformed shoots for electroporated soybean *Glycine max* L. Merr. Protoplasts, *Plant Cell Rep.*, 10(2):97-101, 1991b.

Donovan, Rupar, Slaney, Malvar, Gawron-Burke, Johnson, "Characterization of two genes encoding *Bacillus thuringiensis* insecticidal crystal proteins toxic to Coleoptera species," *Appl. Environ. Microbiol.*, 58(12):3921-3927, 1992.

Donovan, Gonzalez Jr., Gilbert, Dankocsik, "Isolation and characterization of EG2158, a new strain of *Bacillus thuringiensis* toxic to coleopteran larvae, and nucleotide sequence of the toxin gene," *Mol. Gen. Genet.*, 214(3):365-372, 1988.

Dropulic, Lin, Martin, Jeang, "Functional characterization of a U5 ribozyme: intracellular suppression of human immunodeficiency virus type 1 expression," *J. Virol.*, 66(3):1432-1441, 1992.

Dueholm et al., *J. Org. Chem.*, 59:5767-5773, 1994.

Egholm, Buchardt, Christensen, Behrens, Freier, Driver, Berg, Kim, Norden, Nielsen, "PNA hybridizes to complementary oligonucleotides obeying the Watson-Crick hydrogen-bonding rules," *Nature*, 365(6446):566-568, 1993.

Eglitis and Anderson, "Retroviral vectors for introduction of genes into mammalian cells," *Biotechniques*, 6(7):608-614, 1988.

Eglitis, Kantoff, Kohn, Karson, Moen, Lothrop, Blaese, Anderson, "Retroviral-mediated gene transfer into hemopoietic cells," *Avd. Exp. Med Biol.*, 241:19-27, 1988.

Eichenlaub, "Mutants of the mini-F plasmid pML31 thermosensitive in replication," *J. Bacteriol.*, 138(2):559-566, 1979.

Elroy-Stein and Moss, "Cytoplasmic expression system based on constitutive synthesis of bacteriophage T7 RNA polymerase in mammalian cells," *Proc. Natl. Acad. Sci. USA*, 87(17):6743-6747, 1990.

English and Slatin, *Insect Biochem. Mol. Biol.*, 22:1-7, 1992.

Faktor, Kooter, Dixon, Lamb, "Functional dissection of a bean chalcone synthase gene promoter in transgenic tobacco plants reveals sequence motifs essential for floral expression," *Plant Mol. Biol.*, 32(5):849-859, 1996.

Ficker, Kirch, Eijlander, Jacobsen, Thompson, "Multiple elements of the S2-RNase promoter from potato (*Solanum tuberosum* L.) are required for cell type-specific expression in transgenic potato and tobacco," *Mol. Gen. Genet.*, 257 (2):132-142, 1998.

Fiers, Contreras, haegemann, Rogiers, Van de Voorde, Van Heuverswyn, Van Herreweghe, Volckaert, Ysebaert, "Complete nucleotide sequence of SV40 DNA, *Nature,* 273(5658):113-120, 1978.

Footer, Egholm, Kron, Coull, Matsudaira, "Biochemical evidence that a D-loop is part of a four-stranded PNA-DNA bundle. Nickel-mediated cleavage of duplex DNA by a Gly-Gly-His bis-PNA," *Biochemistry,* 35(33):10673-10679, 1996.

Fraley et al., *Biotechnology,* 3:629, 1985.

Fraley, Rogers, Horsch, Sanders, Flick, Adams, Bittner, Brand, Fink, Fry, Galluppi, Goldberg, Hoffmann, Woo, "Expression of bacterial genes in plant cells," *Proc. Natl. Acad. Sci. USA,* 80(15):4803-4807, 1983.

French, Janda, Ahlquist, "Bacterial gene inserted in an engineered RNA virus: efficient expression in monocotyledonous plant cells," *Science,* 231:1294-1297, 1986.

Frohman, *In: PCR™ Protocols: A Guide to Methods and Applications,* Academic Press, New York, 1990.

Fromm, Taylor, Walbot, "Expression of genes transferred into monocot and dicot plant cells by electroporation," *Proc. Natl. Acad. Sci. USA,* 82(17):5824-5828, 1985.

Fromm, Taylor, Walbot, "Stable transformation of maize after gene transfer by electroporation," *Nature,* 319(6056):791-793, 1986.

Fujimura et al., *Plant Tiss. Cult. Lett.,* 2:74, 1985.

Fynan, Webster, Fuller, Haynes, Santoro, Robinson, "DNA vaccines: protective immunizations by parenteral, mucosal, and gene gun inoculations," *Proc. Natl. Acad. Sci. USA,* 90(24):11478-11482, 1993.

Gallie and Young, "The regulation of expression in transformed maize aleurone and endosperm protoplasts," *Plant Physiol.,* 106:929-939, 1994.

Gallie, Feder, Schimke, Walbot, "Post-transcriptional regulation in higher eukaryotes: the role of the reporter gene in controlling expression," *Mol. Gen. Genet.,* 228:258-264, 1991.

Gallie, Lucas, Walbot, "Visualizing mRNA expression in plant protoplasts: factors influencing efficient mRNA uptake and translation," *Plant Cell,* 1:301-311, 1989.

Gallie, Sleat, Turner, Wilson, "Mutational analysis of the tobacco mosaic virus 5'-leader for altered ability to enhance translation," *Nucl. Acids Res.,* 16:883-893, 1988.

Gallie, Sleat, Watts, Turner, Wilson, "A comparison of eukaryotic viral 5'-leader sequences as enhancers of mRNA expression in vivo," *Nucl. Acids Res.,* 15:8693-8711, 1987b.

Gallie, Sleat, Watts, Turner, Wilson, "The 5'-leader sequence of tobacco mosaic virus RNA enhances the expression of foreign gene transcripts in vitro and in vivo," *Nucl. Acids Res.,* 15:3257-3273, 1987a.

Gambacorti-Passerini, Mologni, Bertazzoli, le Coutre, Marchesi, Grignani, Nielsen, "In vitro transcription and translation inhibition by anti-promyelocytic leukemia (PML)/retinoic acid receptor alpha and anti-PML peptide nucleic acid," *Blood,* 88(4):1411-1417, 1996.

Gao and Huang, "Cytoplasmic expression of a reporter gene by co-delivery of T7 RNA polymerase and T7 promoter sequence with cationic liposomes," *Nucl. Acids Res.,* 21(12):2867-2872, 1993.

Gawron-Burke and Baum, "Genetic manipulation of *Bacillus thuringiensis* insecticidal crystal protein genes in bacteria," *Genet. Eng. (N Y),* 13:237-263, 1991.

Gefter, Margulies, Scharff, "A simple method for polyethylene glycol-promoted hybridization of mouse myeloma cells," *Somat. Cell Genet.,* 3(2):231-236, 1977.

Gehrke, Auron, Quigley, Rich, Sonenberg, "5'-Conformation of capped alfalfa mosaic virus ribonucleic acid 4 may reflect its independence of the cap structure or of cap-binding protein for efficient translation," *Biochemistry,* 22:5157-5164, 1983.

Genovese and Milcarek, *In: RNA Processing,* Cold Spring Harbor Laboratory, Cold Spring Harbor, N.Y., p 62, 1988.

Gil and Proudfoot, "A sequence downstream of AAUAAA is required for rabbit beta-globin mRNA 3'-end formation," *Nature,* 312(5993):473-474, 1984.

Gill, Cowles, Francis, "Identification, isolation, and cloning of a *Bacillus thuringiensis* CryIAc toxin-binding protein from the midgut of the lepidopteran insect *Heliothis virescens*," *J. Biol. Chem.,* 270(45):27277-27282, 1995.

Goding, *In: Monoclonal Antibodies: Principles and Practice,* 2nd Edition, Academic Press, Orlando, Fla., pp 60-74, 1986.

Goeddel, Heyneker, Hozumi, Arentzen, Itakura, Yansura, Ross, Miozzari, Crea, Seeburg, "Direct expression in *Escherichia coli* of a DNA sequence for human growth hormone," *Nature,* 281(5732):544-548, 1979.

Goeddel, Shepard, Yelverton, Leung, Crea, Sloma, Pestka, "Synthesis of human fibroblast interferon by *E. coli*," *Nucl. Acids Res.,* 8(18):4057-4074, 1980.

Goelet, Lomonossoff, Butler, Akam, Gait, Karn, "Nucleotide sequence of tobacco mosaic virus RNA," *Proc. Natl. Acad. Sci. USA,* 79:5818-5822, 1982.

Gonzalez Jr. et al., *Proc. Natl. Acad. Sci USA,* 79:6951-6955, 1982.

Good and Nielsen, Antisense Nucl. *Acid Drug Dev.,* 7(4):431-437, 1997.

Graham, Craig, Waterhouse, "Expression patterns of vascular-specific promoters ROlC and Sh in transgenic potatoes and their use in engineering PLRV-resistant plants," *Plant Mol. Biol.,* 33(4):729-735, 1997.

Graham and van der Eb, "Transformation of rat cells by DNA of human adenovirus 5," *Virology,* 54(2):536-539, 1973.

Green, Issemann, Sheer, "A versatile in vivo and in vitro eukaryotic expression vector for protein engineering," *Nucl. Acids Res.,* 16(1):369, 1988.

Griffith et al., *J. Am. Chem. Soc.,* 117:831-832, 1995.

Grochulski, Masson, Borisova, Pusztai-Carey, Schwartz, Brousseau, Cygler, "*Bacillus thuringiensis* CryIA(a) insecticidal toxin: crystal structure and channel formation," *J. Mol. Biol.,* 254(3):447-464, 1995.

Grosset, Alary, Gautier, Menossi, Martinez-Izquierdo, Joudrier, "Characterization of a barley gene coding for an alpha-amylase inhibitor subunit (Cmd protein) and analysis of its promoter in transgenic tobacco plants and in maize kernels by micro projectile bombardment," *Plant Mol. Biol.,* 34(2):331-338, 1997.

Guerrier-Takada, Gardiner, Marsh, Pace, Altman, "The RNA moiety of ribonuclease P is the catalytic subunit of the enzyme," *Cell,* 35(3 Pt 2):849-857, 1983.

Haaima, Lohse, Buchardt, Nielsen, *Angew. Chem., Int. Ed. Engl.,* 35:1939-1942, 1996.

Hampel and Tritz, "RNA catalytic properties of the minimum (−)sTRSV sequence," *Biochemistry,* 28(12):4929-4933, 1989.

Hampel, Tritz, Hicks, Cruz, "'Hairpin' catalytic RNA model: evidence for helices and sequence requirement for substrate RNA," *Nucl. Acids Res.,* 18(2):299-304, 1990.

Hanvey, Peffer, Bisi, Thomson, Cadilla, Josey, Ricca, Hassman, Bonham, Au K G et al., *Science,* 258(5087):1481-1485, 1992.

Harlow and Lane, *In: Antibodies: A Laboratory Manual*, Cold Spring Harbor Laboratory, Cold Spring Harbor, N.Y., pp ?, 1988.

Henry-Michelland et al., "Attachment of antibiotics to nanoparticles; Preparation, drug-release and antimicrobial activity in vitro," *Int. J. Pharm.*, 35:121-127, 1987.

Herrnstadt et al., *Bio/Technology*, 4:305-308, 1986.

Herrnstadt, Gilroy, Sobieski, Bennett, Gaertner, "Nucleotide sequence and deduced amino acid sequence of a coleopteran-active delta-endotoxin gene from *Bacillus thuringiensis* subsp. *san diego*," *Gene*, 57(1):37-46, 1987.

Hess, Boiteux, Kruger, "Cooperation of glycolytic enzymes," *Adv. Enzyme Regul.*, 7:149-167, 1969.

Hess, *Intern Rev. Cytol.*, 107:367, 1987.

Hilber, Bodmer, Smith, Koller, "Biolistic transformation of conidia of *Botryotinia fuckeliana*," *Curr. Genet.*, 25(2):124-127, 1994.

Hitzeman, Clarke, Carbon, "Isolation and characterization of the yeast 3-phosphoglycerokinase gene (PGK) by an immunological screening technique," *J. Biol. Chem.*, 255(24):12073-12080, 1980.

Höfte and Whiteley, "Insecticidal crystal proteins of *Bacillus thuringiensis*," *Microbiol. Rev.*, 53(2):242-255, 1989.

Höfte, Seurinck, Van houstven, Vaeck, "Nucleotide sequence of a gene encoding an insecticidal protein of *Bacillus thuringiensis* var. *tenebrionis* toxic against Coleoptera," *Nucl. Acids Res.*, 15(17):7183, 1987.

Holland and Holland, "Isolation and identification of yeast messenger ribonucleic acids coding for enolase, glyceraldehyde-3-phosphate dehydrogenase, and phosphoglycerate kinase," *Biochemistry*, 17(23):4900-4907, 1978.

Honee, Convents, Van Rie, Jansens, Peferoen, Visser, "The C-terminal domain of the toxic fragment of a *Bacillus thuringiensis* crystal protein determines receptor binding," *Mol. Microbiol.*, 5(11):2799-2806, 1991.

Hoover et al., (Eds.), *In: Remington's Pharmaceutical Sciences*, 15th Edition, Mack Publishing Co., Easton, Pa., pp ?, 1975.

Hopp and Woods, "Prediction of protein antigenic determinants from amino acid sequences," *Proc. Natl. Acad. Sci. USA*, 78(6):3824-3828, 1981.

Horsch, Fry, Hoffmann, Eichholtz, Rogers, Fraley, "A simple and general method for transferring genes into plants," *Science*, 227(4691):1229-1231, 1985.

Horton, Hunt, Ho, Pullen, Pease, "Engineering hybrid genes without the use of restriction enzymes: genen splicing by overlap extension," *Gene*, 77(1):61-68, 1989.

Huang, An, McDowell, McKinney, Meagher, "The *Arabidopsis* ACT11 action gene is strongly expressed in tissues of the emerging inflorescence, pollen and developing ovules," *Plant Mol. Biol.*, 33(1):125-139, 1997.

Hudspeth and Grula, "Structure and expression of the maize gene encoding the phosphoenolpyruvate carboxylase isozyme involved in C4 photosynthesis," *Plant Mol. Biol.*, 12:579-589, 1989.

Hyrup and Nielsen, "Peptide nucleic acids (PNA): synthesis, properties and potential applications," *Bioorg. Med. Chem.*, 4(1):5-23, 1996.

Ingelbrecht, Herman, Dekeyser, Van Montagu, Depicker, "Different 3' end regions strongly influence the level of gene expression in plant cells," *Plant Cell*, 1:671-680, 1989.

Itakura, Hirose, Crea, Riggs, Heyneker, Bolivar, Boyer, "Expression in *Escherichia coli* of a chemically synthesized gene for the hormone somatostatin," *Science*, 198(4321):1056-1063, 1977.

Jaeger, Turner, Zuker, "Improved predictions of secondary structures for RNA," *Proc. Natl. Acad. Sci USA*, 86(20):7706-7710, 1989.

Jameson and Wolf, "The Antigenic Index: A Novel Algorithm for Predicting Antigenic Determinants," *Compu. Appl. Biosci.*, 4(1):181-6, 1988.

Jensen, Orum, Nielsen, Norden, "Kinetics for hybridization of peptide nucleic acids (PNA) with DNA and RNA studied with the BIAcore technique," *Biochemistry*, 36(16):5072-5077, 1997.

Jobling and Gehrke, "Enhanced translation of chimaeric messenger RNAs containing a plant viral untranslated leader sequence," *Nature*, 325:622-625, 1987.

Johnston and Tang, "Gene gun transfection of animal cells and genetic immunization," *Methods Cell. Biol.*, 43(A):353-365, 1994.

Jones, Dean, Gidoni, Gilbert, Bond-Nutter, Lee, Bedbrook, Dunsmuir, "Expression of bacterial chitinase protein in tobacco leaves using two photosynthetic gene promoters," *Mol. Gen. Genet.*, 212:536-542, 1988.

Jones, "Proteinase mutants of *Saccharomyces cerevisiae*," *Genetics*, 85(1):23-33, 1977.

Joshi, "An inspection of the domain between putative TATA box and translation start site in 79 plant genes," *Nucl. Acids Res.*, 15:6643-6653, 1987.

Kaiser and Kezdy, "Amphiphilic secondary structure: design of peptide hormones," *Science*, 223(4633):249-255, 1984.

Kashani-Saber et al., *Antisense Res. Dev.*, 2:3-15, 1992.

Keller et al., *EMBO J.*, 8:1309-14, 1989.

Kingsman, Clarke, Mortimer, Carbon, "Replication in *Saccharomyces cerevisiae* of plasmid pBR313 carrying DNA from the yeast trpl region," *Gene*, 7(2):141-152, 1979.

Klee, Yanofsky, Nester, "Vectors for transformation of higher plants," *Biotechnology*, 3(7):637-642, 1985.

Klein et al., *Nature*, 327:70, 1987.

Klein et al., *Proc. Natl. Acad. Sci. USA*, 85:8502-8505, 1988.

Knight et al., *J. Biol. Chem.*, 270:17765-17770, 1995.

Koch et al., *Tetrahedron Lett.*, 36:6933-6936, 1995.

Kohler and Milstein, "Derivation of specific antibody-producing tissue culture and tumor lines by cell fusion," *Eur. J. Immunol.*, 6(7):511-519, 1976.

Kohler and Milstein, "Continuous cultures of fused cells secreting antibody of predefined specificity," *Nature*, 256(5517):495-497, 1975.

Koppelhus, Zachar, Nielsen, Liu, Eugen-Olsen, Ebbesen, "Efficient in vitro inhibition of HIV-1 gag reverse transcription by peptide nucleic acid (PNA) at minimal ratios of PNA/RNA," *Nucl. Acids Res.*, 25(11):2167-2173, 1997.

Korn and Queen, "Analysis of biological sequences on small computers," *DNA*, 3(6):421-436, 1984.

Kozak, "Point mutations close to the AUG initiator codon affect the efficiency of translation of rat preproinsulin in vivo," *Nature*, 308(5956):241-246, 1984.

Koziel, Beland, Bowman, Carozzi, Crenshaw, Crossland, Dawson, Desai, Hill, Kadwell, Launis, Lewis, Maddox, McPherson, Meghji, Merlin, Rhodes, Warren, Wright, Evola, "Field performance of elite transgenic maize plants expressing an insecticidal protein derived from *Bacillus thuringiensis*," *Biotechnology*, 11:194-200, 1993.

Koziel, Carozzi, Desai, "Optimizing expression of transgenes with an emphasis on post-transcriptional events," *Plant Mol. Biol.*, 32(102):393-405, 1996.

Koziel, Fujimoto, Izawa, Shimamoto, "Anaerobic induction and tissue (see notes on original—cannot complete)

Kremsky et al., *Tetrahedron Lett.*, 37:4313-4316, 1996.

Krieg et al., *AnzSchaed. lingskde, Pflanzenschutz, Umwelrschulz*, 57:145-150, 1984.

Krieg et al., *In: Zangew. Ent.*, 96:500-508, 1983.

Krieg et al., *J. Appl. Ent.*, 104:417-424, 1987.

Kuby, *In: Immunology*, 2nd Edition, W. H. Freeman & Company, New York, pp ?, 1994.

Kunkel, Roberts, Zakour, "Rapid and efficient site-specific mutagenesis without phenotypic selection," *Methods Enzymol*, 154:367-382, 1987.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA*, 86(4):1173-1177, 1989.

Kyozuka, Fujimoto, Izawa, Shimamoto, "Anaerobic induction and tissue-specific expression of maize Adh1 promoter in transgenic rice plants and their progeny," *Mol. Gen. Genet.*, 228(1-2):40-48, 1991.

Kyte and Doolittle, "A simple method for displaying the hydropathic character of a protein," *J. Mol. Biol.*, 157(1):105-132, 1982.

L'Huillier, Davis, Bellamy, "Cytoplasmic delivery of ribozymes leads to efficient reduction in alpha-lactalbumin mRNA levels in C127I mouse cells," *EMBO J*, 11:4411-8, 1992.

Ladd Jr., *J. Econ. Entomol.*, 79:00668-671, 1986.

Lambert et al., *Appl. Environ. Microbiol.*, 58:2536-2642, 1992b.

Lambert et al., *Gene*, 110:131-132, 1992a.

Landsdorp et al., *Hum. Mol. Genet.*, 5:685-691, 1996.

Langridge et al., *Proc. Natl. Acad. Sci. USA*, 86:3219-3223, 1989.

Lee, Young, Dean, "Domain III exchanges of *Bacillus thuringiensis* CryIA toxins affect binding to different gypsy moth midgut receptors," *Biochem. Biophys. Res. Commun.,* 216(1):306-312, 1995.
Lieber, Sandig, Sommer, Bahring, Strauss, "Stable high-level gene expression in mammalian cells by T7 phage RNA polymerase," *Methods Enzymol.,* 217:47-66, 1993.
Lindstrom, Vodkin, Harding, Goeken, "Expression of soybean lectin gene deletions in tobacco," *Dev. Genet,* 11(2):160-167, 1990.
Lisziewicz et al., *Proc. Natl. Acad. Sci. U.S.A.,* 90:8000-4, 1993.
Lorz et al., *Mol. Gen. Genet.,* 199:178, 1985.
Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.,* 178(6):2089-2096, 1993.
Luehrsen and Walbot, "Intron enhancement of gene expression and the splicing efficiency of introns in maize cells," *Mol. Gen. Genet.,* 225:81-93, 1991.
Luo et al., Plant Mol. Biol. Reporter, 6:165, 1988.
Lutcke, Chow, Mickel, Moss, Kern, Scheele, "Selection of AUG initiation codons differs in plants and animals," *EMBO J.,* 6:43-48, 1987.
Maas, Laufs, Grant, Korfhage, Werr, "The combination of a novel stimulatory element in the first exon of the maize shrunken-1 gene with the following intron enhances reporter gene expression 1000-fold," *Plant Mol. Biol.,* 16:199-207, 1991.
Macaluso and Mettus, "Efficient transformation of *Bacillus thuringiensis* requires nonmethylated plasmid DNA," *J. Bacteriol.,* 173(3):1353-1356, 1991.
Maddock et al., *Third International Congress of Plant Molecular Biology*, Abstract 372, 1991.
Maloy, *In: Experimental Techniques in Bacterial Genetics*, Jones and Bartlett Publishers, Boston, Mass., pp ?, 1990.
Maloy et al., *In: Microbial Genetics,* 2nd Edition, Jones and Barlett Publishers, Boston, Mass., pp ?, 1994.
Maniatis et al., *In: Molecular Cloning: a Laboratory Manual*, Cold Spring Harbor Laboratory, Cold Spring Harbor, N.Y., pp ?, 1982.
Marcotte et al., *Nature,* 335:454, 1988.
Mascerenhas, Mettler, Pierce, Lowe, "Intron mediated enhancement of heterologous gene expression in maize," *Plant Mol. Biol.,* 15:913-920, 1990.
Masson, Lu, Mazza, Brousseau, Adang, "The CryIA(c) receptor purified from *Manduca sexta* displays multiple specificities," *J. Biol. Chem.,* 270(35):20309-20315, 1995.
McBride, Svab, Schaaf, Hogan, Stalker, Maliga, "Amplification of a chimeric *Bacillus* gene in chloroplasts leads to an extraordinary level of an insecticidal protein in tobacco," *Biotechnology,* 13:362-365, 1995.
McCabe et al., *Biotechnology,* 6:923, 1988.
McDevitt et al., *Cell,* 37:993-999, 1984.
McElroy, Zhang, Wu, "Isolation of an efficient promoter for use in rice transformation," *Plant Cell,* 2:163-171, 1990.
McPherson et al., *Bio/Technology,* 6:61-66, 1988.
Mettus and Macaluso, *Appl. Environ. Microbiol.,* 56:1128-1134, 1990.
Michael, "Mutagenesis by Incorporation of a Phosphorylated Oligo During PCR™ Amplification," *BioTechniques,* 16(3):410-412, 1994.
Mollegaard, Buchardt, Egholm, Nielsen, *Proc. Natl. Acad. Sci. USA,* 91:3892-3895, 1994.
Nawrath, Poirier, Somerville, "Targeting of the polyhydroxybutyrate biosynthetic pathway to the plastids of *Arabidopsis thaliana* results in high levels of polymer accumulation," *Proc. Natl. Acad. Sci. USA,* 91:12760-12764, 1994.
Neilsen, *In: Perspectives in Drug Discovery and Design* 4, Escom Science Publishers, City/State, pp 76-84, 1996.
Neuhaus et al., *Theor. Appl. Genet.,* 75:30, 1987.
Nielsen, Egholm, Berg, Buchardt, "Peptide nucleic acids (PNAs): potential antisense and anti-gene agents," *Anticancer Drug Des.,* 8(1):53-63, 1993b.
Nielsen, Egholm, Berg, Buchardt, *Science,* 254(5037):1497-1500, 1991.
Norton, Orzech, Burke Jr., "Construction and characterization of plasmid vectors for cloning in the entomocidal organism *Bacillus sphaericus* 1593," *Plasmid,* 13(3):211-214, 1985.
Norton, Piatyszek, Wright, Shay, Corey, "Inhibition of human telomerase activity by peptide nucleic acids," *Nat. Biotechnol.,* 14(5):615-619, 1996.
Norton, Waggenspack, Varnum, Corey, *Bioorg. Med. Chem.,* 3:437-445, 1995.
Oard, Paige, Dvorak, "Chimeric gene expression using maize intron in cultured cells of breadwheat," *Plant Cell. Rep.,* 8:156-160, 1989.
Odell, Nagy, Chua, "Identification of DNA sequences required for activity of the cauliflower mosaic virus 35S promoter," *Nature,* 313(6005):810-812, 1985.
Ohkawa, Yuyama, Taira, "Activities of HIV-RNA targeted ribozymes transcribed from a 'shot-gun' type ribozyme-trimming plasmid," *Nucl. Acids Symp. Ser.,* 27:15-6, 1992.
Ojwang, Hampel, Looney, Wong-Staal, Rappaport, "Inhibition of human immunodeficiency virus type 1 expression by a hairpin ribozyme," *Proc. Natl. Acad. Sci. USA,* 89(22):10802-10806, 1992.
Omirulleh, Abraham, Golovkin, Stefanov, Karabaev, Mustardy, Morocz, Dudits, "Activity of a chimeric promoter with the doubled CaMV 35S enhancer element in protoplast-derived cells and transgenic plants in maize," *Plant Mol. Biol.,* 21(3):415-428, 1993.

Orum, Nielsen, Egholm, Berg, Buchardt, Stanley, "Single base pair mutation analysis by PNA directed PCR™ clamping," *Nucl. Acids Res.*, 21(23):5332-5336, 1993.

Orum, Nielsen, Jorgensen, Larsson, Stanley, Koch, "Sequence-specific purification of nucleic acids by PNA-controlled hybrid selection," *Biotechniques*, 19(3):472-480, 1995.

Pandey and Marzluff, *In: RNA Processing*, Cold Spring Harbor Laboratory, Cold Spring Harbor, N.Y., p 133, 1987.

Pardridge, Boado, Kang, "Vector-medidated delivery of a polyamide ("peptide") nucleic acid analogue through the blood-brain barrier in vivo," *Proc. Natl. Acad. Sci. USA*, 92(12):5592-5596, 1995.

Perlak, Deaton, Armstrong, Fuchs, Sims, Greenplate, Fischhoff, "Insect resistant cotton plants," *Biotechnology*, 8:939-943, 1990.

Perlak, Fuchs, Dean, McPherson, Fischhoff, "Modification of the coding sequence enhances plant expression of insect control protein genes," *Proc. Natl. Acad. Sci USA*, 88:3324-3328, 1991.

Perlak, Stone, Muskopf, Peterson, Parker, McPherson, Wyman, Love, Reed, Biever, Fischhoff, "Genetically improved potatoes: protection from damage by Colorado potato beetles," *Plant Mol. Biol.*, 22:313-321, 1993.

Perreault, Wu, Cousineau, Ogilvie, Cedergren, "Mixed deoxyribo- and ribo-oligonucleotides with catalytic activity," *Nature*, 344(6266):565-567, 1990.

Perrotta and Been, "Cleavage of oligoribonucleotides by a ribozyme derived from the hepatitis delta virus RNA sequence," *Biochemistry*, 31(1):16-21, 1992.

Perry-O'Keefe, Yao, Coull, Fuchs, Egholm, "Peptide nucleic acid pre-gel hybridization: an alternative to southern hybridization," *Proc. Natl. Acad. Sci. USA*, 93(25):14670-14675, 1996.

Petersen, Jensen, Egholm, Nielsen, Buchardt, *Bioorg. Med. Chem. Lett.*, 5:1119-1124, 1995.

Pieken, Olsen, Benseler, Aurup, Eckstein, "Kinetic characterization of ribonuclease-resistant 2'-modified hammerhead ribozymes," *Science*, 253(5017):314-317, 1991.

Poogin and Skryabin, "The 5' untranslated leader sequence of potato virus X RNA enhances the expression of the heterologous gene in vivo," *Mol. Gen. Genet.*, 234:329-331, 1992.

Potrykus, Paszkowski, Saul, Petruska, Shillito, "Molecular and general genetics of a hybrid foreign gene introduced into tobacco by direct gene transfer," *Mol. Gen. Genet.*, 199(2):169-177, 1985.

Poulsen et al., "Characterization of an RBC-S gene from *Nicotiana plumbaginifolia* and expression of an RBC-S-CAT chimeric gene in homologous and heterologous nuclear background," *Mol. Gen. Genet.*, 205(2):193-200, 1986.

Prokop and Bajpai, "Recombinant DNA Technology I," *Ann. N.Y. Acad. Sci.*, 646:1-383, 1991.

Rogers et al., *In: Methods For Plant Molecular Biology*, Weissbach and Weissbach (Eds.), Academic Press Inc., San Diego, Calif., pp ?, 1988.

Rogers et al., *Methods Enzymol.*, 153:253-277, 1987.

Rose, "Characterization of antisense binding properties of peptide nucleic acids by capillary gel electrophoresis," *Anal. Chem.*, 65(24):3545-3549, 1993.

Rossi, Elkins, Zaia, Sullivan, "Ribozymes as anti-HIV-1 therapeutic agents: principles, applications, and problems," *AIDS Res. Hum. Retrovir.*, 8(2):183-189, 1992.

Rupar et al., *Appl. Environ. Microbiol.*, 57:3337-3344, 1991.

Rusckowski, Qu, Chang, Hnatowich, "Pretargeting using peptide nucleic acid," *Cancer*, 80(12 Suppl):2699-2705, 1997.

Russell and Fromm, "Tissue-specific expression in transgenic maize for four endosperm promoters from maize and rice," *Transgenic Res.*, 6(2):157-168, 1997.

Sadofsky and Alwine, "Sequences on the 3' side of hexanucleotide AAUAAA affect efficiency of cleavage at the polyadenylation site," *Mol. Cell. Biol.*, 4(8):1460-1468, 1984.

Sambrook et al., *In: Antibodies: A Laboratory Manual*, Cold Spring Harbor Laboratory, Cold spring Harbor, N.Y., pp ?, 1989a.

Sambrook et al., *In: Molecular Cloning: A Laboratory Manual*, Cold Spring Harbor Laboratory, Cold Spring Harbor, N.Y., pp ?, 1989b.

Sanger, Nicklen, Coulson, "DNA sequencing with chain-terminating inhibitors," *Proc. Natl. Acad. Sci. USA*, 74(12):5463-5467, 1977.

Saville and Collins, "A site-specific self-cleavage reaction performed by a novel RNA in *Neurospora* mitochondria," *Cell*, 61(4):685-696, 1990.

Saville and Collins, "RNA-mediated ligation of self-cleavage products of a *Neurospora* mitochondrial plasmid transcript," *Proc. Natl. Acad. Sci. USA*, 88(19):8826-8830, 1991.

Scanlon, Jiao, Funato, Wang, Tone, Rossi, Kashani-Sabet," *Proc. Natl. Acad. Sci. USA*, 88(23):10591-10595, 1991.

Scaringe, Francklyn, Usman, "Chemical synthesis of biologically active oligoribonucleotides using beta-cyanoethyl protected ribonucleoside phosphoramidites," *Nucl. Acids Res.*, 18(18):5433-5441, 1990.

Seeger, Batz, Orum, "PNA-mediated purification of PCR™ amplifiable human genomic DNA from whole blood," *Biotechniques*, 23(3):512-517, 1997.

Segal, *In: Biochemical Calculations*, 2nd Edition, John Wiley & Sons, New York, N.Y., pp ?, 1976.

Shaw and Kamen, "A conserved AU sequence from the 3' untranslated region of GM-CSF mRNA mediates selective mRNA degradation," *Cell*, 46(5):659-667, 1986.

Shaw and Kamen, *In: RNA Processing*, Cold Spring Harbor Laboratory, Cold Spring Harbor, N.Y., p 220, 1987.

Sick, Gaertner, Wong, "Nucleotide sequence of a coleopteran-active toxin gene from a new isolate of *Bacillus thuringiensis* subsp. *tolworthi*," *Nucl. Acids Res.*, 18(5):1305, 1990.

Simpson, *Science*, 233:34, 1986.

Sleat, Gallie, Jefferson Bevan, Turner, Wilson, "Characterization of the 5'-leader sequence of tobacco mosaic virus RNA as a general enhancer of translation in vitro," *Gene*, 217:217-225, 1987.

Sleat, Hull, Turner, Wilson, "Studies on the mechanism of translational enhancement by the 5'-leader sequence of tobacco mosaic virus RNA," *Eur. J. Biochem.*, 175:75-86, 1988.

Southern, "Detection of specific sequences among DNA fragments separated by gel electrophoresis," *J. Mol. Biol.*, 98(3):503-517, 1975.

Spielmann et al., *Mol. Gen. Genet.*, 205:34, 1986.

Stetsenko, Lubyako, Potapov, Azhikina, Sverdlov, *Tetrahedron Lett.*, 37:3571-3574, 1996.

Taira, Nakagawa, Nishikawa, Furukawa, "Construction of a novel RNA-transcript-trimming plasmid which can be used both in vitro in place of run-off and (G)-free transcriptions and in vivo as multi-sequences transcription vectors," *Nucl. Acids Res.*, 19(19):5125-5130, 1991.

Tanaka, Mita, Ohta, Kyozuka, Shimamoto, Nakamura, "Enhancement of foreign gene expression by a dicot intron in rice but not in tobacco is correlated with an increased level of mRNA and an efficient splicing of the intron," *Nucl. Acids Res.*, 18:6767-6770, 1990.

Thiede, Bayerdorffer, Blasczyk, Wittig, Neubauer, "Simple and sensitive detection of mutations in the ras protooncogenes using PNA-mediated PCR™ clamping," *Nucl. Acids Res.*, 24(5):983-984, 1996.

Thisted, Just, Petersen, Hyldig-Nielsen, Godtfredsen, *Cell Vision*, 3:358-363, 1996.

Thomson et al., *Tetrahedron*, 51:6179-6194, 1995.

Tomic, Sunjevaric, Savtchenko, Blumenberg, "A rapid and simple method for introducing specific mutations into any position of DNA leaving all other positions unaltered," *Nucl. Acids Res.*, 18(6):1656, 1990.

Toriyama et al., *Theor Appl. Genet.*, 73:16, 1986.

Treacy, Hattori, Prud'homme, Barbour, Boutilier, Baszczynski, Huang, Johnson, Miki, "Bnm1, a *Brassica* pollen-specific gene," *Plant Mol. Biol.*, 34(4):603-611, 1997.

Uchimiya et al., *Mol. Gen. Genet.*, 204:204, 1986.

Ulmann, Will, Breipohl, Langner, Ryte, *Angew. Chem., Int. Ed. Engl.*, 35:2632-2635, 1996.

Upender, Raj, Weir, "Megaprimer method for in vitro mutagenesis using parallel templates," *Biotechniques*, 18:29-31, 1995.

Usman et al., *J. Am. Chem. Soc.*, 109:7845-7854, 1987.

Usman and Cedergren, "Exploiting the chemical synthesis of RNA," *Trends Biochem. Sci.*, 17(9):334-339, 1992.

Van Camp, Herouart, Willekens, Takahashi, Saito, Van Montagu, Inze, "Tissue-specific activity of two manganese superoxide dismutase promoters in transgenic tobacco," *Plant Physiol.*, 112(2):525-535, 1996.

van Tunen, Koes, Spelt, van der Krol, Stuitje, Mol, "Cloning of the two chalcone flavanone isomerase genes from *Petunia hybrida*: coordinate, light-regulated and differential expression of flavanoid genes," *EMBO J.*, 7(5):1257-1263, 1988.

Vander, Van Montagu, Inze, Boerjan, "Tissue-specific expression conferred by the S-adenosyl-L-methionine synthetase promoter of *Arabidopsis thaliana* in transgenic poplar," *Plant Cell Physiol.*, 37(8): 1108-1115, 1996.

Vasil et al., "Herbicide-resistant fertile transgenic wheat plants obtained by microprojectile bombardment of regenerable embryogenic callus," *Biotechnology*, 10:667-674, 1992.

Vasil, *Biotechnology*, 6:397, 1988.

Vasil, Clancy, Ferl, Vasil, Hannah, "Increased gene expression by the first intron of maize shrunken-1 locus in grass species," *Plant Physiol.*, 91:1575-1579, 1989.

Velten et al., *EMBO J.*, 3:2723-2730, 1984.

Velten and Schell, "Selection-expression plasmid vectors for use in genetic transformation of higher plants," *Nucl. Acids Res.*, 13(19):6981-6998, 1985.

Ventura, Wang, Ragot, Perricaudet, Saragosti, "Activation of HIV-specific ribozyme activity by self-cleavage," *Nucl. Acids Res.*, 21(14):3249-3255, 1993.

Veselkov, Demidov, Nielson, Frank-Kamenetskii, "A new class of genome rare cutters," *Nucl. Acids Res.*, 24(13): 2483-2487, 1996.

Vickers, Griffith, Ramasamy, Risen, Freier, "Inhibition of NF-kappa B specific transcriptional activation by PNA strand invasion," *Nucl. Acids Res.*, 23(15):3003-3008, 1995.

Vodkin, "cA lectin gene insertion has the structural features of a transposable element," *Cell*, 34(3):1023-1031, 1983.

Vogel, Dawe, Freeling, "Regulation of the cell type-specific expression of maize Adh1 and Sh1 electroporation-directed gene transfer into protoplasts of several maize tissues," *J. Cell. Biochem.*, (Suppl. 0) 13:Part D, 1989.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA*, 89(13):6099-6103, 1992.

Walker, Little, Nadeau, Shank, "Isothermal in vitro amplification of DNA by a restriction enzyme/DNA polymerase system," *Proc. Natl. Acad. Sci. USA*, 89(1):392-396, 1992.

Wang, *J. Am. Chem. Soc.*, 118:7667-7670, 1996.

Watson, "Fluid and electrolyte disorders in cardiovascular patients," *Nurs. Clin. North Am.*, 22(4):797-803, 1987.

Webb and Hurskainen, *J. Biomol. Screen.*, 1:119-121, 1996.

Weerasinghe, Liem, Asad, Read, Joshi, "Resistance to human immunodeficiency virus type 1 (HIV-1) infection in human CD4+ lymphocyte-derived cell lines conferred by using retroviral vectors expressing an HIV-1 RNA-specific ribozyme," *J. Virol.*, 65(10):5531-5534, 1991.

Weissbach and Weissbach (Eds.), In: *Methods for Plant Molecular Biology*, Academic Press, Inc., San Diego, Calif., pp ?, 1988.

Wenzler, Mignery, Fisher, Park, "Sucrose-regulated expression of a chimeric potato tuber gene in leaves of transgenic tobacco plants," *Plant Mol. Biol.*, 13(4):347-354, 1989.

Wickens and Stephenson, "Role of the conserved AAUAAA sequence: four AAUAAA point mutants prevent messenger RNA 3' end formation," *Science*, 226(4678):1045-1051, 1984.

Wickens et al., In: *RNA Processing*, Cold Spring Harbor Laboratory, Cold Spring Harbor, N.Y., p 9, 1987.

Wilson, Flint, Deaton, Fischhoff, Perlak, Armstrong, Fuchs, Berberich, Parks, Stapp, "Resistance of cotton lines containing a *Bacillus thuringiensis* toxin to pink bollworm (Lepidopteran: Gelechiidae) and other insects," *J. Econ. Entomol.*, 4:1516-1521, 1992.

Wolf, Modrow, Motz, Jameson, Hermann, Fortsch, "An integrated family of amino acid sequence analysis programs," *Comput. Appl. Biosci.*, 4(1):187-191 1988.

Wong and Neumann, "Electric field mediated gene transfer," *Biochim. Biophys. Res. Commun.*, 107(2):584-587, 1982.

Woolf, Melton, Jennings, "Specificity of antisense oligonucleotides in vivo," *Proc. Natl. Acad. Sci. USA*, 89(16): 7305-7309, 1992.

Wu and Dean, "Functional significance of loops in the receptor binding domain of *Bacillus thuringiensis* CryIIIA delta-endotoxin," *J. Mol. Biol.,* 255(4):628-640, 1996.

Yamada et al., *Plant Cell Rep.,* 4:85, 1986.

Yang et al., *Proc. Natl. Acad Sci USA,* 87:4144-48, 1990.

Yin, Chen, Beachy, "Promoter elements required for phloem-specific gene expression from the RTBV promoter in rice," *Plant J.,* 12(5):1179-1188, 1997b.

Yin, Zhu, Dai, Lamb, Beachy, "RF2a, a bZIP transcriptional activator of the phloem-specific rice tungro bacilliform virus promoter, functions in vascular development," *EMBO J.,* 16(17):5247-5259, 1997a.

Yu, Ojwang, Yamada, Hampel, Rapapport, Looney, Wong-Staal, "A hairpin ribozyme inhibits expression of diverse strains of human immunodeficiency virus type 1," *Proc. Natl. Acad. Sci. USA,* 90(13):6340-6344, 1993.

Zatloukal, Wagner, Cotten, Phillips, Plank, Steinlein, Curiel, Birnstiel, "Transferrinfection: a highly efficient way to express gene constructs in eukaryotic cells," *Ann. N.Y. Acad. Sci.,* 660:136-153, 1992.

Zhou, Weng, Zeng, Huang, Qian, Liu, "Introduction of exogenous DNA into cotton embryos," *Methods Enzymol.,* 101: 433-481, 1983.

Zhou, Giordano, Durbin, McAllister, "Synthesis of functional mRNA in mammalian cells by bacteriophage T3 RNA polymerase," *Mol. Cell Biol.,* 10(9):4529-4537, 1990.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated nucleic acid segment having utility as a probe or primer, wherein said nucleic acid segment comprises at least 100 contiguous nucleotides of SEQ ID NO:1, or the complement thereof.

2. The isolated nucleic acid segment of claim 1, wherein said nucleic acid segment comprises at least 100 contiguous nucleotides of SEQ ID NO:1 from nucleotide 92 to nucleotide 2254, or the complement thereof.

3. A method for detecting a nucleic acid sequence encoding a δ-endotoxin polypeptide, comprising the steps of:

a) obtaining sample nucleic acids suspected of encoding a δ-endotoxin polypeptide;

b) contacting said sample nucleic acids with the isolated nucleic acid segment according to claim 1, under conditions effective to allow hybridization of substantially complementary nucleic acids; and c) detecting the hybridized complementary nucleic acids thus formed.

4. A nucleic acid detection kit comprising, in suitable container means, at least a first nucleic acid segment according to claim 1, and at least a first detection reagent.

* * * * *

```
                              SEQUENCE LISTING

<160> NUMBER OF SEQ ID NOS: 6

<210> SEQ ID NO 1
<211> LENGTH: 2344
<212> TYPE: DNA
<213> ORGANISM: Baccillus thuringiensis
<220> FEATURE:
<221> NAME/KEY: CDS
<222> LOCATION: (92)..(2254)

<400> SEQUENCE: 1
gtaatagtag ttatttagca ggaataaaag ggagggtatc gaatactttc aaatgaagac      60
tgaaaattta caaatagaag gagagaaaag t atg aaa gat tca att tca aag       112
                                   Met Lys Asp Ser Ile Ser Lys
                                   1               5 gga tat gat gaa ata aca gtg cag gca agt gat tat att gat att cgc      160
Gly Tyr Asp Glu Ile Thr Val Gln Ala Ser Asp Tyr Ile Asp Ile Arg
        10                  15                  20 tca att ttt caa acg aat gga tct gca aca ttt aat tca acc act aat      208
Ser Ile Phe Gln Thr Asn Gly Ser Ala Thr Phe Asn Ser Thr Thr Asn
    25                  30                  35 att aca act tta acg caa gct aca aat agt caa gcg gga gca att gca      256
Ile Thr Thr Leu Thr Gln Ala Thr Asn Ser Gln Ala Gly Ala Ile Ala
40                  45                  50                  55 ggg aag aca gct tta gat atg aga cat gat ttt act ttt aga gct gat      304
Gly Lys Thr Ala Leu Asp Met Arg His Asp Phe Thr Phe Arg Ala Asp
                60                  65                  70 att ttt ctt gga act aaa agt aat gga gca gat ggt att gcg ata gca      352
Ile Phe Leu Gly Thr Lys Ser Asn Gly Ala Asp Gly Ile Ala Ile Ala
            75                  80                  85 ttt cat aga gga tca att ggt ttt gtt ggg gag aag ggt gga gga ctt      400
Phe His Arg Gly Ser Ile Gly Phe Val Gly Glu Lys Gly Gly Gly Leu
        90                  95                  100 ggg att tta ggc gcc cta aaa ggt ata gga ttt gaa tta gac aca tat      448
Gly Ile Leu Gly Ala Leu Lys Gly Ile Gly Phe Glu Leu Asp Thr Tyr
    105                 110                 115 gcg aat gct cct caa gat gaa caa gga gat tct ttt gga cat gga gca      496
Ala Asn Ala Pro Gln Asp Glu Gln Gly Asp Ser Phe Gly His Gly Ala
120                 125                 130                 135 atg aga ggc cta ttc cct ggt ttc cca aat gga tat cca cat gct ggt      544
Met Arg Gly Leu Phe Pro Gly Phe Pro Asn Gly Tyr Pro His Ala Gly
                140                 145                 150 ttt gta agt acg gat aaa aat aga ggt tgg tta tct gcc tta gct cag      592
Phe Val Ser Thr Asp Lys Asn Arg Gly Trp Leu Ser Ala Leu Ala Gln
            155                 160                 165
```

```
atg cag cga ata gct gct cca aat ggg cgt tgg aga cgt ctg gcg att        640
Met Gln Arg Ile Ala Ala Pro Asn Gly Arg Trp Arg Arg Leu Ala Ile
        170                 175                 180 cat tgg gat gct cgc aat aaa aaa tta act gca aac ctt gag gat tta        688
His Trp Asp Ala Arg Asn Lys Lys Leu Thr Ala Asn Leu Glu Asp Leu
185                 190                 195 act ttt aat gat tca acg gta tta gtg aaa cca cgt act cca aga tat        736
Thr Phe Asn Asp Ser Thr Val Leu Val Lys Pro Arg Thr Pro Arg Tyr
200                 205                 210                 215 gca aga tgg gag tta tca aat cct gca ttt gaa ctt gat caa aag tat        784
Ala Arg Trp Glu Leu Ser Asn Pro Ala Phe Glu Leu Asp Gln Lys Tyr
                220                 225                 230 act ttt gtt att ggt tca gcg acg ggt gca tct aat aac cta cat cag        832
Thr Phe Val Ile Gly Ser Ala Thr Gly Ala Ser Asn Asn Leu His Gln
            235                 240                 245 att ggt att ata gaa ttt gat gca tac ttt act aaa ccg aca ata gag        880
Ile Gly Ile Ile Glu Phe Asp Ala Tyr Phe Thr Lys Pro Thr Ile Glu
        250                 255                 260 gcg aat aat gta agt gtt ccg gtg gga gca aca ttt aat ccg aaa aca        928
Ala Asn Asn Val Ser Val Pro Val Gly Ala Thr Phe Asn Pro Lys Thr
265                 270                 275 tat cca gga ata aat tta aga gca act gat gaa ata gat ggt gat ttg        976
Tyr Pro Gly Ile Asn Leu Arg Ala Thr Asp Glu Ile Asp Gly Asp Leu
280                 285                 290                 295 aca tct gaa att att gtg aca gat aat aat gtt aat acg tcg aaa tct       1024
Thr Ser Glu Ile Ile Val Thr Asp Asn Asn Val Asn Thr Ser Lys Ser
                300                 305                 310 ggt gtg tat aat gtg acg tat tat gta aag aat agc tat ggg gaa agt       1072
Gly Val Tyr Asn Val Thr Tyr Tyr Val Lys Asn Ser Tyr Gly Glu Ser
            315                 320                 325 gat gaa aaa aca atc gaa gta act gtg ttt tca aac cct aca att att       1120
Asp Glu Lys Thr Ile Glu Val Thr Val Phe Ser Asn Pro Thr Ile Ile
        330                 335                 340 gca agt gat gtt gaa att gaa aaa ggt gaa tcg ttt aat cca tta aca       1168
Ala Ser Asp Val Glu Ile Glu Lys Gly Glu Ser Phe Asn Pro Leu Thr
345                 350                 355 gac tca aga gtg agg ctg tct gca caa gat tca ttg ggt aat gat att       1216
Asp Ser Arg Val Arg Leu Ser Ala Gln Asp Ser Leu Gly Asn Asp Ile
360                 365                 370                 375 act tca aaa gta aag gtg aaa tca agt aat gtg gat act tcg aaa cca       1264
Thr Ser Lys Val Lys Val Lys Ser Ser Asn Val Asp Thr Ser Lys Pro
                380                 385                 390 ggt gaa tat gat gtt gtg ttt gaa gtg acc gat aat ttt ggt ggg aaa       1312
Gly Glu Tyr Asp Val Val Phe Glu Val Thr Asp Asn Phe Gly Gly Lys
            395                 400                 405 gca gaa aaa gaa atc aag gtt aca gtt tta ggg cag cca agt att gaa       1360
Ala Glu Lys Glu Ile Lys Val Thr Val Leu Gly Gln Pro Ser Ile Glu
        410                 415                 420 gcg aat gat gtt gaa tta gaa ata ggt gat tta ttt aat ccg tta aca       1408
Ala Asn Asp Val Glu Leu Glu Ile Gly Asp Leu Phe Asn Pro Leu Thr
425                 430                 435 gat tca caa gta ggc ctt cgt gca aaa gac tca tta ggc aaa gat att       1456
Asp Ser Gln Val Gly Leu Arg Ala Lys Asp Ser Leu Gly Lys Asp Ile
440                 445                 450                 455 acg aat gat gtg aaa gta aag tca agt aat gtg gat act tca aaa cca       1504
Thr Asn Asp Val Lys Val Lys Ser Ser Asn Val Asp Thr Ser Lys Pro
                460                 465                 470 gga gaa tat gaa gtt gta ttt gaa gtg acc gat cgt ttt gga aaa aaa       1552
Gly Glu Tyr Glu Val Val Phe Glu Val Thr Asp Arg Phe Gly Lys Lys
            475                 480                 485
```

```
gca gaa aaa agt atc aaa gtc ctt gtt cta gga gaa cca agc att gaa    1600
Ala Glu Lys Ser Ile Lys Val Leu Val Leu Gly Glu Pro Ser Ile Glu
        490                 495                 500 gca aat aat gtt gag att gaa aaa gac gaa agg ttc gat cca tta aca    1648
Ala Asn Asn Val Glu Ile Glu Lys Asp Glu Arg Phe Asp Pro Leu Thr
505                 510                 515 gat tca aga gta ggt ctc cgt gca aaa gac tca tta ggc aaa gat att    1696
Asp Ser Arg Val Gly Leu Arg Ala Lys Asp Ser Leu Gly Lys Asp Ile
520                 525                 530                 535 acg aat gat gtg aaa gta aaa tca agt aat gtg gat act tca aaa cca    1744
Thr Asn Asp Val Lys Val Lys Ser Ser Asn Val Asp Thr Ser Lys Pro
            540                 545                 550 gga gaa tat gaa gtt gta ttt gaa gtg act gat cgt ttt ggt aaa tat    1792
Gly Glu Tyr Glu Val Val Phe Glu Val Thr Asp Arg Phe Gly Lys Tyr
                555                 560                 565 gta aag aaa ttg att gta gtt ata gta cca gta att gat gat gaa tgg    1840
Val Lys Lys Leu Ile Val Val Ile Val Pro Val Ile Asp Asp Glu Trp
            570                 575                 580 gaa gat gga aat gtg aat gga tgg aaa ttc tat gcg ggg caa gac atc    1888
Glu Asp Gly Asn Val Asn Gly Trp Lys Phe Tyr Ala Gly Gln Asp Ile
585                 590                 595 aca ctg ttg aaa gat cct gaa aaa gca tat aaa gga gaa tat gta ttc    1936
Thr Leu Leu Lys Asp Pro Glu Lys Ala Tyr Lys Gly Glu Tyr Val Phe
600                 605                 610                 615 tat gat tct agg cat gct gct att tct aaa aca atc cca gta aca gat    1984
Tyr Asp Ser Arg His Ala Ala Ile Ser Lys Thr Ile Pro Val Thr Asp
                620                 625                 630 tta caa gtg gga ggg aat tat gaa att aca gta tat gtt aaa gca gaa    2032
Leu Gln Val Gly Gly Asn Tyr Glu Ile Thr Val Tyr Val Lys Ala Glu
            635                 640                 645 agc ggt gat cat cac cta aaa gtg acg tac aag aaa gac ccg aaa ggt    2080
Ser Gly Asp His His Leu Lys Val Thr Tyr Lys Lys Asp Pro Lys Gly
        650                 655                 660 ccg gag gaa cca cca gtt ttc aat aga ctt att agt aca ggg aaa ttg    2128
Pro Glu Glu Pro Pro Val Phe Asn Arg Leu Ile Ser Thr Gly Lys Leu
665                 670                 675 gtg gaa aaa gac tat aga gaa tta aaa gga aca ttc cgt gta acg gaa    2176
Val Glu Lys Asp Tyr Arg Glu Leu Lys Gly Thr Phe Arg Val Thr Glu
680                 685                 690                 695 tta aac caa gca cca ttg ata atc gta gag aat ttt ggt gct gga tat    2224
Leu Asn Gln Ala Pro Leu Ile Ile Val Glu Asn Phe Gly Ala Gly Tyr
                700                 705                 710 ata ggt gga att aga att gtg aaa ata tcg taataaaaac agataaaata     2274
Ile Gly Gly Ile Arg Ile Val Lys Ile Ser
            715                 720 gagagaggaa cgctggatag cgttcctctt ttcagtttag tgtaccatct ccaggtccag    2334
ttcattttt                                                            2344

<210> SEQ ID NO 2
<211> LENGTH: 721
<212> TYPE: PRT
<213> ORGANISM: Baccillus thuringiensis

<400> SEQUENCE: 2

Met Lys Asp Ser Ile Ser Lys Gly Tyr Asp Glu Ile Thr Val Gln Ala
1               5                   10                  15

Ser Asp Tyr Ile Asp Ile Arg Ser Ile Phe Gln Thr Asn Gly Ser Ala
            20                  25                  30
```

```
Thr Phe Asn Ser Thr Thr Asn Ile Thr Thr Leu Thr Gln Ala Thr Asn
            35                  40                  45

Ser Gln Ala Gly Ala Ile Ala Gly Lys Thr Ala Leu Asp Met Arg His
        50                  55                  60

Asp Phe Thr Phe Arg Ala Asp Ile Phe Leu Gly Thr Lys Ser Asn Gly
65                  70                  75                  80

Ala Asp Gly Ile Ala Ile Ala Phe His Arg Gly Ser Ile Gly Phe Val
                    85                  90                  95

Gly Glu Lys Gly Gly Gly Leu Gly Ile Leu Gly Ala Leu Lys Gly Ile
                100                 105                 110

Gly Phe Glu Leu Asp Thr Tyr Ala Asn Ala Pro Gln Asp Glu Gln Gly
            115                 120                 125

Asp Ser Phe Gly His Gly Ala Met Arg Gly Leu Phe Pro Gly Phe Pro
        130                 135                 140

Asn Gly Tyr Pro His Ala Gly Phe Val Ser Thr Asp Lys Asn Arg Gly
145                 150                 155                 160

Trp Leu Ser Ala Leu Ala Gln Met Gln Arg Ile Ala Ala Pro Asn Gly
                    165                 170                 175

Arg Trp Arg Arg Leu Ala Ile His Trp Asp Ala Arg Asn Lys Lys Leu
                180                 185                 190

Thr Ala Asn Leu Glu Asp Leu Thr Phe Asn Asp Ser Thr Val Leu Val
            195                 200                 205

Lys Pro Arg Thr Pro Arg Tyr Ala Arg Trp Glu Leu Ser Asn Pro Ala
        210                 215                 220

Phe Glu Leu Asp Gln Lys Tyr Thr Phe Val Ile Gly Ser Ala Thr Gly
225                 230                 235                 240

Ala Ser Asn Asn Leu His Gln Ile Gly Ile Glu Phe Asp Ala Tyr
                    245                 250                 255

Phe Thr Lys Pro Thr Ile Glu Ala Asn Asn Val Ser Val Pro Val Gly
                260                 265                 270

Ala Thr Phe Asn Pro Lys Thr Tyr Pro Gly Ile Asn Leu Arg Ala Thr
            275                 280                 285

Asp Glu Ile Asp Gly Asp Leu Thr Ser Glu Ile Val Thr Asp Asn
        290                 295                 300

Asn Val Asn Thr Ser Lys Ser Gly Val Tyr Asn Val Thr Tyr Tyr Val
305                 310                 315                 320

Lys Asn Ser Tyr Gly Glu Ser Asp Glu Lys Thr Ile Glu Val Thr Val
                    325                 330                 335

Phe Ser Asn Pro Thr Ile Ile Ala Ser Asp Val Glu Ile Glu Lys Gly
                340                 345                 350

Glu Ser Phe Asn Pro Leu Thr Asp Ser Arg Val Arg Leu Ser Ala Gln
            355                 360                 365

Asp Ser Leu Gly Asn Asp Ile Thr Ser Lys Val Lys Val Lys Ser Ser
        370                 375                 380

Asn Val Asp Thr Ser Lys Pro Gly Glu Tyr Asp Val Phe Glu Val
385                 390                 395                 400

Thr Asp Asn Phe Gly Gly Lys Ala Glu Lys Glu Ile Lys Val Thr Val
                    405                 410                 415

Leu Gly Gln Pro Ser Ile Glu Ala Asn Asp Val Glu Leu Glu Ile Gly
                420                 425                 430

Asp Leu Phe Asn Pro Leu Thr Asp Ser Gln Val Gly Leu Arg Ala Lys
            435                 440                 445
```

-continued

```
Asp Ser Leu Gly Lys Asp Ile Thr Asn Asp Val Lys Val Lys Ser Ser
    450                 455                 460

Asn Val Asp Thr Ser Lys Pro Gly Glu Tyr Glu Val Val Phe Glu Val
465                 470                 475                 480

Thr Asp Arg Phe Gly Lys Lys Ala Glu Lys Ser Ile Lys Val Leu Val
                485                 490                 495

Leu Gly Glu Pro Ser Ile Glu Ala Asn Asn Val Glu Ile Glu Lys Asp
            500                 505                 510

Glu Arg Phe Asp Pro Leu Thr Asp Ser Arg Val Gly Leu Arg Ala Lys
        515                 520                 525

Asp Ser Leu Gly Lys Asp Ile Thr Asn Asp Val Lys Val Lys Ser Ser
    530                 535                 540

Asn Val Asp Thr Ser Lys Pro Gly Glu Tyr Glu Val Val Phe Glu Val
545                 550                 555                 560

Thr Asp Arg Phe Gly Lys Tyr Val Lys Lys Leu Ile Val Val Ile Val
                565                 570                 575

Pro Val Ile Asp Asp Glu Trp Glu Asp Gly Asn Val Asn Gly Trp Lys
            580                 585                 590

Phe Tyr Ala Gly Gln Asp Ile Thr Leu Leu Lys Asp Pro Glu Lys Ala
        595                 600                 605

Tyr Lys Gly Glu Tyr Val Phe Tyr Asp Ser Arg His Ala Ala Ile Ser
    610                 615                 620

Lys Thr Ile Pro Val Thr Asp Leu Gln Val Gly Gly Asn Tyr Glu Ile
625                 630                 635                 640

Thr Val Tyr Val Lys Ala Glu Ser Gly Asp His His Leu Lys Val Thr
                645                 650                 655

Tyr Lys Lys Asp Pro Lys Gly Pro Glu Glu Pro Pro Val Phe Asn Arg
            660                 665                 670

Leu Ile Ser Thr Gly Lys Leu Val Glu Lys Asp Tyr Arg Glu Leu Lys
        675                 680                 685

Gly Thr Phe Arg Val Thr Glu Leu Asn Gln Ala Pro Leu Ile Ile Val
    690                 695                 700

Glu Asn Phe Gly Ala Gly Tyr Ile Gly Gly Ile Arg Ile Val Lys Ile
705                 710                 715                 720

Ser
```

<210> SEQ ID NO 3
<211> LENGTH: 13
<212> TYPE: PRT
<213> ORGANISM: Bacillus thuringiensis

<400> SEQUENCE: 3

```
Ala Ser Asp Tyr Ile Asp Ile Arg Ser Ile Phe Gln Thr
1               5                   10
```

<210> SEQ ID NO 4
<211> LENGTH: 38
<212> TYPE: DNA
<213> ORGANISM: Artificial Sequence
<220> FEATURE:
<223> OTHER INFORMATION: Cry ET70 Oligonucleotide probe
<220> FEATURE:
<221> NAME/KEY: modified_base
<222> LOCATION: (3)..(6)
<223> OTHER INFORMATION: N = Inosine
<220> FEATURE:
<221> NAME/KEY: misc_feature
<222> LOCATION: (3)..(6)
<223> OTHER INFORMATION: N = I

```
<400> SEQUENCE: 4
gcntcngatt atattgatat tagatcaatt tttcaaac                              38

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide probe to Cry ET70

<400> SEQUENCE: 5
gacatgattt tacttttaga gc                                               22

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide probe to Cry ET70

<400> SEQUENCE: 6
catcactttc cccatagc                                                    18
```